United States Patent
Seow et al.

(10) Patent No.: US 11,950,781 B2
(45) Date of Patent: Apr. 9, 2024

(54) DISCRETE ADJUNCT ATTACHMENT FEATURES FOR SURGICAL STAPLER

(71) Applicant: Cilag GmbH International, Zug (CH)

(72) Inventors: Christopher Q. Seow, Cincinnati, OH (US); Taylor W. Aronhalt, Loveland, OH (US); Tyler N. Brehm, Arcanum, OH (US); Zhifan F. Huang, Mason, OH (US); Austin J. Bridges, Huntington Beach, CA (US); Pierre R. Mesnil, Newport, KY (US); Diana M. Darpel, Loveland, OH (US); Morgan R. Hunter, Cincinnati, OH (US); Chad P. Boudreaux, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/514,096

(22) Filed: Oct. 29, 2021

(65) Prior Publication Data
US 2023/0139613 A1    May 4, 2023

(51) Int. Cl.
*A61B 17/072* (2006.01)
*A61B 17/00* (2006.01)

(52) U.S. Cl.
CPC ............ *A61B 17/07292* (2013.01); *A61B 2017/00473* (2013.01); *A61B 2017/00867* (2013.01); *A61B 2017/07257* (2013.01); *A61B 2017/07271* (2013.01); *A61B 2017/07285* (2013.01)

(58) Field of Classification Search
CPC .............. A61B 17/07292; A61B 17/072
See application file for complete search history.

(56) References Cited

U.S. PATENT DOCUMENTS

| | | | |
|---|---|---|---|
| 5,711,960 A | 1/1998 | Shikinami | |
| 7,380,696 B2 | 6/2008 | Shelton, IV et al. | |
| 7,665,646 B2 | 2/2010 | Prommersberger | |
| 8,028,883 B2 * | 10/2011 | Stopek | A61B 17/072 227/176.1 |

(Continued)

FOREIGN PATENT DOCUMENTS

| | | |
|---|---|---|
| EP | 3150143 A1 | 4/2017 |
| EP | 3791806 A1 | 3/2021 |

OTHER PUBLICATIONS

European Examination Report dated Sep. 14, 2023 for Application No. EP 22797890.5, 3 pgs.

(Continued)

*Primary Examiner* — Gloria R Weeks
(74) *Attorney, Agent, or Firm* — Frost Brown Todd LLP

(57) ABSTRACT

An adjunct configured for use with an end effector of a surgical stapler includes a tissue-effecting portion comprising a first material, and at least one movable attachment feature coupled to the tissue-effecting portion and comprising a second material different from the first material. The at least one movable attachment feature is configured to releasably attach the tissue-effecting portion to a stapling surface of the end effector. The tissue-effecting portion is configured to contact tissue clamped by the end effector during closure thereof. The tissue-effecting portion is further configured to be pierced and captured by staples ejected from the end effector into the clamped tissue and thereby reinforce the engagement between the ejected staples and the clamped tissue.

20 Claims, 36 Drawing Sheets

(56) References Cited

U.S. PATENT DOCUMENTS

| | | |
|---|---|---|
| 8,210,411 B2 | 7/2012 | Yates et al. |
| 8,371,491 B2 | 2/2013 | Huitema et al. |
| 8,408,439 B2 | 4/2013 | Huang et al. |
| 8,453,652 B2 | 6/2013 | Stopek |
| 8,453,914 B2 | 6/2013 | Laurent et al. |
| 8,479,968 B2 * | 7/2013 | Hodgkinson ........ A61B 17/115 606/139 |
| 8,757,465 B2 | 6/2014 | Woodard, Jr. et al. |
| 8,893,949 B2 | 11/2014 | Shelton, IV et al. |
| 8,899,464 B2 | 12/2014 | Hueil et al. |
| 8,978,954 B2 | 3/2015 | Shelton, IV et al. |
| 9,055,941 B2 | 6/2015 | Schmid et al. |
| 9,186,142 B2 | 11/2015 | Fanelli et al. |
| 9,232,941 B2 | 1/2016 | Mandakolathur Vasudevan et al. |
| 9,289,207 B2 | 3/2016 | Shelton, IV |
| 9,301,752 B2 | 4/2016 | Mandakolathur Vasudevan et al. |
| 9,301,753 B2 | 4/2016 | Aldridge et al. |
| 9,307,989 B2 | 4/2016 | Shelton, IV et al. |
| 9,314,246 B2 | 4/2016 | Shelton, IV et al. |
| 9,332,974 B2 | 5/2016 | Henderson et al. |
| 9,364,233 B2 | 6/2016 | Alexander, III et al. |
| 9,386,984 B2 | 7/2016 | Aronhalt et al. |
| 9,480,476 B2 | 11/2016 | Aldridge et al. |
| 9,517,065 B2 | 12/2016 | Simms et al. |
| 9,585,657 B2 * | 3/2017 | Shelton, IV ....... A61B 17/1155 |
| 9,615,826 B2 * | 4/2017 | Shelton, IV ..... A61B 17/07292 |
| 9,622,746 B2 | 4/2017 | Simms et al. |
| 9,717,497 B2 | 8/2017 | Zerkle et al. |
| 9,795,379 B2 | 10/2017 | Leimbach et al. |
| 9,808,248 B2 | 11/2017 | Hoffman |
| 9,839,421 B2 | 12/2017 | Zerkle et al. |
| 9,918,716 B2 | 3/2018 | Baxter, III et al. |
| 9,936,950 B2 | 4/2018 | Shelton, IV et al. |
| 10,092,292 B2 | 10/2018 | Boudreaux et al. |
| 10,166,023 B2 | 1/2019 | Vendely et al. |
| 10,172,620 B2 * | 1/2019 | Harris ................... A61L 17/105 |
| 10,258,330 B2 | 4/2019 | Shelton, IV et al. |
| 10,285,691 B2 | 5/2019 | Shelton, IV et al. |
| 10,285,699 B2 | 5/2019 | Vendely et al. |
| 10,307,160 B2 | 6/2019 | Vendely et al. |
| 10,327,776 B2 | 6/2019 | Harris et al. |
| 10,327,777 B2 | 6/2019 | Harris et al. |
| 10,342,542 B2 | 7/2019 | Barton et al. |
| 10,357,251 B2 | 7/2019 | Shelton, IV et al. |
| 10,433,846 B2 | 10/2019 | Vendely et al. |
| 10,441,285 B2 | 10/2019 | Shelton, IV et al. |
| 10,485,544 B2 | 11/2019 | Shelton, IV et al. |
| 10,524,788 B2 | 1/2020 | Vendely et al. |
| 10,548,597 B2 * | 2/2020 | Dunki-Jacobs ........ A61B 17/26 |
| 10,568,621 B2 | 2/2020 | Shelton, IV et al. |
| 10,569,071 B2 | 2/2020 | Harris et al. |
| 10,588,623 B2 | 3/2020 | Schmid et al. |
| 10,624,861 B2 | 4/2020 | Widenhouse et al. |
| 10,667,808 B2 | 6/2020 | Baxter, III et al. |
| 10,709,452 B2 | 7/2020 | DiNardo et al. |
| 10,765,426 B2 | 9/2020 | Shelton, IV et al. |
| 10,856,866 B2 * | 12/2020 | Shelton, IV ......... A61B 17/068 |
| 10,869,663 B2 | 12/2020 | Shelton, IV et al. |
| 10,945,731 B2 | 3/2021 | Baxter, III et al. |
| 10,966,722 B2 | 4/2021 | Shelton, IV et al. |
| 10,980,539 B2 * | 4/2021 | Harris ................. A61B 17/068 |
| 10,987,102 B2 | 4/2021 | Gonzalez et al. |
| 11,006,954 B2 | 5/2021 | Landgrebe et al. |
| 11,033,266 B2 | 6/2021 | Jones et al. |
| 11,058,425 B2 | 7/2021 | Widenhouse et al. |
| 11,202,633 B2 | 12/2021 | Harris et al. |
| 11,219,451 B2 | 1/2022 | Shelton, IV et al. |
| 11,432,815 B2 | 9/2022 | Courtwright et al. |
| 11,504,115 B2 | 11/2022 | Shelton, IV et al. |
| 11,660,093 B2 | 5/2023 | Bakos et al. |
| 11,672,538 B2 * | 6/2023 | Baril ................ A61B 17/07292 227/175.1 |
| 2006/0025816 A1 * | 2/2006 | Shelton ............ A61B 17/07207 606/215 |
| 2006/0173470 A1 | 8/2006 | Oray et al. |
| 2008/0314960 A1 * | 12/2008 | Marczyk ............... A61B 17/105 606/220 |
| 2012/0080336 A1 | 4/2012 | Shelton, IV et al. |
| 2012/0145767 A1 * | 6/2012 | Shah ................ A61B 17/07207 227/176.1 |
| 2012/0228360 A1 * | 9/2012 | Hodgkinson ...... A61B 17/3211 227/176.1 |
| 2013/0153634 A1 * | 6/2013 | Carter ................ A61B 17/1155 227/176.1 |
| 2013/0256373 A1 | 10/2013 | Schmid et al. |
| 2014/0224857 A1 | 8/2014 | Schmid |
| 2015/0196296 A1 * | 7/2015 | Swayze ............ A61B 17/07207 227/176.1 |
| 2015/0245835 A1 * | 9/2015 | Racenet ........... A61B 17/07292 156/298 |
| 2016/0278774 A1 * | 9/2016 | Shelton, IV ..... A61B 17/07207 |
| 2020/0214706 A1 | 7/2020 | Vendely et al. |
| 2022/0079579 A1 | 3/2022 | Shelton, IV et al. |
| 2023/0139479 A1 | 5/2023 | Seow et al. |
| 2023/0140285 A1 | 5/2023 | Boudreaux |

OTHER PUBLICATIONS

International Search Report and Written Opinion dated Jan. 5, 2023 for Application No. PCT/IB2022/060268, 13 pgs.
International Search Report and Written Opinion dated Jan. 5, 2023 for Application No. PCT/IB2022/060272, 15 pgs.
International Search Report and Written Opinion dated Jan. 5, 2023 for Application No. PCT/IB2022/060274, 16 pgs.

* cited by examiner

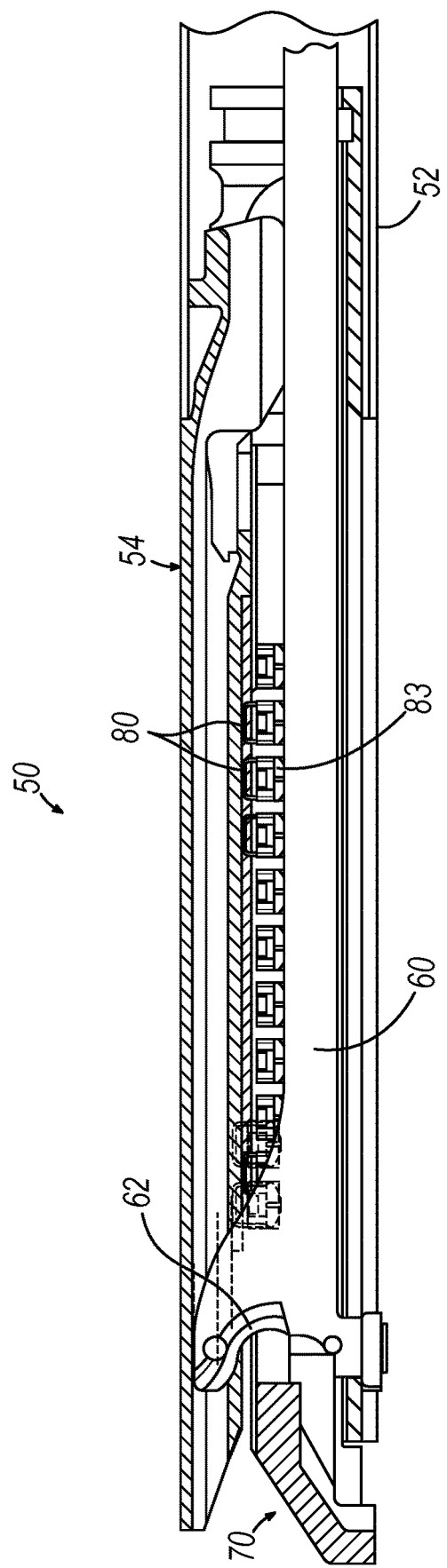

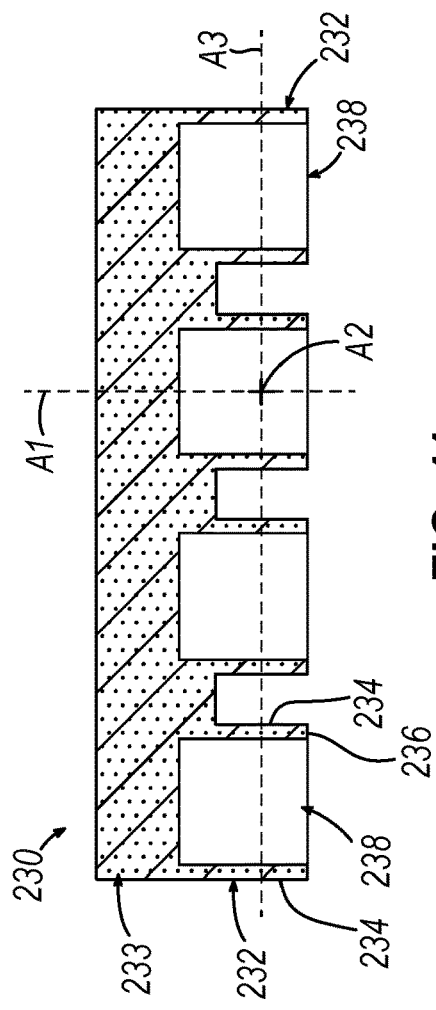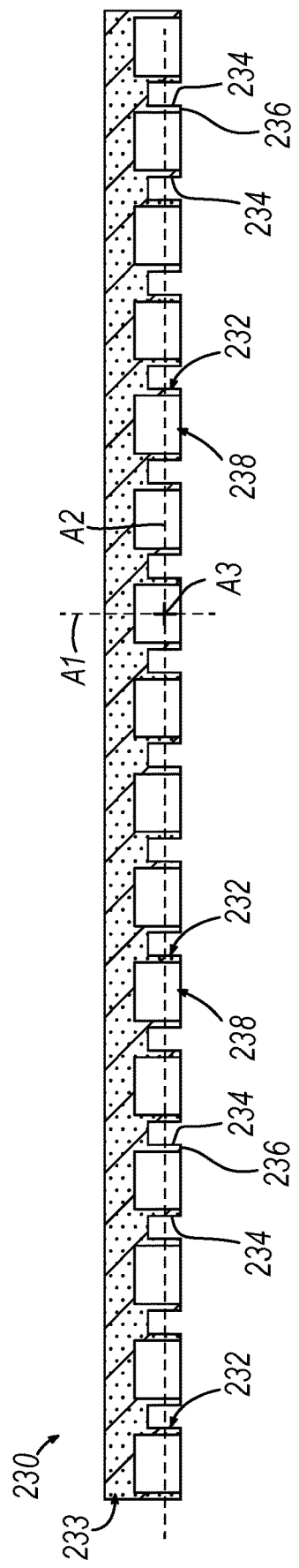

DISCRETE ADJUNCT ATTACHMENT FEATURES FOR SURGICAL STAPLER

BACKGROUND

In some surgical settings, endoscopic surgical instruments may be preferred over traditional open surgical devices in order to make use of a smaller incision in the patient, which may reduce post-operative recovery time and complications. Some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 7,380,696, entitled "Articulating Surgical Stapling Instrument Incorporating a Two-Piece E-Beam Firing Mechanism," issued Jun. 3, 2008; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. patents and U.S. patent Publications is incorporated by reference herein.

Surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 5B depicts a side cross-sectional view of the end effector of FIG. 3, taken along line 5-5 of FIG. 3, with the firing member in a distal position;

FIG. 11 depicts a cross-sectional end view of the adjunct of FIG. 10, taken along line 11-11 of FIG. 10;

FIG. 12 depicts a cross-sectional side view of the adjunct of FIG. 10, taken along line 12-12 in FIG. 10;

Figure 1:
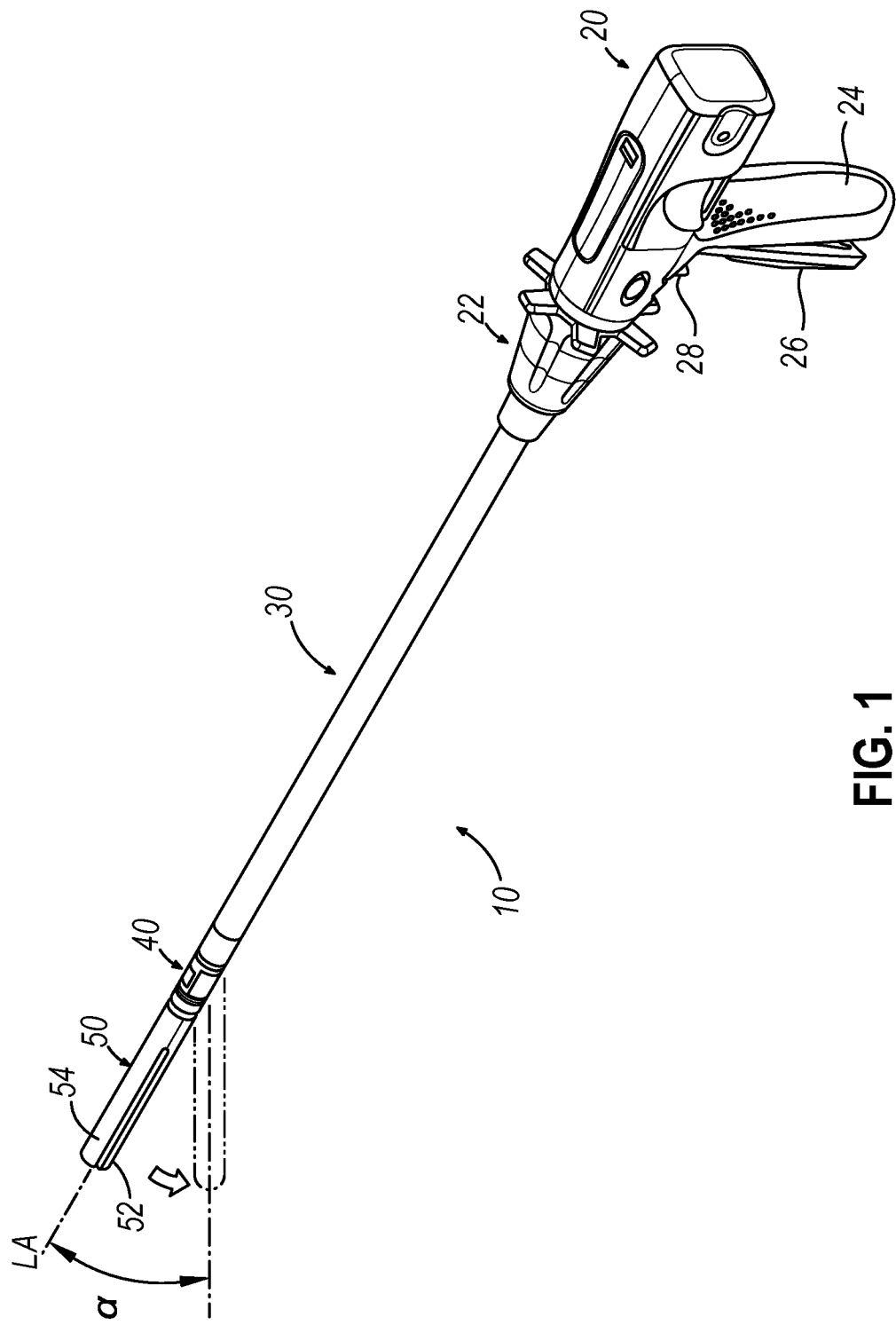
FIG. 1 depicts a perspective view of an exemplary surgical stapler.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

I. Exemplary Surgical Stapler

Figure 2:
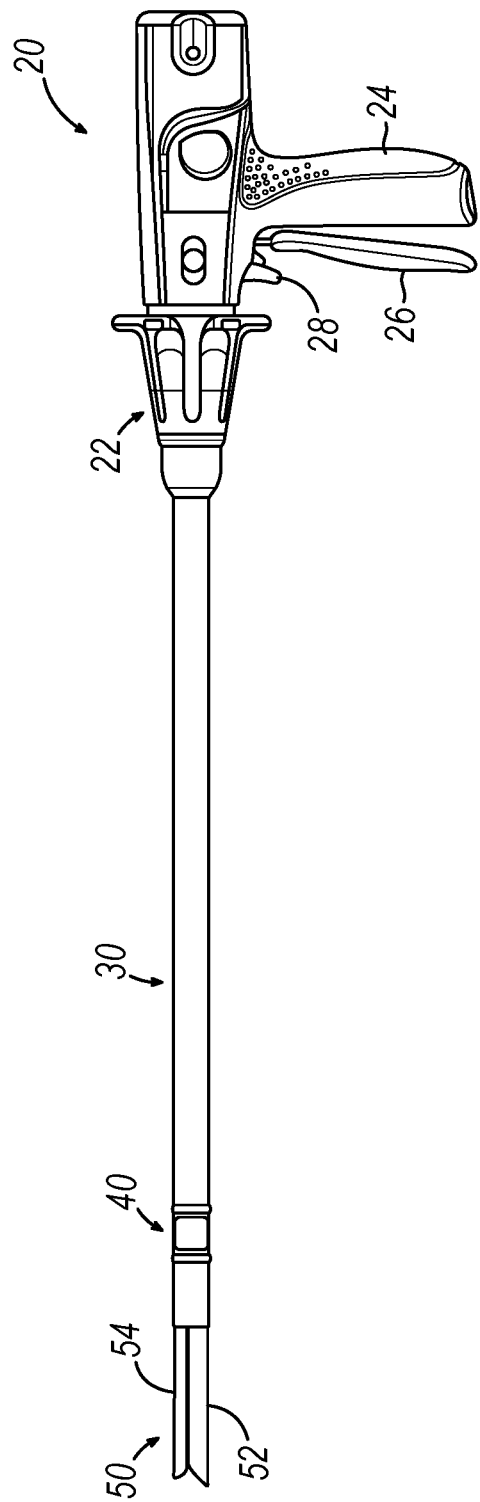
FIG. 2 depicts a side elevational view of the surgical stapler of FIG. 1.

FIGS. 1-6 show an exemplary surgical stapler (10) that is sized for insertion through a trocar cannula or an incision (e.g., thoracotomy, etc.) to a surgical site in a patient for performing a surgical procedure. As shown in FIGS. 1 and 2, surgical stapler (10) of the present example includes a proximal body in the form of a handle assembly (20), a shaft assembly (30) extending distally from handle assembly (20) and terminating at an articulation joint (40), and an end effector (50) coupled with the distal end of shaft assembly (30) via articulation joint (40). Articulation joint (40) is configured to enable lateral deflection, either actively or passively, of end effector (50) relative to a longitudinal axis (LA) of shaft assembly (30) to a desired angle (a) via actuation of an articulation control feature (22) of handle assembly (20).

Figure 3:
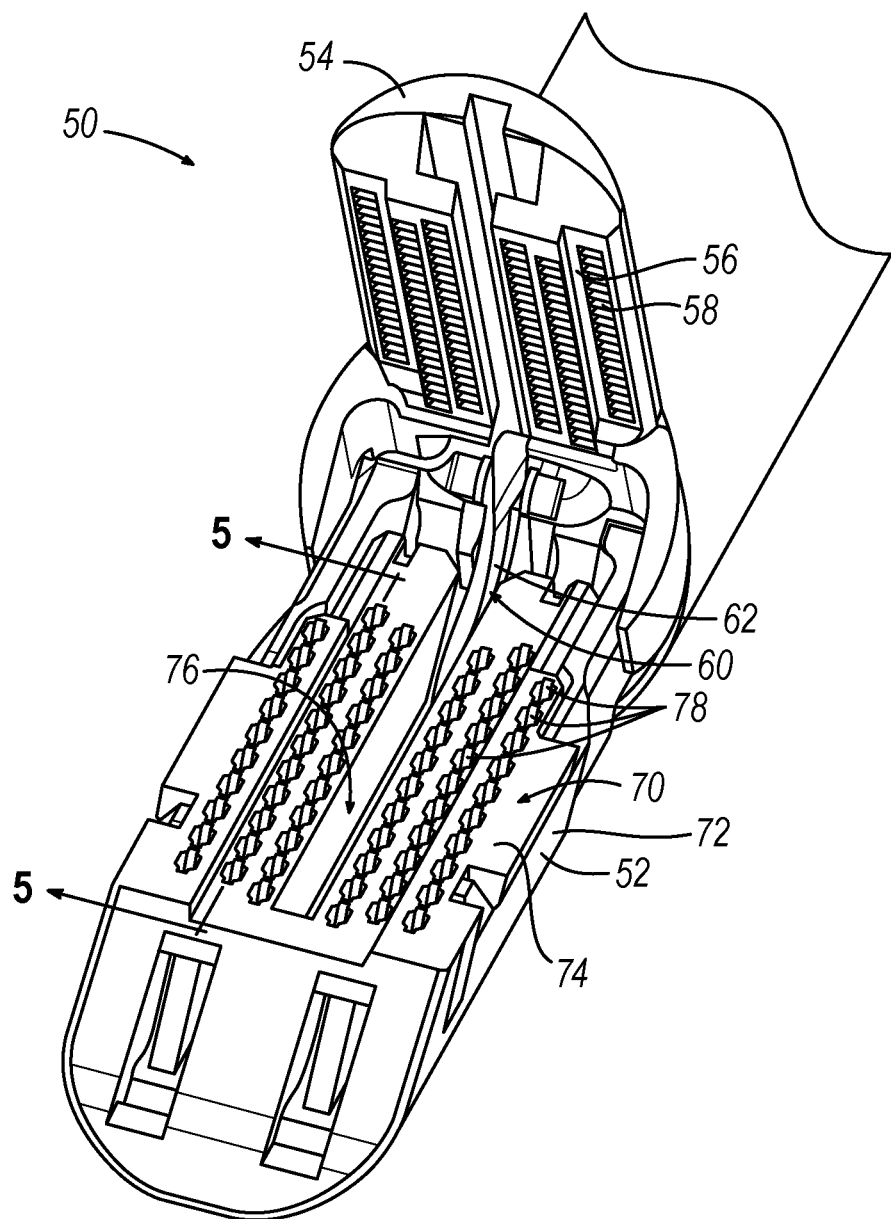
FIG. 3 depicts a perspective view of an end effector of the surgical stapler of FIG. 1 in an open state.
Figure 4:
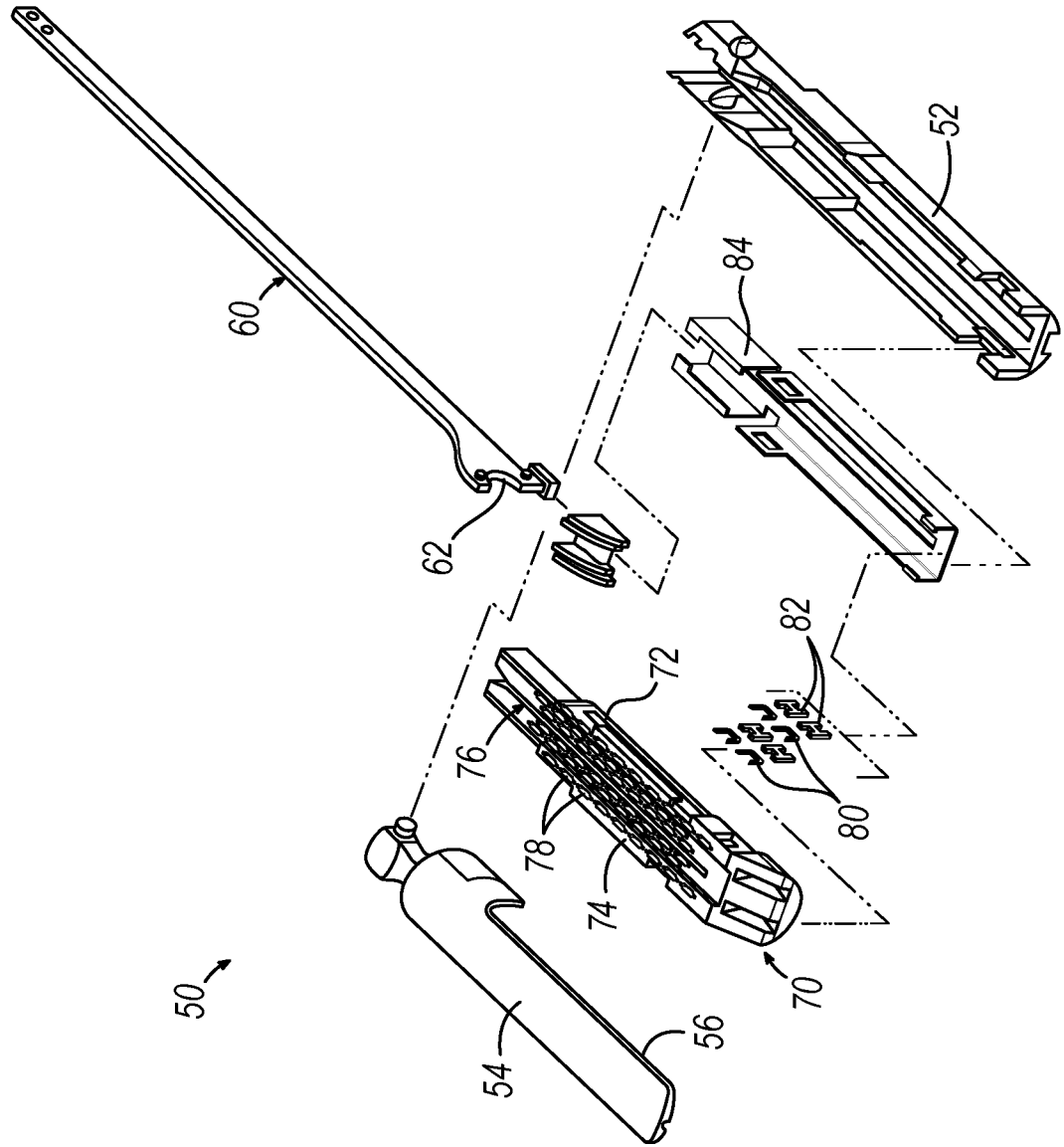
FIG. 4 depicts an exploded perspective view of the end effector of FIG. 3.

As shown best in FIGS. 3 and 4, end effector (50) includes a lower jaw (52) that supports a stapling assembly in the form of a replaceable staple cartridge (70) having a first stapling surface, and an upper jaw (54) that presents an anvil (56) having a second stapling surface with a plurality of staple forming pockets (58). Upper jaw (54) is configured to pivot relative to lower jaw (52) to clamp tissue between the stapling surfaces of staple cartridge (70) and anvil (56) and subsequently form staples deployed by staple cartridge (70). End effector (50) further includes an elongate firing member (60) configured to translate distally through end effector (50) to drive staples from staple cartridge (70) toward anvil (56) and simultaneously cut tissue with a distally presented cutting edge (62). Accordingly, end effector (50) is operable to clamp, staple, and cut tissue.

As shown best in FIGS. 1 and 2, handle assembly (20) further includes a pistol grip (24), a closure trigger (26), and a firing trigger (28). Closure trigger (26) is pivotable toward pistol grip (24) to pivotably actuate upper jaw (54) toward lower jaw (16) and thereby close end effector (50) on tissue. Firing trigger (28) is then pivotable toward pistol grip (24) to fire end effector (50) on the clamped tissue. More specifically, actuation of firing trigger (28) causes firing member (60) to translate distally through end effector (50), including staple cartridge (70), to thereby staple and simultaneously cut the clamped tissue.

As shown in FIGS. 3-5B, staple cartridge (70) includes a cartridge body (72) having an upwardly facing deck (74), an elongate slot (76) extending along a central axis of cartridge body (72) and opening upwardly through deck (74), and a plurality of staple openings (78) (also known as apertures) extending through deck (74) on each side of elongate slot (76). Each staple opening (78) slidably houses an unformed staple (80) and a respective staple driver (82) positioned beneath staple (80). A lower tray (84), also known as a pan, encloses an underside of cartridge body (72) and thereby retains staples (80) and staple drivers (82) within cartridge body (72). A wedge sled (86) is slidably disposed within cartridge body (72) and includes upwardly presented cam surfaces configured to engage the undersides of staple drivers (82).

Figure 5A:
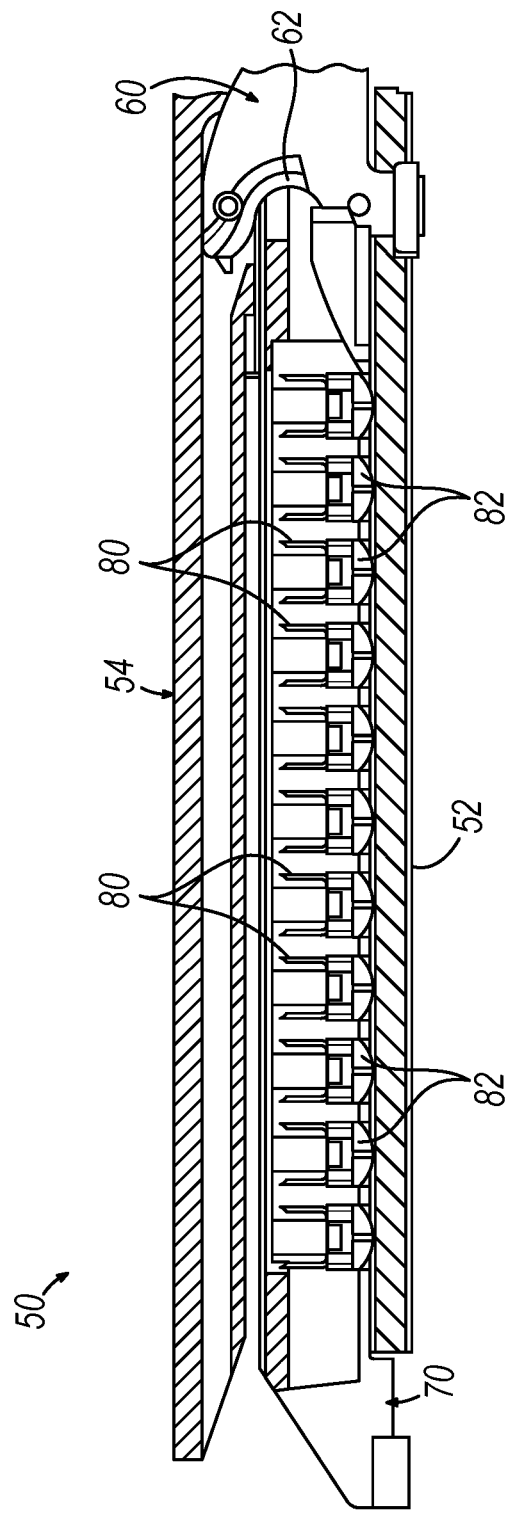
FIG. 5A depicts a side cross-sectional view of the end effector of FIG. 3, taken along line 5-5 of FIG. 3, with a firing member in a proximal position.

FIGS. 5A-5B show a firing stroke of surgical stapler (10) during which firing member (60) is actuated distally through end effector (50), including elongate slot (76) of staple cartridge (70). A distal end of firing member (60) drives wedge sled (86) distally to cam staple drivers (82) upwardly and thereby drive the respective staples (80) outwardly from staple openings (78). The legs of staples (80) pass through clamped tissue (not shown) and are then formed by staple forming pockets (58) of anvil (56) (see FIG. 3). Simultaneously, the clamped tissue is severed by cutting edge (62) of firing member (60).

Figure 6:
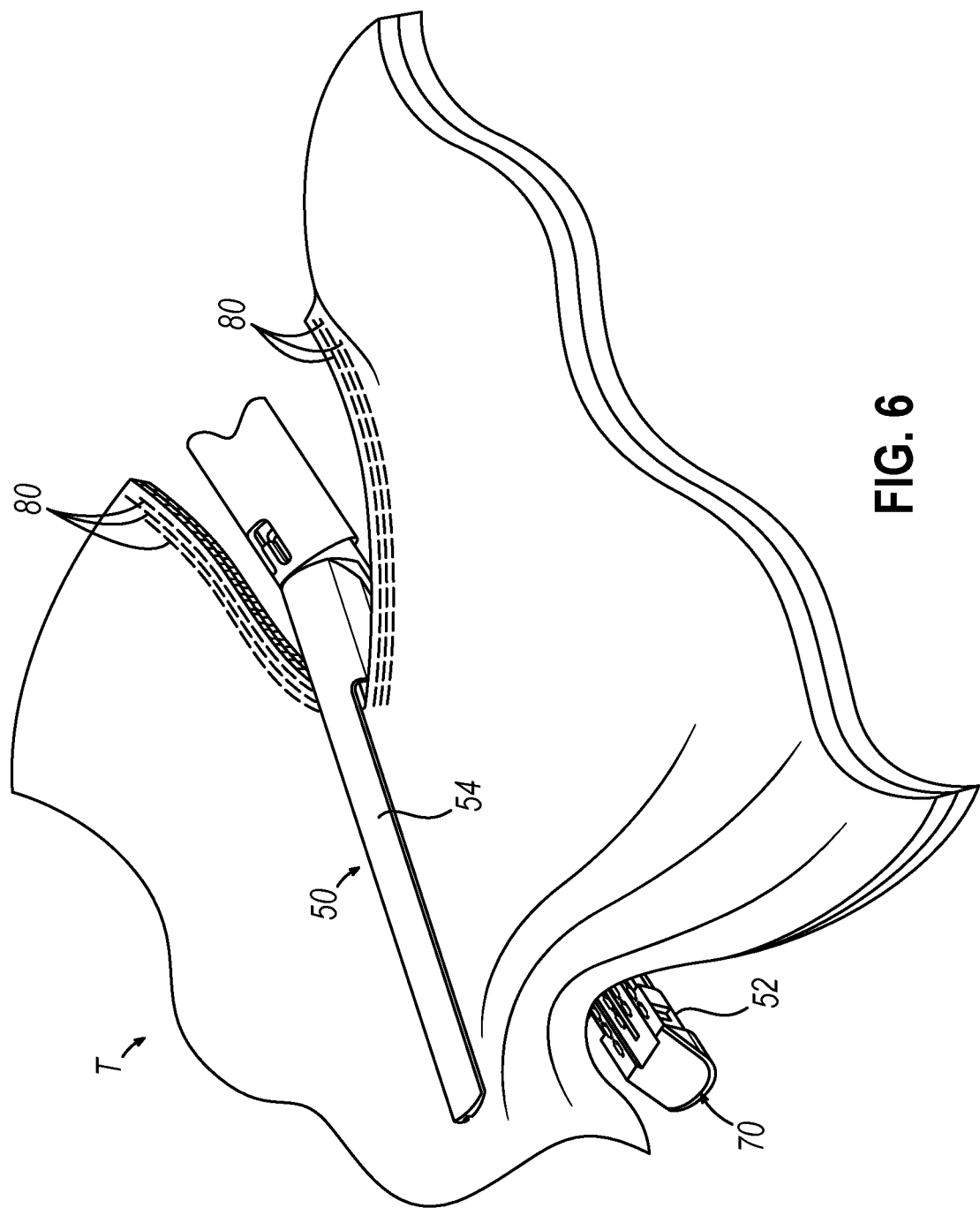
FIG. 6 depicts a perspective view of the end effector of FIG. 3, positioned at tissue and having been fired once in the tissue.

FIG. 6 shows end effector (50) after having been actuated through a single firing stroke through tissue (T). Cutting edge (62) of firing member (60) has cut through tissue (T), and staple drivers (82) have driven three alternating rows of staples (80) through tissue (T) on each side of the cut line produced by cutting edge (62). After the first firing stroke is completed, end effector (50) is withdrawn from the patient, spent staple cartridge (70) is replaced with a new staple cartridge (70), and end effector (50) is then again inserted into the patient to reach the stapling site for further cutting and stapling. This process may be repeated until the desired quantity and pattern of firing strokes across the tissue (T) has been completed.

Surgical stapler (10) may be further constructed and operable in accordance with any of the teachings of the following references, the disclosures of which are incorporated by reference herein: U.S. Pat. No. 8,210,411, entitled "Motor-Driven Surgical Instrument," issued Jul. 3, 2012; U.S. Pat. No. 9,186,142, entitled "Surgical Instrument End Effector Articulation Drive with Pinion and Opposing Racks," issued on Nov. 17, 2015; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; U.S. Pat. No. 9,717,497, entitled "Lockout Feature for Movable Cutting Member of Surgical Instrument," issued Aug. 1, 2017; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 9,839,421, entitled "Jaw Closure Feature for End Effector of Surgical Instrument," issued Dec. 12, 2017; and/or U.S. Pat. No. 10,092,292, entitled "Staple Forming Features for Surgical Stapling Instrument," issued Oct. 9, 2018.

II. Exemplary Buttress Assembly

In some instances, it may be desirable to equip end effector (50) of surgical stapler (10) with an adjunct, also known as a buttress or a tissue thickness compensator, to reinforce the mechanical fastening of tissue provided by staples (80). Such a buttress may prevent the applied staples (80) from pulling through the tissue and may otherwise reduce a risk of tissue tearing at or near the site of applied staples (80). In addition to or as an alternative to providing structural support and integrity to a line of staples (80), a buttress may provide various other kinds of effects such as spacing or gap-filling, administration of therapeutic agents, and/or other effects. In some instances, a buttress may be provided on upper deck (74) of staple cartridge (70). In some other instances, a buttress may be provided on the surface of anvil (56) that faces staple cartridge (70). It should also be understood that a first buttress may be provided on upper deck (74) of staple cartridge (70) while a second buttress is provided on anvil (56) of the same end effector (50).

A. Exemplary Composition of Buttress Assembly

Figure 7:
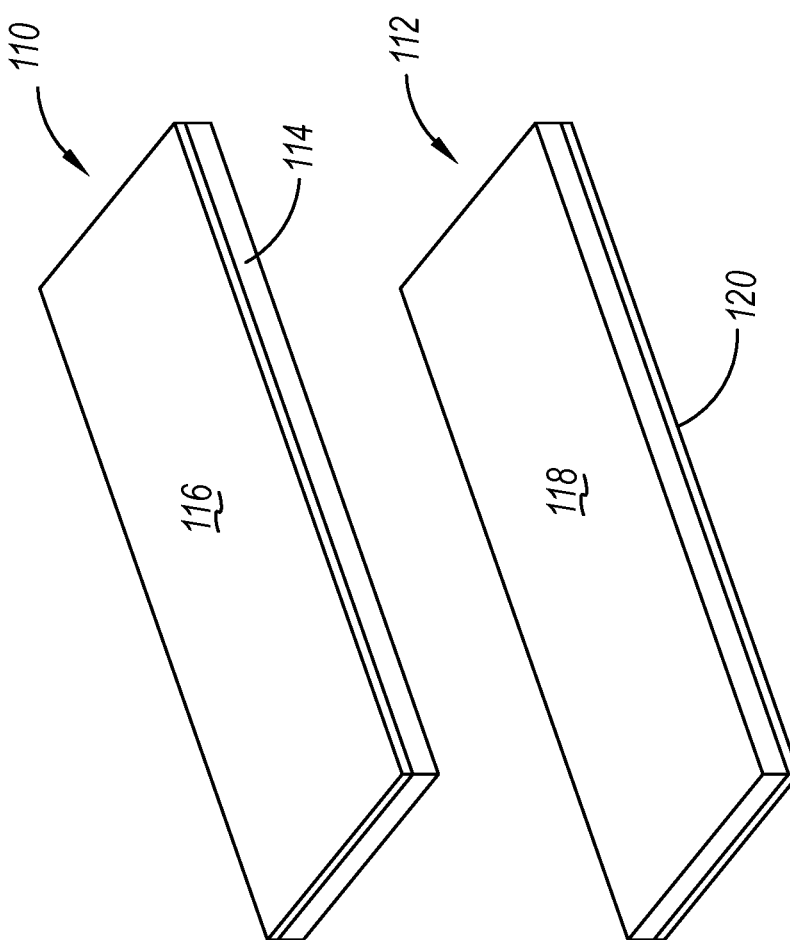
FIG. 7 depicts a perspective view of an exemplary pair of adjuncts in the form of buttress assemblies, each of which may be applied to a jaw of the end effector of FIG. 3.

FIG. 7 shows an exemplary pair of adjuncts in the form of buttress assemblies (110, 112) (each also referred to individually as a "buttress"). Buttress assembly (110) of this example comprises a buttress body (114) and an upper adhesive layer (116). Similarly, buttress assembly (112) comprises a buttress body (118) and a lower adhesive layer (120). In the present example, each buttress body (114, 118) comprises a strong yet flexible material configured to structurally support a line of staples (80). By way of example only, each buttress body (114, 118) may comprise a mesh of polyglactin 910 material by Ethicon, Inc. of Somerville, New Jersey. Alternatively, any other suitable materials or combinations of materials may be used in addition to or as an alternative to polyglactin 910 material to form each buttress body (114, 118).

Each buttress body (114, 118) may comprise a material including, for example, a hemostatic agent such as fibrin to assist in coagulating blood and reduce bleeding at the severed and/or stapled surgical site along tissue ($T_1$, $T_2$). As another merely illustrative example, each buttress body (114, 118) may comprise other adjuncts or hemostatic agents such as thrombin may be used such that each buttress body (114, 118) may assist to coagulate blood and reduce the amount of bleeding at the surgical site. Other adjuncts or reagents that may be incorporated into each buttress body (114, 118) may further include but are not limited to medical fluid or matrix components.

In the present example, adhesive layer (116) is provided on buttress body (114) to adhere buttress body (114) to an underside (124) of anvil (56). Similarly, adhesive layer (120) is provided on buttress body (118) to adhere buttress body (118) to upper deck (74) of staple cartridge (70). Such an adhesive material may provide proper positioning of buttress body (114, 118) before and during actuation of end effector (50); then allow buttress body (114, 118) to separate from end effector (50) after end effector (50) has been actuated, without causing damage to buttress body (114, 118) that is substantial enough to compromise the proper subsequent functioning of buttress body (114, 118).

B. Exemplary Stapling of Tissue with Buttress Assemblies

Figure 8C:
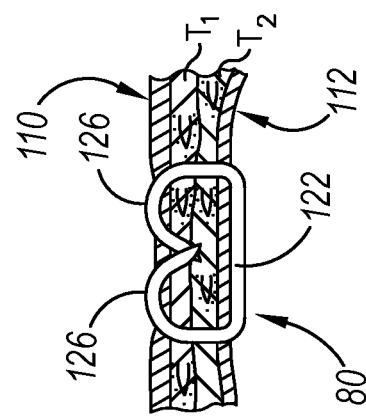
FIG. 8C depicts a cross-sectional view of a formed staple and the buttress assemblies of FIG. 8A after having been secured to the tissue by the end effector of FIG. 3.
Figure 8B:
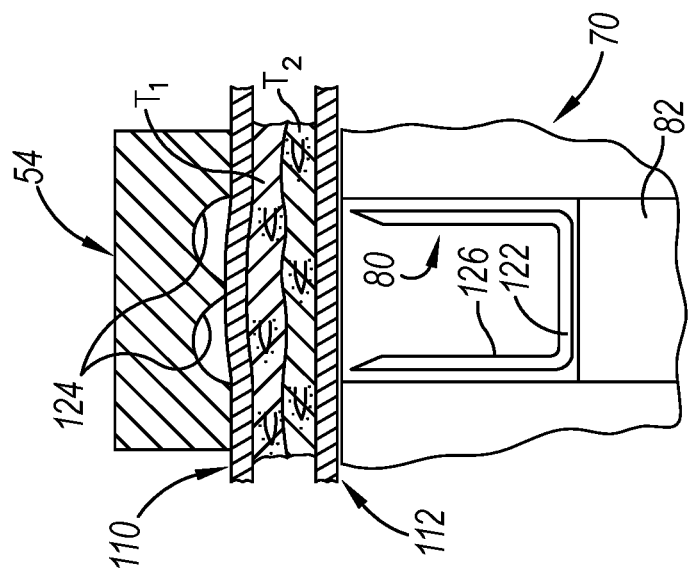
FIG. 8B depicts a cross-sectional end view of the end effector and buttress assemblies of FIG. 8A, showing the end effector jaws in a closed state on the tissue.
Figure 8A:
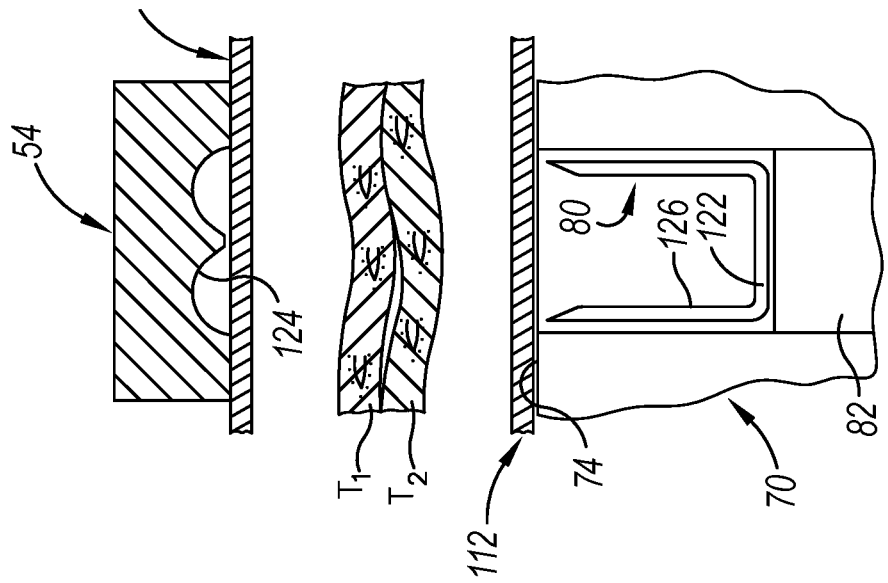
FIG. 8A depicts a cross-sectional end view of a portion of the end effector of FIG. 3 with the buttress assemblies of FIG. 7 applied to the upper and lower jaws of the end effector, showing the end effector jaws in an open state with tissue positioned between the upper and lower jaws.

FIGS. 8A-8C show an exemplary sequence in which surgical stapler end effector (50), which has been loaded with buttress assemblies (110, 112), is actuated to drive staples (80) through two opposed layers of tissue ($T_1$, $T_2$), with buttress assemblies (110, 112) being secured to the same layers of tissue ($T_1$, $T_2$) by staples (80). In particular, FIG. 8A shows layers of tissue ($T_1$, $T_2$) positioned between anvil (56) and staple cartridge (70), with anvil (56) in the open position. Buttress assembly (110) is adhered to underside (124) of anvil (56) via adhesive layer (116); while buttress assembly (112) is adhered to upper deck (74) of staple cartridge (70) via adhesive layer (120). Layers of tissue ($T_1$, $T_2$) are thus interposed between buttress assemblies (110, 112). Next, anvil (56) is closed against staple cartridge (70) such that layers of tissue ($T_1$, $T_2$) are compressed between anvil (56) and staple cartridge (70), with buttress assemblies (110, 112) engaging opposite surfaces of tissue layers ($T_1$, $T_2$). End effector (50) is then fired as described above, driving staple (80) through buttress assemblies (110, 112) and tissue ($T_1$, $T_2$). As shown in FIG. 8C, a crown (122) of driven staple (80) captures and retains buttress assembly (112) against layer of tissue ($T_2$). Deformed legs (126) of staple (80) capture and retain buttress assembly (110) against layer of tissue ($T_1$).

Figure 9:
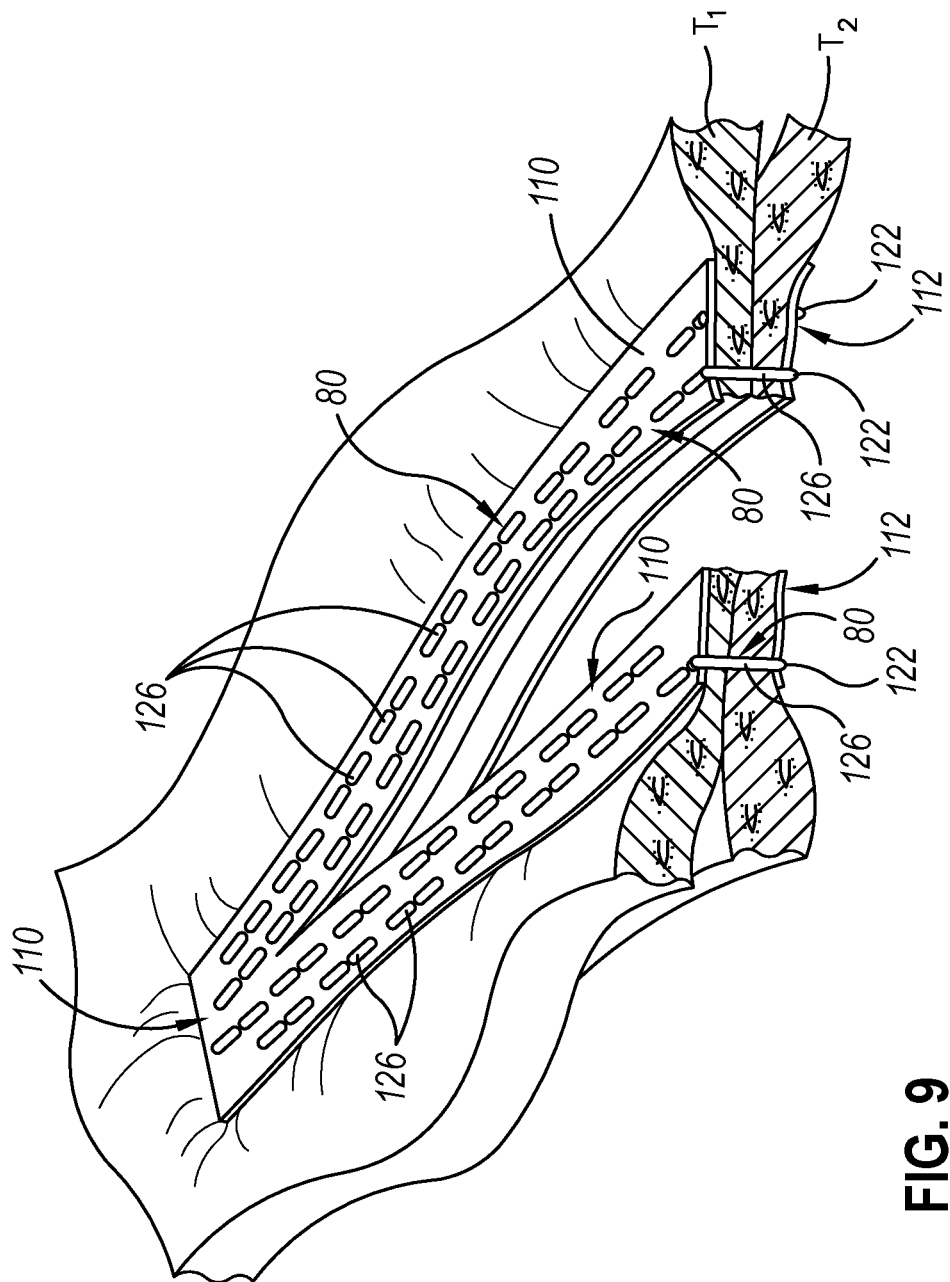
FIG. 9 depicts a perspective view of formed staples and the buttress assemblies of FIG. 8A after having been secured to the tissue by the end effector of FIG. 3.
Figure 10:
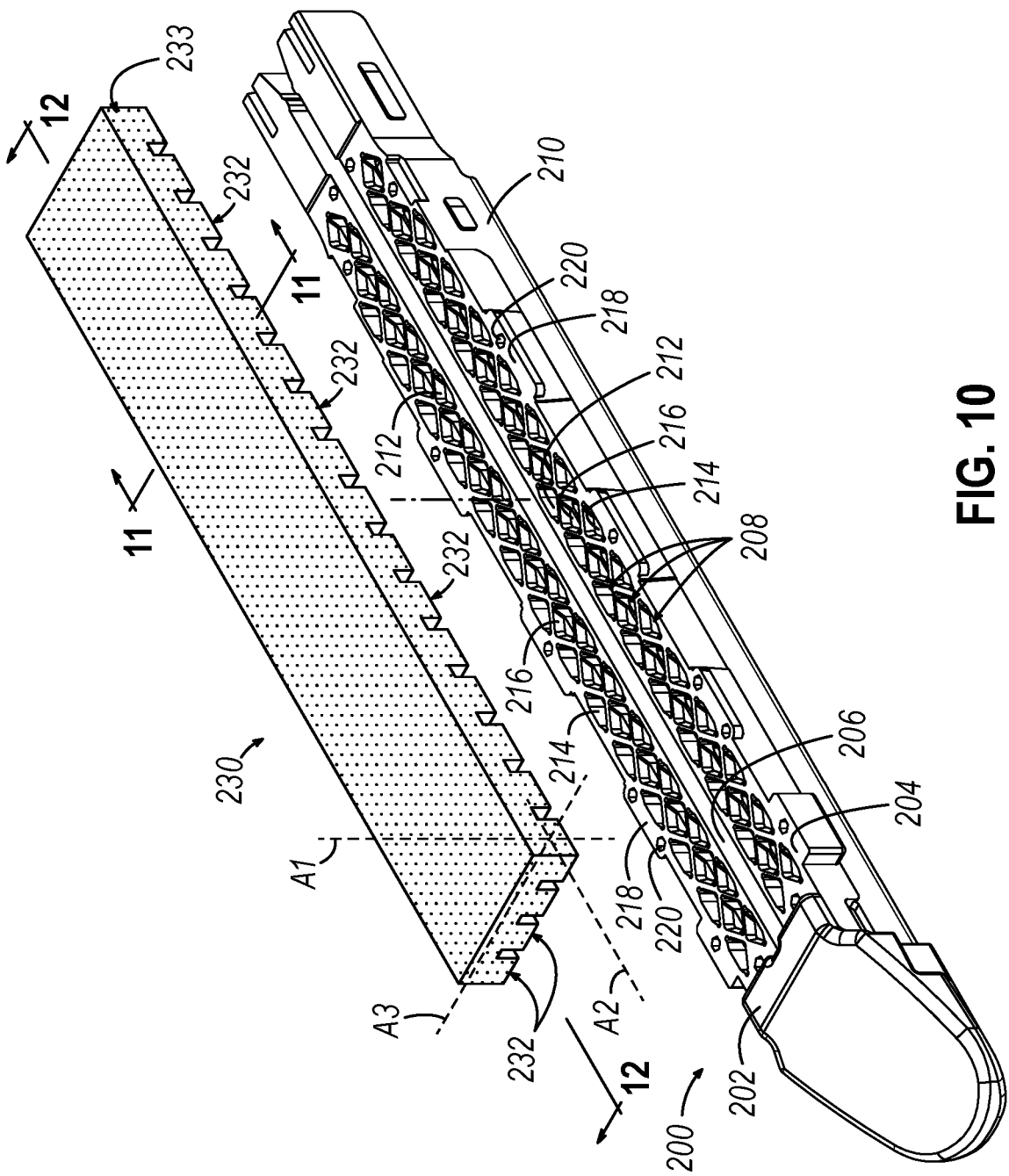
FIG. 10 depicts a perspective view of another exemplary staple cartridge in combination with another exemplary adjunct.

A series of staples (80) similarly capture and retain buttress assemblies (110, 112) against layers of tissue ($T_1$, $T_2$), thereby securing buttress assemblies (110, 112) to tissue ($T_1$, $T_2$) as shown in FIG. 10. As end effector (50) is pulled away from tissue ($T_1$, $T_2$) after deploying staples (80) and buttress assemblies (110, 112), buttress assemblies (110, 112) disengage end effector such that buttress assemblies (110, 112) remain secured to tissue ($T_1$, $T_2$) with staples (80). Buttress assemblies (110, 112) thus provide structural reinforcement to the lines of staples (80) formed in tissue ($T_1$, $T_2$). As can also be seen in FIG. 9, distally presented cutting edge (62) of firing member (60) also cuts through a centerline of buttress assemblies (110, 112), separating each buttress assembly (110, 112) into a corresponding pair of sections, such that each section remains secured to a respective severed region of tissue ($T_1$, $T_2$).

During use, surgical instrument (10) may be actuated multiple times during a single surgical procedure such that it may be desirable to enable an operator to repeatedly and easily load buttress assemblies (110, 112) onto lower jaw and anvil (16, 18) during that single surgical procedure. Accordingly, it may be desirable to use an adjunct applicator, also referred to as a buttress applier cartridge, to apply buttress assemblies (110, 112) to lower jaw and anvil (16, 18). Exemplary versions of such an applicator are disclosed in U.S. patent application Ser. No. 17/022,520, entitled "Method of Applying Buttress to End Effector of Surgical Stapler," filed Sep. 16, 2020, issued May 30, 2023 as U.S. Pat. No. 11,660,093, the disclosure of which is incorporated by reference herein.

It will be appreciated that exemplary adjuncts and adjunct applicators may be further configured in accordance with one or more teachings of U.S. Pat. No. 10,166,023, entitled "Method of Applying a Buttress to a Surgical Stapler End Effector," issued Jan. 1, 2019; U.S. Pat. No. 10,349,939, entitled "Method of Applying a Buttress to a Surgical Stapler," issued Jul. 16, 2019; and U.S. Pat. Pub. No. 2012/0080336, entitled "Staple Cartridge Comprising Staples Positioned Within a Compressible Portion Thereof," published Apr. 5, 2012, now abandoned, the disclosures of which are incorporated by reference herein.

III. Exemplary Compressible Adjunct

In some instances, it may be desirable to employ an adjunct having an enhanced degree of compressibility in a direction orthogonal to the stapling surfaces of end effector (50). Such an adjunct may be configured to apply a compression spring force to stapled tissue consistently along the entire length of the formed staple pattern, thereby ensuring a secure seal of tissue having a thickness that varies along a length of the formed staple pattern and end effector (50). FIGS. 10-12 show an example of such an adjunct (230), also referred to herein as a buttress or cushion, in combination with a staple cartridge (200). Staple cartridge (200) and adjunct (230) are configured for use with end effector (50) and are similar to staple cartridge (70) and buttress assembly (110, 112) described above except as otherwise described below.

It will be appreciated that staple cartridge (200) and/or adjunct (230) may be further configured in accordance with the teachings of any one or more of the following references, the disclosures of which are incorporated by reference herein: U.S. Pat. No. 10,441,285, entitled "Tissue Thickness Compensator Comprising Tissue Ingrowth Features," issued Oct. 15, 2019; U.S. Pat. No. 10,524,788, entitled "Compressible Adjunct with Attachment Regions," issued Jan. 7, 2020; U.S. Pat. No. 10,568,621, entitled "Surgical Staple Buttress with Integral Adhesive for Releasably Attaching to a Surgical Stapler," issued Feb. 25, 2020; U.S. Pat. No. 10,588,623, entitled "Adhesive Film Laminate," issued Mar. 17, 2020; U.S. Pat. No. 10,624,861, entitled "Tissue Thickness Compensator Configured to Redistribute Compressive Forces," issued Apr. 21, 2020; U.S. Pat. No. 10,667,808, entitled "Staple Cartridge Comprising an Absorbable Adjunct," issued Jun. 2, 2020; U.S. Pat. No. 10,945,731, entitled "Tissue Thickness Compensator Comprising Controlled Release and Expansion," issued Mar. 16, 2021; U.S. Pat. No. 10,966,722, entitled "Adjunct Materials and Methods of Using Same in Surgical Methods for Tissue Sealing," issued Apr. 6, 2021; U.S. Pat. No. 11,058,425, entitled "Implantable Layers for a Surgical Instrument," issued Jul. 13, 2021; and U.S. Pat. Pub. No. 2019/0200978, entitled "Tissue Ingrowth Materials and Method of Using the Same," published Jul. 4, 2019, issued Jan. 11, 2022 as U.S. Pat. No. 11,219,451.

As shown in FIG. 10, staple cartridge (200) includes a cartridge body (202) having an upwardly facing deck (204), an elongate slot (206) extending along a central axis of cartridge body (202) and opening upwardly through deck (204), and a plurality of staple openings (208) extending through deck (204) on each side of elongate slot (206). Each staple opening (208) slidably houses an unformed staple (not shown), similar to staple (80), and a respective staple driver (not shown), similar to staple driver (82), configured to drive the staple outwardly toward anvil (56) to be formed. A lower tray (210) of staple cartridge (200) retains the staples and staple drivers within cartridge body (202).

Cartridge body (202) of the present example further includes a plurality of upwardly-opening recesses (212, 214, 216) formed in deck (204) and having base surfaces through which staple openings (208) extend. More specifically, on each side of elongate slot (206), deck (204) includes an inner row of triangular recesses (212) each having a medial apex that points transversely away from elongate slot (206); an outer row of triangular recesses (214) each having a medial apex that points transversely toward elongate slot (206); and a middle row of diamond-shaped recesses (216) each having an inner medial apex that points transversely toward elongate slot (206) and an opposed outer medial apex that points transversely away from elongate slot (206). Recesses (212, 214, 216) may cooperate to more securely grip and thereby stabilize clamped tissue during stapling and cutting of the clamped tissue.

Cartridge body (202) of the present example further includes a plurality of elongate tabs (218) projecting laterally outwardly from deck (204) on each lateral side of cartridge body (202). Tabs (218) of the present example are spaced apart from one another in a longitudinal direction, and each tab (218) has a generally rounded rectangular shape. Cartridge body (202) further includes a plurality of attachment openings (220) spaced apart from one longitudinally on each side of elongate slot (206), with each attachment opening (220) being smaller than a staple opening (208) and having a hexagonal shape. In the present version, each tab (218) includes at least one attachment opening (220). Attachment openings (220) may be configured to facilitate releasable attachment of an adjunct, such as adjunct (230), to staple cartridge deck (204).

Adjunct (230) has a plurality of sub-structures in the form of three-dimensional, resiliently compressible (or collapsible) nodules (232) that define a lower portion of adjunct (230) and are integrally connected with one another, via an upper portion (233) of adjunct (230), in a plurality of linear arrays defining a lattice structure having an elongate rectangular shape. In the present example, adjunct (230) includes four axial rows of nodules (232) each extending in a proximal-distal direction to define a length of adjunct (230), and sixteen transverse rows of nodules (232) each extending in a direction transverse to a length of staple cartridge (200) to define a transverse width of adjunct (230). It will be appreciated that adjunct (230) of other versions may have various other quantities and configurations of nodules (232).

Each nodule (232) of the present example has a generally cuboid shape defining four side surfaces (234), a lower surface (236), and an opening (238) in lower surface (236) that extends along a vertical central axis (A1) of nodule (232) and defines an open, hollow interior of nodule (232). Additionally, each nodule (232) is symmetrical about its centroid along a second axis (A2) of nodule (232) that extends horizontally in a proximal-distal direction parallel to the length of adjunct (230), and along a third axis (A3) of nodule (232) that extends horizontally in a direction traverse to the length of adjunct (230), where each axis (A1, A2, A3) extends through the centroid. It will be appreciated that nodules (232) may be alternatively shaped in other versions of adjunct (230). Though not shown, in some versions one or more of side surfaces (234) of each nodule (232) may include an opening that communicates with the hollow interior of the nodule (232). Additionally, in some versions, adjacent nodules (232) may be interconnected at side surfaces (234) by connecting structures, which may define respective lumens between the hollow interiors of adjacent nodules (232).

Adjunct (230) may be formed of an elastic, bioabsorbable polymeric material having a suitable degree of elasticity that enables adjunct (230) to compress and resiliently resume its original shape. In the present example, each nodule (232) of adjunct (230) is resiliently compressible in such a manner along at least each of its three axes (A1, A2, A3). Additionally, adjunct (230) may be formed as a monolithic structure via an additive manufacturing process, for example. It will be appreciated that adjunct (230) may be further or alternatively constructed and operable in accordance with any of the other teachings made herein, and/or with the teachings of any of the patent references incorporated by reference here.

Adjunct (230) may be releasably attached to a deck of a staple cartridge, such as decks (74, 204) of staple cartridges (70, 200), via one or more attachment features, examples of which are described in greater detail below. It will be appreciated that adjunct (230) may be attached to a staple cartridge with or without an applicator device.

IV. Exemplary Features for Attaching Adjunct to Staple Cartridge

In some instances, it may be desirable to provide an adjunct with one or more features for releasably and mechanically attaching the adjunct to the deck of a staple cartridge, such as either of staple cartridges (70, 200) described above. Exemplary versions of such adjunct attachment features are described in greater detail below. Unless otherwise described, it will be appreciated that such attachment features may be applied to a multi-layer adjunct similar to buttress assemblies (110, 112) described above in connection with FIGS. 7-9, or alternatively to a compressible monolithic adjunct similar to adjunct (230) described above in connection with FIGS. 10-12. As will be described, some exemplary adjunct attachment features may be configured to release the adjunct from the deck of a staple cartridge in response to firing of the staple cartridge (referred to as "active" release). Other exemplary adjunct attachment features may be configured to release an adjunct from the deck of a staple cartridge simply in response to separation of the surgical stapler end effector from the stapled tissue (referred to as "passive" release). Additionally, unless otherwise described, it will be appreciated that any of the exemplary adjunct attachment features described below are disposed at discrete locations along a length of the corresponding adjunct, and that each such attachment feature may be constructed of a different material than the tissue contacting portion of the adjunct.

Figure 13A:
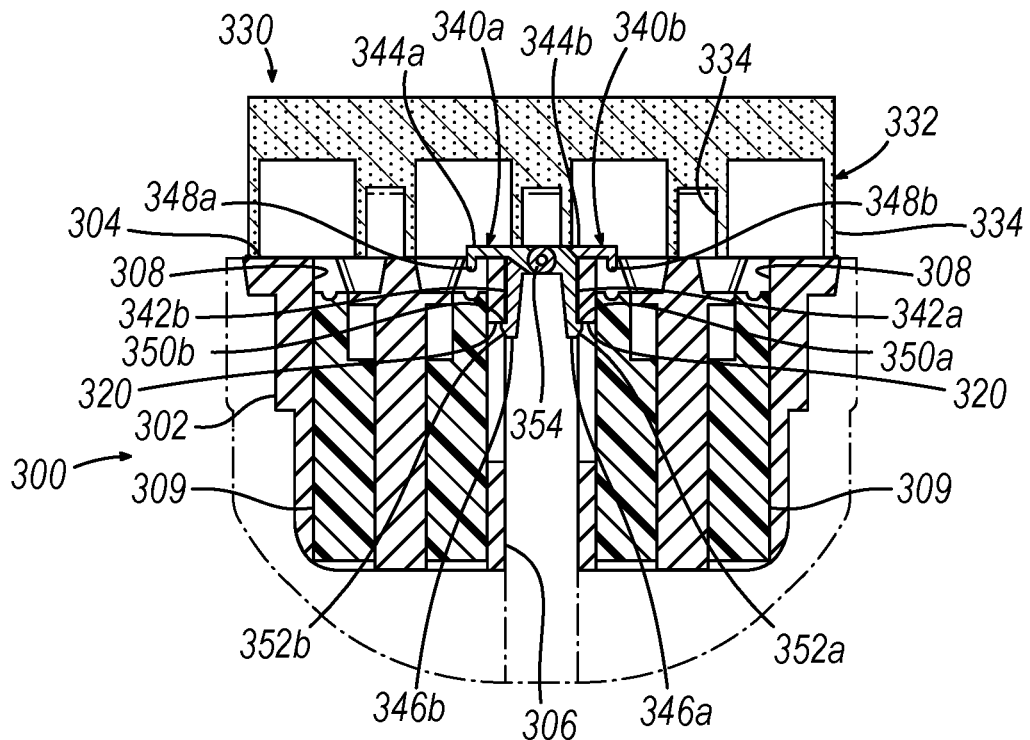
FIG. 13A depicts a cross-sectional end view of another exemplary staple cartridge in combination with another exemplary adjunct, showing hinged attachment features of the adjunct engaged with undercut features of the staple cartridge for attaching the adjunct to the staple cartridge.
Figure 13B:
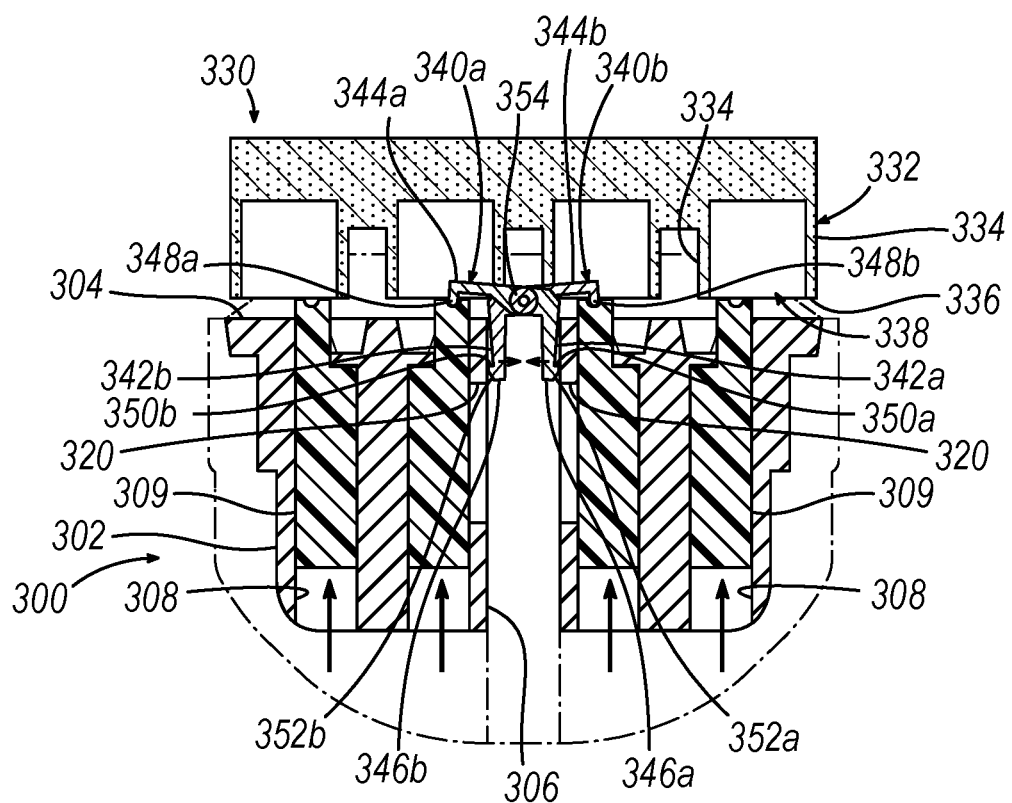
FIG. 13B depicts a cross-sectional end view of the staple cartridge and adjunct of FIG. 13A, showing staple drivers housed within the staple cartridge driven upwardly to disengage the hinged attachment features from the undercut features for releasing the adjunct from the staple cartridge.

A. Exemplary Adjunct with Hinged Attachment Features for Engaging Undercut Features of Cartridge Slot FIGS. 13A-13B show another exemplary compressible monolithic adjunct (330) configured for releasable attachment to a staple cartridge (300). Staple cartridge (300) and adjunct (330) are configured for use with end effector (50) and are similar to staple cartridge (200) and adjunct (230) described above except as otherwise described below. In this regard, staple cartridge (300) includes a cartridge body (302)

having an upwardly facing deck (304), an elongate slot (306) extending along a central axis of cartridge body (302) and opening upwardly through deck (304), and a plurality of staple openings (308) extending through deck (304) on each side of elongate slot (306). Each staple opening (308) slidably houses an unformed staple (not shown), similar to staple (80), and a respective staple driver (309) configured to drive the staple outwardly toward anvil (56) to be formed. A lower tray (not shown) of staple cartridge (300) retains the staples and staple drivers within cartridge body (302). Cartridge body (302) of the present example further includes a transversely-opposed pair of undercut surfaces (320) each positioned on a respective side of elongate slot (306) and configured to facilitate releasable attachment of an adjunct, such as adjunct (330), to staple cartridge deck (304), as described in greater detail below.

Adjunct (330) has a plurality of three-dimensional, resiliently compressible nodules (332) that are integrally connected with one another in a plurality of linear arrays defining a lattice structure having an elongate rectangular shape in a manner similar to that described above in connection with FIGS. 10-12. Each nodule (332) of the present example has a generally cuboid shape defining four side surfaces (334), a lower surface (336), and an opening (338) in lower surface (336) that extends along a vertical central axis of nodule (332) and defines an open, hollow interior of nodule (332).

In the example shown, adjunct (330) further includes a pair of attachment features in the form of hinged latches (340a, 340b) coupled to transversely-inner nodules (332) and configured to be at least partially received within elongate slot (306). Each latch (340a, 340b) includes a generally downwardly-extending beam (342a, 342b) and a lever arm (344a, 344b) extending generally transversely inwardly from an upper portion of the respective beam (342a, 342b). As shown, each latch (340a, 340b) further includes a lower detent (346a, 346b) extending generally transversely outwardly from a lower portion of the respective beam (342a, 342b) for selectively engaging a respective undercut surface (320) of cartridge body (302), and an upper detent (348a, 348b) extending generally downwardly from an outer end of the respective lever arm (344a, 344b) for selectively engaging a respective transversely-inner staple driver (309) housed within cartridge body (302). In the example shown, each lower detent (346a, 346b) includes a generally horizontally-extending abutment surface (350a, 350b) and a cam surface (352a, 352b) tapered transversely inwardly in a generally downward direction from an outer edge of the respective abutment surface (350a, 350b), the purposes of which are described below.

Lever arms (344a, 344b) of latches (340a, 340b) of the present version are pivotably coupled to each other via a hinge (354) such that latches (340a, 340b) are pivotable relative to each other about hinge (354) between a latched state (FIG. 13A) and an unlatched state (FIG. 13B). In some versions, latches (340a, 340b) may be resiliently biased toward the latched state. In addition, or alternatively, any one or more of nodules (332), latches (340a, 340b) and/or hinge (354) may be integrally formed together as a unitary piece. For example, any one or more of nodules (332), latches (340a, 340b) and/or hinge (354) may be 3D-printed together. In some versions, latches (340a, 340b) and/or hinge (354) may be constructed of a different material than that of nodules (332). In any event, latches (340a, 340b) are configured to span across elongate slot (306) such that the respective lower detent (346a, 346b) and the respective upper detent (348a, 348b) are disposed on opposite sides of elongate slot (306), with hinge (354) generally transversely centered relative to elongate slot (306).

As shown in FIG. 13A, adjunct (330) may be selectively attached to staple cartridge deck (304) via latches (340a, 340b) when latches (340a, 340b) are in the latched state. In the illustrated latched state, abutment surfaces (350a, 350b) of lower detents (346a, 346b) engage respective undercut surfaces (320) of cartridge body (302) to thereby attach adjunct (330) to staple cartridge deck (304), while upper detents (348a, 348b) are each aligned in a vertical direction with at least a portion of a transversely-inner staple driver (309) on an opposite side of elongate slot (306). In some versions, cam surfaces (352a, 352b) of lower detents (346a, 346b) may engage respective upper edges of elongate slot (306) for temporarily pivoting beams (342a, 342b) slightly transversely inwardly during attachment of adjunct (330) to staple cartridge deck (304) to facilitate insertion of latches (340a, 340b) into elongate slot (306), with latches (340a, 340b) subsequently resiliently assuming the latched state to provide a snap-fit between latches (340a, 340b) and undercut surfaces (320).

As shown in FIG. 13B, adjunct (330) may be released from staple cartridge deck (304) by latches (340a, 340b) when latches (340a, 340b) are in the unlatched state. In the illustrated unlatched state, abutment surfaces (350a, 350b) of lower detents (346a, 346b) disengage the respective undercut surfaces (320) of cartridge body (302) to thereby release adjunct (330) from staple cartridge deck (304). Latches (340a, 340b) of the present version are configured to actively release adjunct (330) from staple cartridge deck (304) in response to firing of staple cartridge (300) by converting the upward raising of the transversely-inner staple drivers (309) during firing of staple cartridge (300) into transversely inward pivoting of lower detents (346a, 346b). More particularly, the transversely-inner staple drivers (309) may engage the respective upper detents (348a, 348b) as the transversely-inner staple drivers (309) are cammed upwardly by wedge sled (86) and may urge the respective upper detents (348a, 348b) upwardly to pivot latches (340a, 340b) about hinge (354) such that lower detents (346a, 346b) are each pivoted transversely inwardly for disengaging abutment surfaces (350a, 350b) from the respective undercut surfaces (320).

While latches (340a, 340b) have been described as being incorporated into compressible monolithic adjunct (330), it will be appreciated that latches (340a, 340b) may just as easily be incorporated into a multi-layer adjunct similar to buttress assemblies (110, 112) described above in connection with FIGS. 7-9.

Figure 14A:
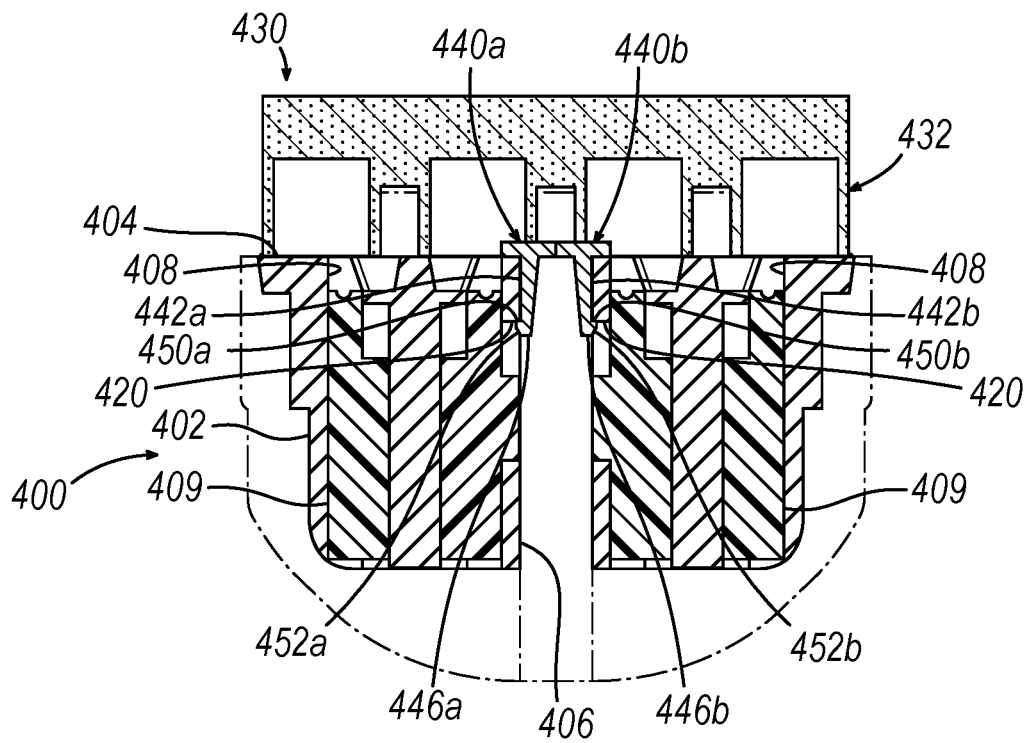
FIG. 14A depicts a cross-sectional end view of another exemplary staple cartridge in combination with another exemplary adjunct, showing deflectable attachment features of the adjunct engaged with undercut features of the staple cartridge for attaching the adjunct to the staple cartridge.
Figure 14B:
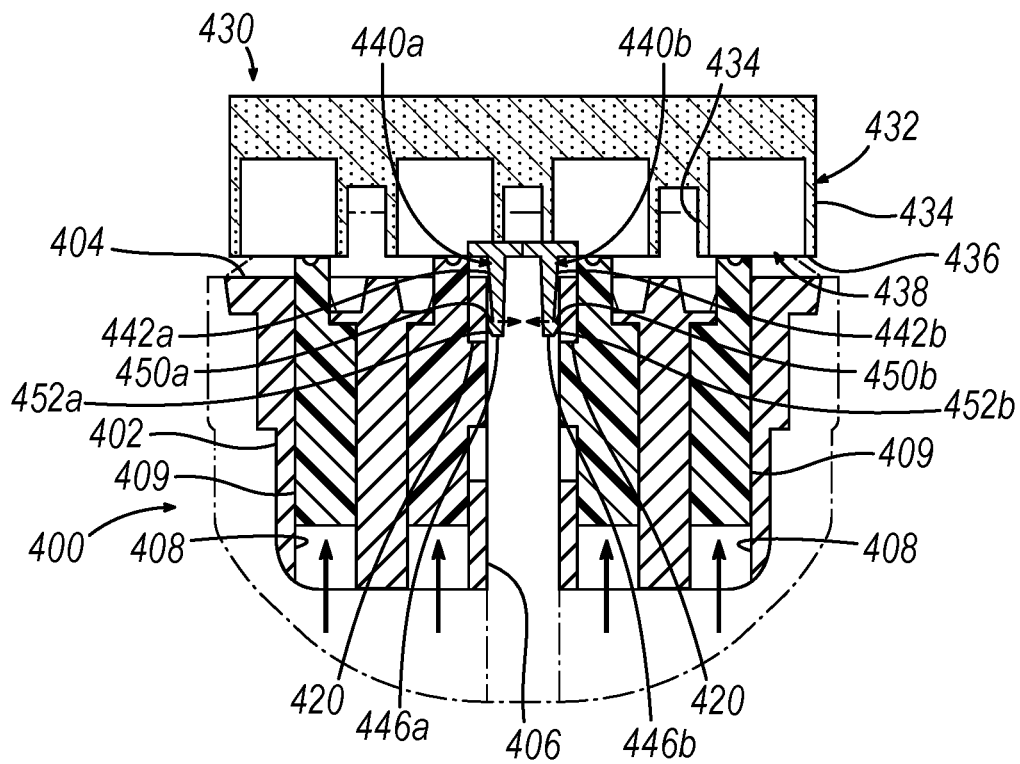
FIG. 14B depicts a cross-sectional end view of the staple cartridge and adjunct of FIG. 14A, showing staple drivers housed within the staple cartridge driven upwardly to disengage the deflectable attachment features from the undercut features for releasing the adjunct from the staple cartridge.

B. Exemplary Adjunct with Deflectable Attachment Features for Engaging Undercut Features of Cartridge Slot FIGS. 14A-14B show another exemplary compressible monolithic adjunct (430) configured for releasable attachment to a staple cartridge (400). Staple cartridge (400) and adjunct (430) are configured for use with end effector (50) and are similar to staple cartridge (200) and adjunct (230) described above except as otherwise described below. In this regard, staple cartridge (400) includes a cartridge body (402) having an upwardly facing deck (404), an elongate slot (406) extending along a central axis of cartridge body (402) and opening upwardly through deck (404), and a plurality of staple openings (408) extending through deck (404) on each side of elongate slot (406). Each staple opening (408) slidably houses an unformed staple (not shown), similar to staple (80), and a respective staple driver (409) configured to drive the staple outwardly toward anvil (56) to be formed. A lower tray (not shown) of staple cartridge (400) retains the staples and staple drivers within cartridge body (402). Cartridge body (402) of the present example further includes a transversely-opposed pair of undercut surfaces (420) each positioned on a respective side of elongate slot (406) and configured to facilitate releasable attachment of an adjunct, such as adjunct (430), to staple cartridge deck (404), as described in greater detail below.

Adjunct (430) has a plurality of three-dimensional, resiliently compressible nodules (432) that are integrally connected with one another in a plurality of linear arrays defining a lattice structure having an elongate rectangular shape in a manner similar to that described above in connection with FIGS. 10-12. Each nodule (432) of the present example has a generally cuboid shape defining four side surfaces (434), a lower surface (436), and an opening (438) in lower surface (436) that extends along a vertical central axis of nodule (432) and defines an open, hollow interior of nodule (432).

In the example shown, adjunct (430) further includes a pair of attachment features in the form of deflectable latches (440a, 440b) coupled to transversely-inner nodules (432) and configured to be at least partially received within elongate slot (406) on opposite sides of elongate slot (406). Each latch (440a, 440b) includes a beam (442a, 442b) extending generally downwardly from an inner sidewall of the respective nodule (432) and a lower detent (446a, 446b) extending generally transversely outwardly from a lower portion of the respective beam (442a, 442b) for selectively engaging a respective undercut surface (420) of cartridge body (402). In the example shown, each lower detent (446a, 446b) includes a generally horizontally-extending abutment surface (450a, 450b) and a cam surface (452a, 452b) tapered transversely inwardly in a generally downward direction from an outer edge of the respective abutment surface (450a, 450b), the purposes of which are described below.

Beams (442a, 442b) of latches (440a, 440b) of the present version are flexibly cantilevered from respective nodules (432) such that latches (440a, 440b) are deflectable relative to each other in the transverse direction between a latched state (FIG. 14A) and an unlatched state (FIG. 14B). In some versions, latches (440a, 440b) may be resiliently biased toward the latched state. In addition, or alternatively, any one or more of nodules (432) and/or latches (440a, 440b) may be integrally formed together as a unitary piece. For example, any one or more of nodules (432) and/or latches (440a, 440b) may be 3D-printed together. In some versions, latches (440a, 440b) may be constructed of a different material than that of nodules (432).

As shown in FIG. 14A, adjunct (430) may be selectively attached to staple cartridge deck (404) via latches (440a, 440b) when latches (440a, 440b) are in the latched state. In the illustrated latched state, abutment surfaces (450a, 450b) of lower detents (446a, 446b) engage respective undercut surfaces (420) of cartridge body (402) to thereby attach adjunct (430) to staple cartridge deck (404), while cam surfaces (452a, 452b) of lower detents (446a, 446b) are each aligned in a vertical direction with at least a portion of a transversely-inner staple driver (409) on a corresponding same side of elongate slot (406). In some versions, cam surfaces (452a, 452b) of lower detents (446a, 446b) may engage respective upper edges of elongate slot (406) for temporarily deflecting beams (442a, 442b) slightly transversely inwardly during attachment of adjunct (430) to staple cartridge deck (404) to facilitate insertion of latches (440a, 440b) into elongate slot (406), with latches (440a, 440b) subsequently resiliently assuming the latched state to provide a snap-fit between latches (440a, 440b) and undercut surfaces (420).

As shown in FIG. 14B, adjunct (430) may be released from staple cartridge deck (404) by latches (440a, 440b) when latches (440a, 440b) are in the unlatched state. In the illustrated unlatched state, abutment surfaces (450a, 450b) of lower detents (446a, 446b) disengage the respective undercut surfaces (420) of cartridge body (402) to thereby release adjunct (430) from staple cartridge deck (404). Latches (440a, 440b) of the present version are configured to actively release adjunct (430) from staple cartridge deck (404) in response to firing of staple cartridge (400) by converting the upward raising of the transversely-inner staple drivers (409) during firing of staple cartridge (400) into transversely inward deflection of lower detents (446a, 446b). More particularly, the transversely-inner staple drivers (409) may engage the respective cam surfaces (452a, 452b) of lower detents (446a, 446b) as the transversely-inner staple drivers (409) are cammed upwardly by wedge sled (86) and may urge the respective lower detents (446a, 446b) transversely inwardly for disengaging abutment surfaces (450a, 450b) from the respective undercut surfaces (420).

While latches (440a, 440b) of the present version are coupled to transversely-inner nodules (432) and are configured for insertion within elongate slot (406) for engaging abutment surfaces (450a, 450b) with undercut surfaces (420) to facilitate attachment of adjunct (430) and for engaging cam surfaces (452a, 452b) with transversely-inner staple drivers (409) to facilitate active release of adjunct (430), it will be appreciated that latches (440a, 440b) may alternatively be coupled to transversely-outer nodules (432). For example, latches (440a, 440b) positioned in this manner may be configured for engaging abutment surfaces (450a, 450b) with undercut surfaces positioned on outer sides of cartridge body (402) to facilitate attachment of adjunct (430) and for engaging cam surfaces (452a, 452b) with transversely-outer staple drivers (409) to facilitate active release of adjunct (430). While latches (440a, 440b) have been described as being incorporated into compressible monolithic adjunct (430), it will be appreciated that latches (440a, 440b) may just as easily be incorporated into a multi-layer adjunct similar to buttress assemblies (110, 112) described above in connection with FIGS. 7-9.

Figure 15:
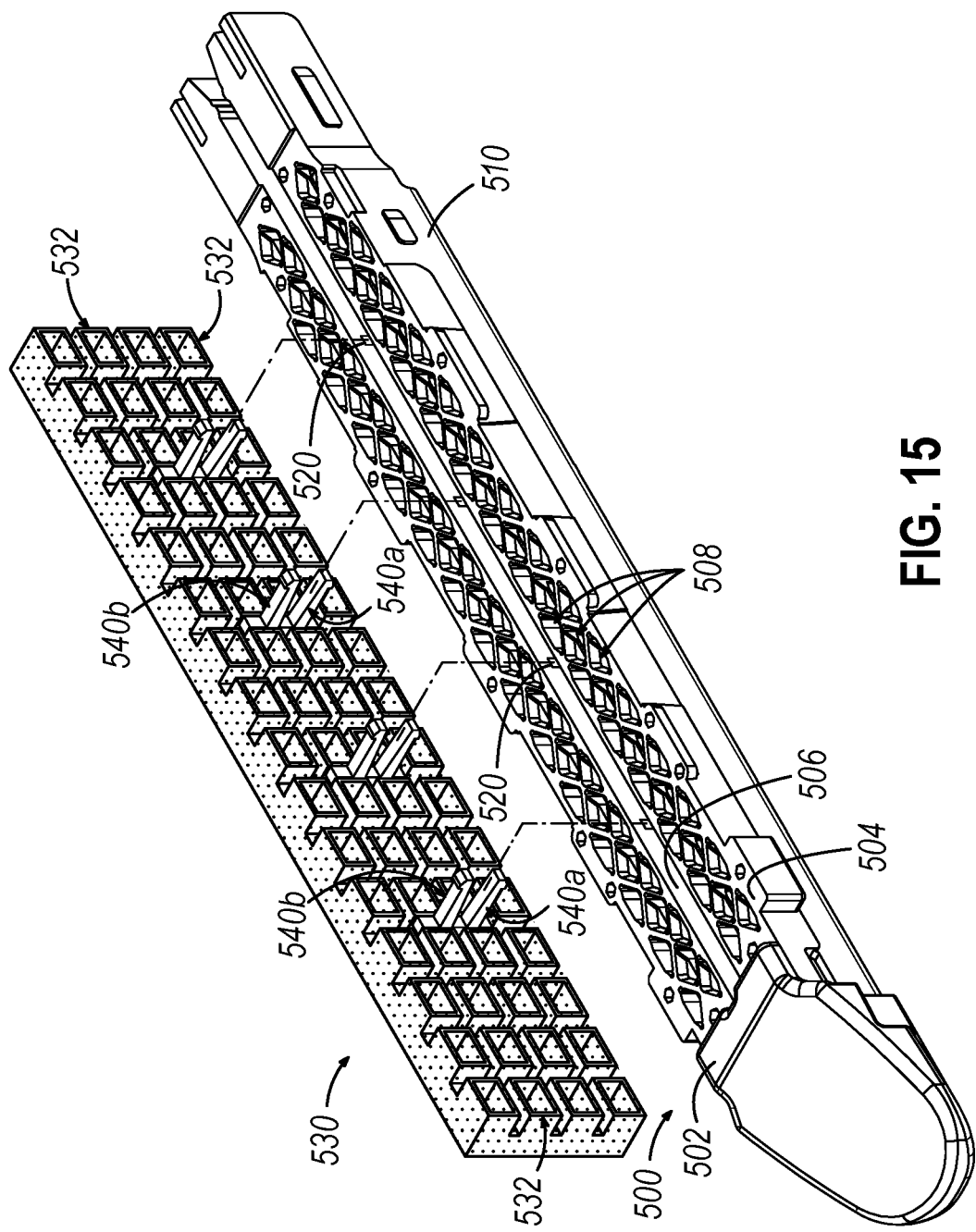
FIG. 15 depicts an exploded perspective view of another exemplary staple cartridge in combination with another exemplary adjunct, showing transversely-offset pairs of deflectable attachment features extending downwardly from respective nodules of the adjunct for selectively engaging undercut features of the staple cartridge.
Figure 16A:
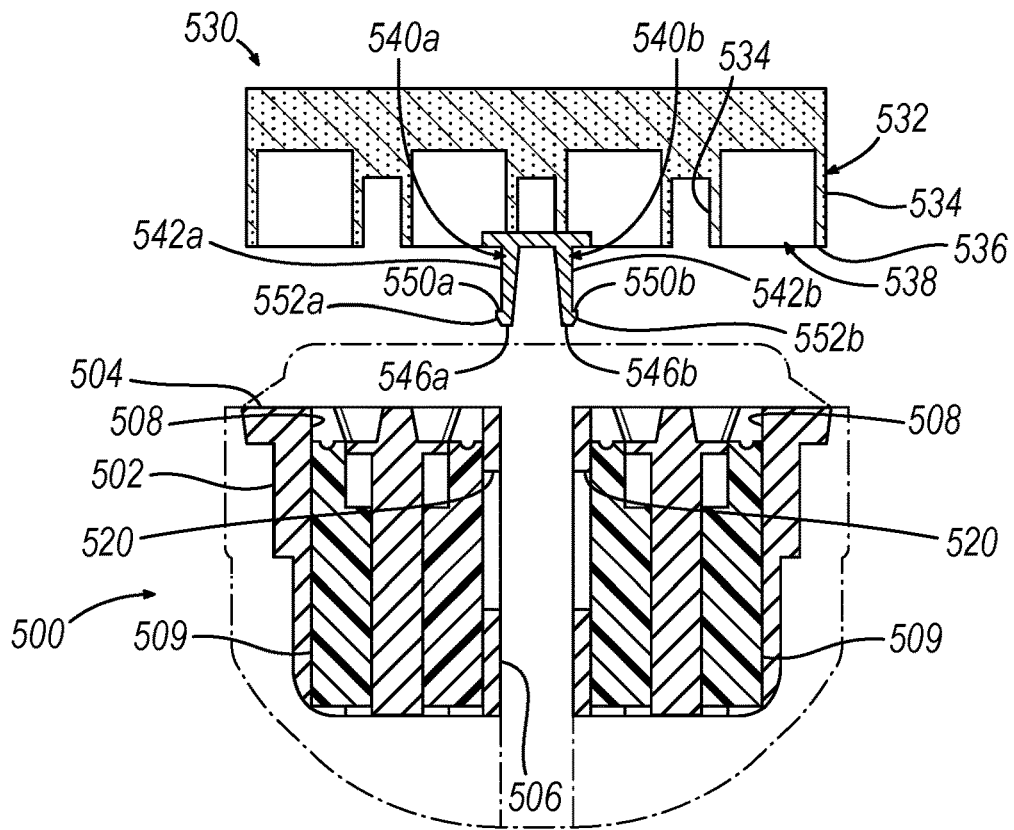
FIG. 16A depicts a cross-sectional end view of the staple cartridge and adjunct of FIG. 15, showing the adjunct positioned above the staple cartridge with cam surfaces of the deflectable attachment features aligned with respective upper edges of an elongate slot of the staple cartridge.
Figure 16B:
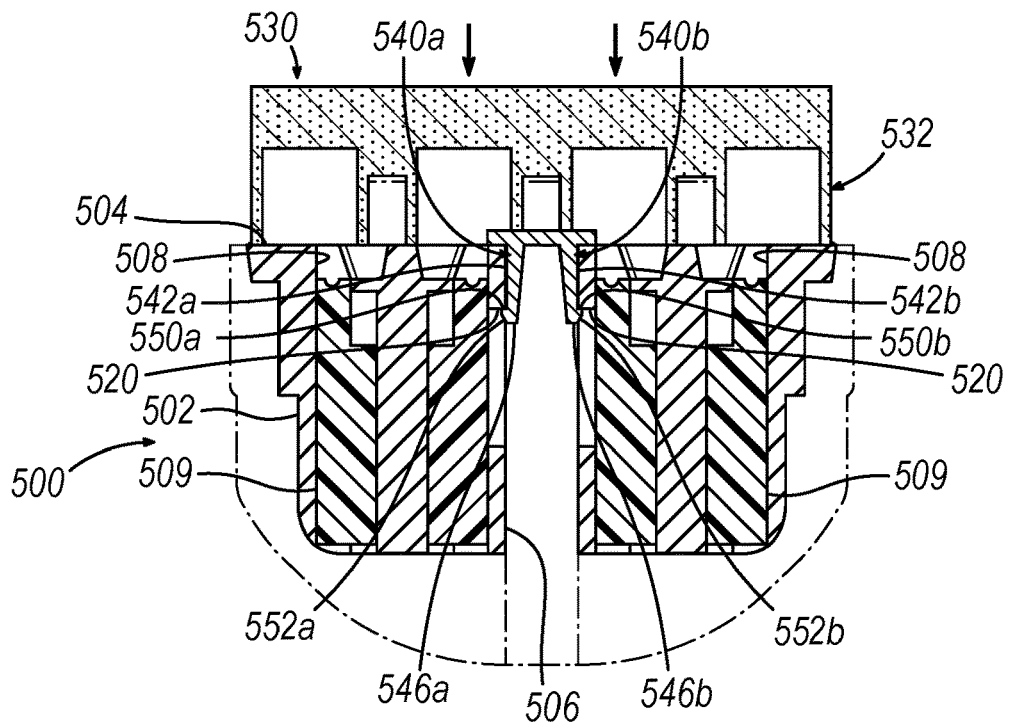
FIG. 16B depicts a cross-sectional end view of the staple cartridge and adjunct of FIG. 15, showing the deflectable attachment features of the adjunct engaged with the undercut features of the staple cartridge for attaching the adjunct to the staple cartridge.

C. Exemplary Adjunct with Offset Pairs of Deflectable Attachment Features for Engaging Undercut Features of Cartridge Slot FIGS. 15-16B show another exemplary compressible monolithic adjunct (530) configured for releasable attachment to a staple cartridge (500). Staple cartridge (500) and adjunct (530) are configured for use with end effector (50) and are similar to staple cartridge (200) and adjunct (230) described above except as otherwise described below. In this regard, staple cartridge (500) includes a cartridge body (502) having an upwardly facing deck (504), an elongate slot (506) extending along a central axis of cartridge body (502) and opening upwardly through deck (504), and a plurality of staple openings (508) extending through deck (504) on each side of elongate slot (506). Each staple opening (508) slidably houses an unformed staple (not shown), similar to staple (80), and a respective staple driver (509) (FIGS. 16A-16B) configured to drive the staple outwardly toward anvil (56) to be formed. A lower tray (510) of staple cartridge (500) retains the staples and staple drivers within cartridge body (502). Cartridge body (502) of the present example further includes a plurality of undercut surfaces (520) each positioned on a respective side of elongate slot (506) and configured to facilitate releasable attachment of an adjunct, such as adjunct (530), to staple cartridge deck (504), as described in greater detail below.

Adjunct (530) has a plurality of three-dimensional, resiliently compressible nodules (532) that are integrally connected with one another in a plurality of linear arrays defining a lattice structure having an elongate rectangular shape in a manner similar to that described above in connection with FIGS. 10-12. Each nodule (532) of the present example has a generally cuboid shape defining four side surfaces (534), a lower surface (536), and an opening (538) in lower surface (536) that extends along a vertical central axis of nodule (532) and defines an open, hollow interior of nodule (532).

In the example shown, adjunct (530) further includes plurality of attachment features in the form of transversely-offset pairs of deflectable latches (540a, 540b) coupled to transversely-inner nodules (532) and configured to be at least partially received within elongate slot (506) on opposite sides of elongate slot (506). More particularly, latches (540a, 540b) of each pair are offset from each other in the longitudinal direction. While four offset pairs of latches (540a, 540b) are shown, it will be appreciated that any suitable number of offset pairs of latches (540a, 540b) may be used. Each latch (540a, 540b) includes a beam (542a, 542b) extending generally downwardly from adjunct (530) at a location between an adjacent pair of nodules (532), and a lower detent (546a, 546b) extending generally transversely outwardly from a lower portion of the respective beam (542a, 542b) for selectively engaging a respective undercut surface (520) of cartridge body (502). In the example shown, each lower detent (546a, 546b) includes a generally horizontally-extending abutment surface (550a, 550b) and a cam surface (552a, 552b) tapered transversely inwardly in a generally downward direction from an outer edge of the respective abutment surface (550a, 550b), the purposes of which are described below.

Beams (542a, 542b) of latches (540a, 540b) of the present version are flexibly cantilevered from respective nodules (532) such that latches (540a, 540b) are deflectable relative to each other in the transverse direction between the illustrated latched state and an unlatched state (not shown). In some versions, latches (540a, 540b) may be resiliently biased toward the latched state. In addition, or alternatively, any one or more of nodules (532) and/or latches (540a, 540b) may be integrally formed together as a unitary piece. For example, any one or more of nodules (532) and/or latches (540a, 540b) may be 3D-printed together. In some versions, latches (540a, 540b) may be constructed of a different material than that of nodules (532).

As shown in FIG. 16A, adjunct (530) may be initially positioned over staple cartridge deck (504) with cam surfaces (552a, 552b) of lower detents (546a, 546b) aligned in a vertical direction with upper edges of elongate slot (506), such that cam surfaces (552a, 552b) may engage respective upper edges of elongate slot (506) for temporarily deflecting beams (542a, 542b) slightly transversely inwardly during attachment of adjunct (530) to staple cartridge deck (504) to facilitate insertion of latches (540a, 540b) into elongate slot (506), with latches (540a, 540b) subsequently resiliently assuming the latched state to provide a snap-fit between latches (540a, 540b) and undercut surfaces (520). Due to the offset of latches (540a, 540b) from each other in the longitudinal direction, each latch (540a, 540b) may be deflected transversely inwardly across a centerline of adjunct (530) without colliding with each other during such attachment of adjunct (530) to staple cartridge deck (504).

As shown in FIG. 16B, adjunct (530) may be selectively attached to staple cartridge deck (504) via latches (540a, 540b) when latches (540a, 540b) are in the latched state. In the illustrated latched state, abutment surfaces (550a, 550b) of lower detents (546a, 546b) engage respective undercut surfaces (520) of cartridge body (502) to thereby attach adjunct (530) to staple cartridge deck (504). It will be appreciated that adjunct (530) may be released from staple cartridge deck (504) by latches (540a, 540b) when latches (540a, 540b) are in the unlatched state, which may be similar to that shown in FIG. 14B. For example, in the unlatched state, abutment surfaces (550a, 550b) of lower detents (546a, 546b) may disengage the respective undercut surfaces (520) of cartridge body (502) to thereby release adjunct (530) from staple cartridge deck (504). In some versions, latches (540a, 540b) may be configured to actively release adjunct (530) from staple cartridge deck (504) in response to firing of staple cartridge (500), such as by converting the upward raising of the transversely-inner staple drivers (509) during firing of staple cartridge (500) into transversely inward deflection of lower detents (546a, 546b) in a manner similar to that described above in connection with FIGS. 14A-14B.

While latches (540a, 540b) have been described as being incorporated into compressible monolithic adjunct (530), it will be appreciated that latches (540a, 540b) may just as easily be incorporated into a multi-layer adjunct similar to buttress assemblies (110, 112) described above in connection with FIGS. 7-9.

Figure 17A:
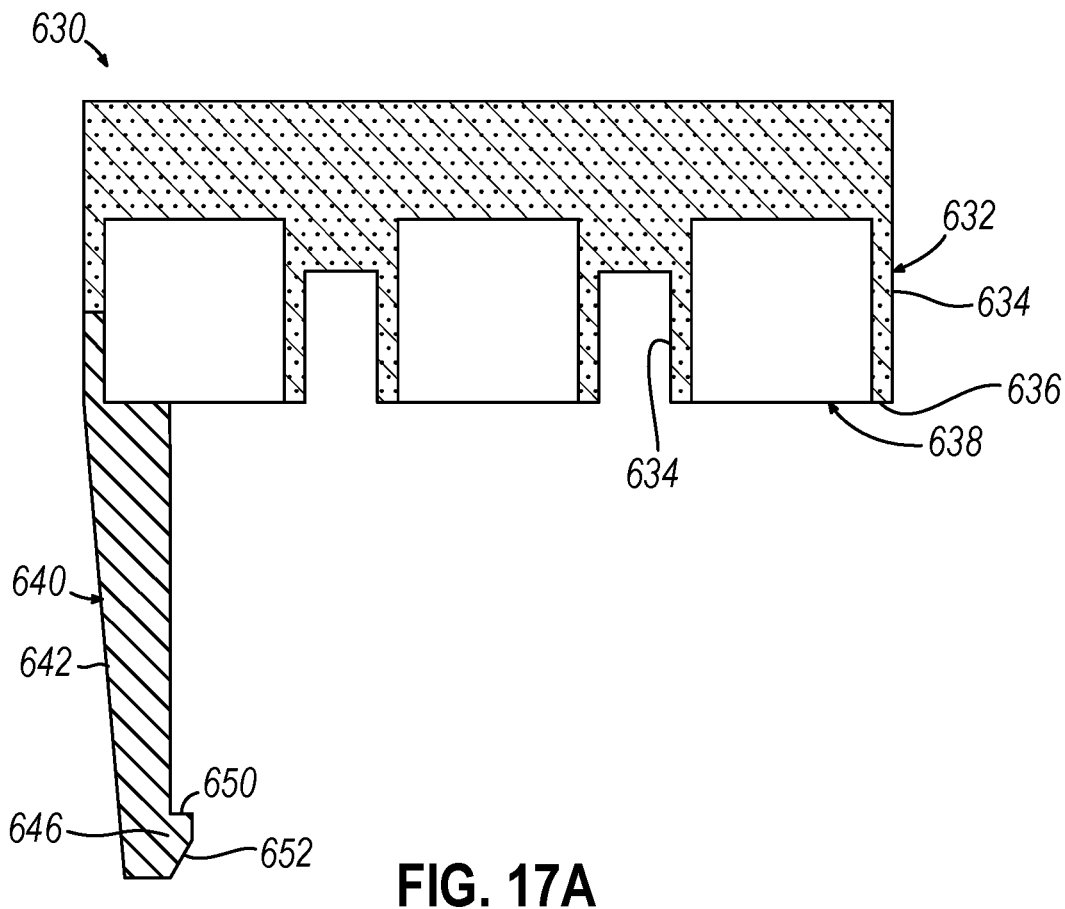
FIG. 17A depicts a cross-sectional end view of another exemplary adjunct, showing a deflectable attachment feature extending generally vertically such that the deflectable attachment feature is generally orthogonal relative to a lattice structure of the adjunct.
Figure 17B:
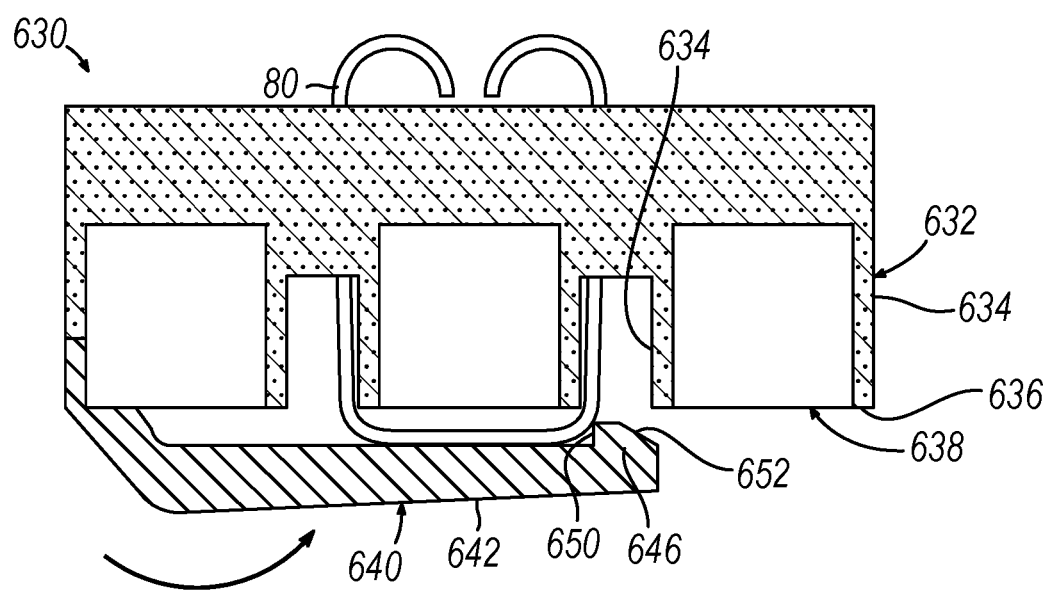
FIG. 17B depicts a cross-sectional end view of the adjunct of FIG. 17A, showing the deflectable attachment feature extending generally horizontally such that the deflectable attachment feature is generally flush with the lattice structure of the adjunct.

D. Exemplary Adjunct with Deflectable Attachment Feature Resiliently Biased Toward Flush State FIGS. 17A-17B show another exemplary compressible monolithic adjunct (630) configured for releasable attachment to a staple cartridge (not shown) similar to staple cartridge (200). Adjunct (630) is configured for use with end effector (50) and is similar adjunct (230) described above except as otherwise described below. In this regard, adjunct (630) has a plurality of three-dimensional, resiliently compressible nodules (632) that are integrally connected with one another in a plurality of linear arrays defining a lattice structure having an elongate rectangular shape in a manner similar to that described above in connection with FIGS. 10-12. Each nodule (632) of the present example has a generally cuboid shape defining four side surfaces (634), a lower surface (636), and an opening (638) in lower surface (636) that extends along a vertical central axis of nodule (632) and defines an open, hollow interior of nodule (632).

In the example shown, adjunct (630) further includes at least one attachment feature in the form of a deflectable latch (640) coupled to a sidewall of a transversely-inner nodule (632) configured to be at least partially received within an elongate slot of the staple cartridge. Latch (640) includes a beam (642) configured to extend generally downwardly from a sidewall of the respective nodule (632) and a lower detent (646) extending generally transversely outwardly from a lower portion of beam (642) for selectively engaging a respective undercut surface (not shown) of the cartridge body. In the example shown, lower detent (646) includes a generally horizontally-extending abutment surface (650) and a cam surface (652) tapered transversely inwardly in a generally downward direction from a point at or near an outer edge of abutment surface (650), the purposes of which are described below.

Beam (642) of latch (640) of the present version is flexibly cantilevered from a respective nodule (632) such that latch (640) is deflectable in the transverse direction between a latched state (FIG. 17A) and an unlatched state (not shown), and is further movable to a flush state (FIG. 17B). In some versions, latch (640) may be resiliently biased toward the flush state. In addition, or alternatively, nodules (632) and latch (640) may be integrally formed together as a unitary piece. For example, nodules (632) and latch (640) may be 3D-printed together. In some versions, latch (640) may be constructed of a different material than that of nodules (632).

It will be appreciated that adjunct (630) may be selectively attached to staple cartridge deck (604) via latch (640) when latch (640) is in the latched state, and may be selectively released from staple cartridge deck (604) by latch (640) when latch (640) is in the unlatch state, in a manner similar to that described above in connection with FIGS. 14A-14B, for example. In some versions, latch (640) may resiliently assume the flush state after adjunct (630) is released from staple cartridge deck (604) with staple (80) pierced therethrough, as shown in FIG. 17B. In the illustrated flush state, beam (642) extends generally transversely and is thus substantially parallel to the lattice structure defined by nodules (632) to thereby contact and apply additional compressive force to a crown of staple (80).

While latch (640) has been described as being incorporated into compressible monolithic adjunct (630), it will be appreciated that latch (640) may just as easily be incorporated into a multi-layer adjunct similar to buttress assemblies (110, 112) described above in connection with FIGS. 7-9.

Figure 18:
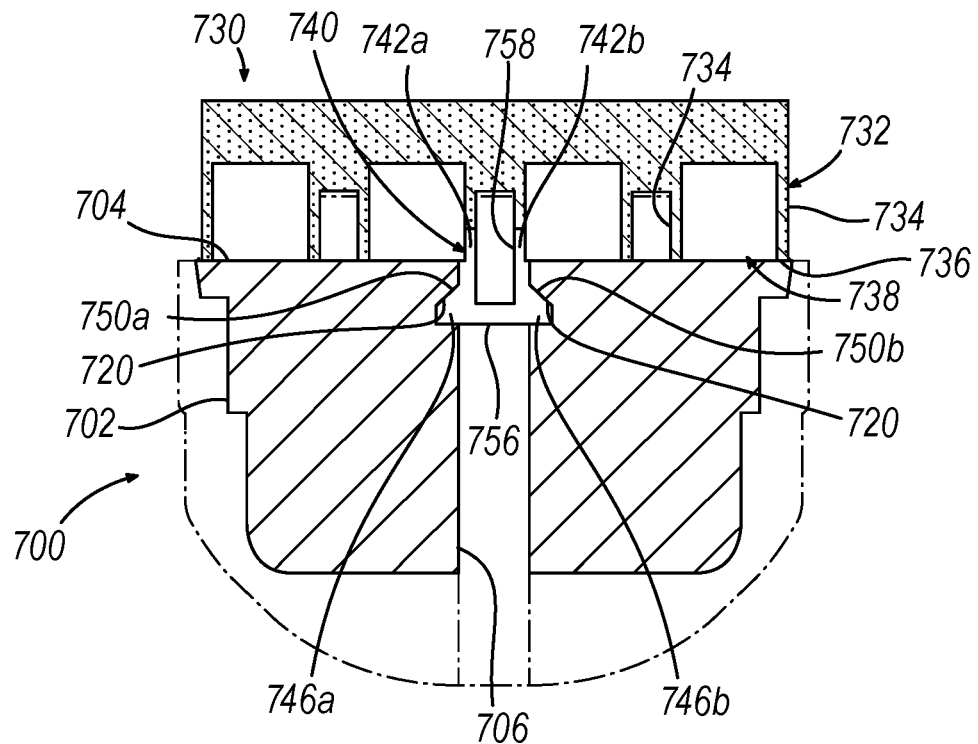
FIG. 18 depicts a cross-sectional end view of another exemplary staple cartridge in combination with another exemplary adjunct, showing a dovetail-shaped attachment feature of the adjunct engaged with undercut features of the staple cartridge for attaching the adjunct to the staple cartridge.

E. Exemplary Adjunct with Dovetail-Shaped Attachment Feature for Engaging Undercut Features of Cartridge Slot FIG. 18 shows another exemplary compressible monolithic adjunct (730) configured for releasable attachment to a staple cartridge (700). Staple cartridge (700) and adjunct (730) are configured for use with end effector (50) and are similar to staple cartridge (200) and adjunct (230) described above except as otherwise described below. In this regard, staple cartridge (700) includes a cartridge body (702) having an upwardly facing deck (704), an elongate slot (706) extending along a central axis of cartridge body (702) and opening upwardly through deck (704), and a plurality of staple openings (not shown) extending through deck (704) on each side of elongate slot (706). Each staple opening slidably houses an unformed staple (not shown), similar to staple (80), and a respective staple driver (not shown) configured to drive the staple outwardly toward anvil (56) to be formed. A lower tray (not shown) of staple cartridge (700) retains the staples and staple drivers within cartridge body (702). Cartridge body (702) of the present example further includes a transversely-opposed pair of undercut surfaces (720) each positioned on a respective side of elongate slot (706) and configured to facilitate releasable attachment of an adjunct, such as adjunct (730), to staple cartridge deck (704), as described in greater detail below.

Adjunct (730) has a plurality of three-dimensional, resiliently compressible nodules (732) that are integrally connected with one another in a plurality of linear arrays defining a lattice structure having an elongate rectangular shape in a manner similar to that described above in connection with FIGS. 10-12. Each nodule (732) of the present example has a generally cuboid shape defining four side surfaces (734), a lower surface (736), and an opening (738) in lower surface (736) that extends along a vertical central axis of nodule (732) and defines an open, hollow interior of nodule (732).

In the example shown, adjunct (730) further includes at least one attachment feature in the form of at least one transversely centered dovetail-shaped rail (740) coupled to transversely-inner nodules (732) and configured to be at least partially received within elongate slot (706). Rail (740) includes a pair of beams (742a, 742b) each extending generally downwardly from an inner sidewall of a respective nodule (732) and a lower detent (746a, 746b) extending generally transversely outwardly from a lower portion of the respective beam (742a, 742b) for selectively engaging a respective undercut surface (720) of cartridge body (702). In the example shown, each lower detent (746a, 746b) includes an angled abutment surface (750a, 750b) tapered transversely outwardly in a generally downward direction, the purposes of which are described below. In any event, rail (740) also includes a lower bridge (756) extending transversely between the lower portions of beams (742a, 742b) for maintaining lower detents (746a, 746b) at a fixed distance from each other. Lower bridge (756) is configured to be severed during firing of staple cartridge (700), such as by cutting edge (62) of firing member (60), to enable relative movement between lower detents (746a, 746b) in the transverse direction. In this regard, lower bridge (756), beams (742a, 742b) and the transversely-inner nodules (732) collectively define a hollow interior (758) for promoting severing of bridge (756) by cutting edge (62). In some versions, rail (740) may extend along substantially an entire length of the lattice structure defined by nodules (732). In other versions, a plurality of rails (740) may extend along respective portions of the length of the lattice structure defined by nodules (732).

Beams (742a, 742b) of rail (740) of the present version are flexibly cantilevered from respective nodules (732) when lower bridge (756) is severed such that the separated, transversely-opposed segments of rail (740) are deflectable relative to each other in the transverse direction. In some versions, any one or more of nodules (732) and/or rail (740) may be integrally formed together as a unitary piece. For example, any one or more of nodules (732) and/or rail (740) may be 3D-printed together. In some versions, rail (740) may be constructed of a different material than that of nodules (732).

As shown in FIG. 18, adjunct (730) may be selectively attached to staple cartridge deck (704) via rail (740) when rail (740) is in an unsevered state. In the illustrated unsevered state, abutment surfaces (750a, 750b) of lower detents (746a, 746b) engage respective undercut surfaces (720) of cartridge body (702) to thereby attach adjunct (730) to staple cartridge deck (704). In some versions, adjunct (730) may be translated longitudinally along the length of staple cartridge (700), such as from a proximal end thereof, with abutment surfaces (750a, 750b) sliding along the respective undercut surfaces (720) to facilitate insertion of rail (740) into elongate slot (706). To that end, staples (80) may be flush with or recessed below staple cartridge deck (704) during such longitudinal translation of adjunct (730) to inhibit snagging of staples (80) by nodules (732).

It will be appreciated that adjunct (730) may be released from staple cartridge deck (704) by separated, transversely-opposed segments of rail (740) when rail (740) is in the severed state. In the severed state (not shown), abutment surfaces (750a, 750b) of lower detents (746a, 746b) may disengage the respective undercut surfaces (720) of cartridge body (702) to thereby release adjunct (730) from staple cartridge deck (704). Rail (740) of the present version is configured to passively release adjunct (730) from staple cartridge deck (704) after firing of staple cartridge (700) and the resulting severing of lower bridge (756) in response to separation of end effector (50) from the stapled tissue. More particularly, staple cartridge deck (704) may be lowered downwardly relative to adjunct (730) during such separation of end effector (50) from the stapled tissue and may urge the respective lower detents (746a, 746b) transversely inwardly for disengaging abutment surfaces (750a, 750b) from the respective undercut surfaces (720). In some versions, lower detents (746a, 746b) may be resiliently biased transversely inwardly when lower bridge (756) is severed, such that rail (740) may be configured to actively release adjunct (730) from staple cartridge deck (704) in response to firing of staple cartridge (700).

While rail (740) has been described as being incorporated into compressible monolithic adjunct (730), it will be appreciated that rail (740) may just as easily be incorporated into a multi-layer adjunct similar to buttress assemblies (110, 112) described above in connection with FIGS. 7-9.

Figure 19:
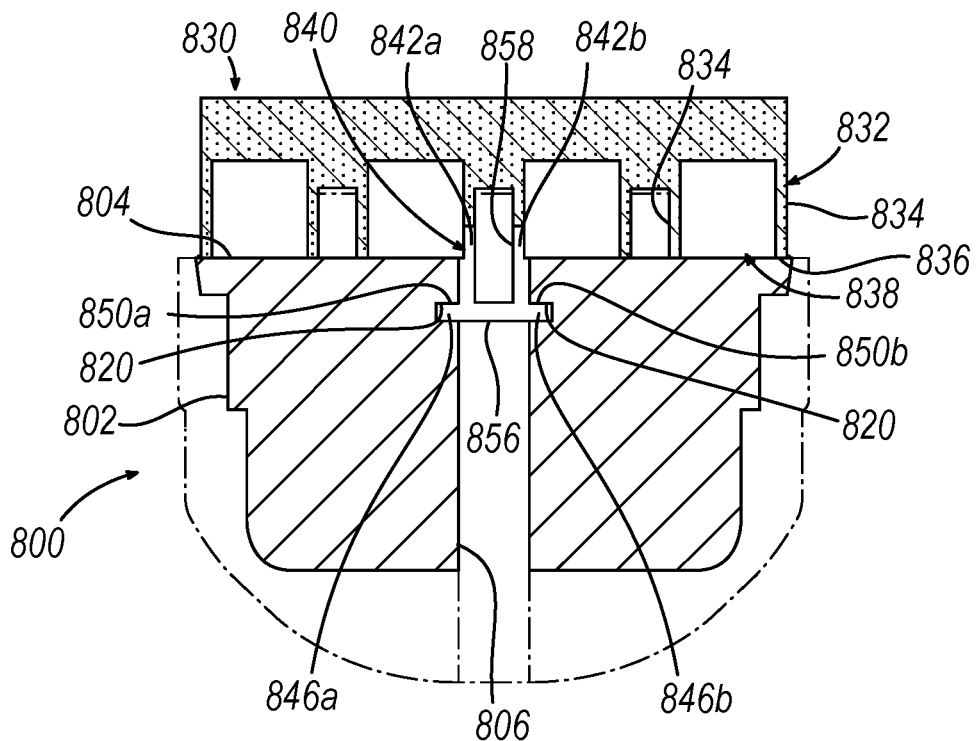
FIG. 19 depicts a cross-sectional end view of another exemplary staple cartridge in combination with another exemplary adjunct, showing a T-shaped attachment feature of the adjunct engaged with undercut features of the staple cartridge for attaching the adjunct to the staple cartridge.

F. Exemplary Adjunct with Short T-Shaped Attachment Feature for Engaging Undercut Features of Cartridge Slot FIG. 19 shows another exemplary compressible monolithic adjunct (830) configured for releasable attachment to a staple cartridge (800). Staple cartridge (800) and adjunct (830) are configured for use with end effector (50) and are similar to staple cartridge (200) and adjunct (230) described above except as otherwise described below. In this regard, staple cartridge (800) includes a cartridge body (802) having an upwardly facing deck (804), an elongate slot (806) extending along a central axis of cartridge body (802) and opening upwardly through deck (804), and a plurality of staple openings (not shown) extending through deck (804) on each side of elongate slot (806). Each staple opening slidably houses an unformed staple (not shown), similar to staple (80), and a respective staple driver (not shown) configured to drive the staple outwardly toward anvil (56) to be formed. A lower tray (not shown) of staple cartridge (800) retains the staples and staple drivers within cartridge body (802). Cartridge body (802) of the present example further includes a transversely-opposed pair of undercut surfaces (820) each positioned on a respective side of elongate slot (806) and configured to facilitate releasable attachment of an adjunct, such as adjunct (830), to staple cartridge deck (804), as described in greater detail below.

Adjunct (830) has a plurality of three-dimensional, resiliently compressible nodules (832) that are integrally connected with one another in a plurality of linear arrays defining a lattice structure having an elongate rectangular shape in a manner similar to that described above in connection with FIGS. 10-12. Each nodule (832) of the present example has a generally cuboid shape defining four side surfaces (834), a lower surface (836), and an opening (838) in lower surface (836) that extends along a vertical central axis of nodule (832) and defines an open, hollow interior of nodule (832).

In the example shown, adjunct (830) further includes at least one attachment feature in the form of at least one transversely centered T-shaped rail (840) coupled to transversely-inner nodules (832) and configured to be at least partially received within elongate slot (806). Rail (840) includes a pair of beams (842a, 842b) each extending generally downwardly from an inner sidewall of a respective nodule (832) and a lower detent (846a, 846b) extending generally transversely outwardly from a lower portion of the respective beam (842a, 842b) for selectively engaging a respective undercut surface (820) of cartridge body (802). In the example shown, each lower detent (846a, 846b) includes a generally horizontally-extending abutment surface (850a, 850b), the purposes of which are described below. In any event, rail (840) also includes a lower bridge (856) extending transversely between the lower portions of beams (842a, 842b) for maintaining lower detents (846a, 846b) at a fixed distance from each other. Lower bridge (856) is configured to be severed during firing of staple cartridge (800), such as by cutting edge (62) of firing member (60), to enable relative movement between lower detents (846a, 846b) in the transverse direction. In this regard, lower bridge (856), beams (842a, 842b) and the transversely-inner nodules (832) collectively define a hollow interior (858) for promoting severing of bridge (856) by cutting edge (62). In some versions, rail (840) may extend along substantially an entire length of the lattice structure defined by nodules (832). In other versions, a plurality of rails (840) may extend along respective portions of the length of the lattice structure defined by nodules (832).

Beams (842a, 842b) of rail (840) of the present version are flexibly cantilevered from respective nodules (832) when lower bridge (856) is severed such that the separated, transversely-opposed segments of rail (840) are deflectable relative to each other in the transverse direction. In some versions, any one or more of nodules (832) and/or rail (840) may be integrally formed together as a unitary piece. For example, any one or more of nodules (832) and/or rail (840) may be 3D-printed together. In some versions, rail (840) may be constructed of a different material than that of nodules (832).

As shown in FIG. 19, adjunct (830) may be selectively attached to staple cartridge deck (804) via rail (840) when rail (840) is in an unsevered state. In the illustrated unsevered state, abutment surfaces (850a, 850b) of lower detents (846a, 846b) engage respective undercut surfaces (820) of cartridge body (802) to thereby attach adjunct (830) to staple cartridge deck (804). In some versions, adjunct (830) may be translated longitudinally along the length of staple cartridge (800), such as from a proximal end thereof, with abutment surfaces (850a, 850b) sliding along the respective undercut surfaces (820) to facilitate insertion of rail (840) into elongate slot (806). To that end, staples (80) may be flush with or recessed below staple cartridge deck (804) during such longitudinal translation of adjunct (830) to inhibit snagging of staples (80) by nodules (832).

It will be appreciated that adjunct (830) may be released from staple cartridge deck (804) by separated, transversely-opposed segments of rail (840) when rail (840) is in the severed state. In the severed state (not shown), abutment surfaces (850a, 850b) of lower detents (846a, 846b) may disengage the respective undercut surfaces (820) of cartridge body (802) to thereby release adjunct (830) from staple cartridge deck (804). Rail (840) of the present version is configured to passively release adjunct (830) from staple cartridge deck (804) after firing of staple cartridge (800) and the resulting severing of lower bridge (856) in response to separation of end effector (50) from the stapled tissue. More particularly, staple cartridge deck (804) may be lowered downwardly relative to adjunct (830) during such separation of end effector (50) from the stapled tissue and may urge the respective lower detents (846a, 846b) transversely inwardly for disengaging abutment surfaces (850a, 850b) from the respective undercut surfaces (820). In some versions, lower detents (846a, 846b) may be resiliently biased transversely inwardly when lower bridge (856) is severed, such that rail (840) may be configured to actively release adjunct (830) from staple cartridge deck (804) in response to firing of staple cartridge (800).

While rail (840) has been described as being incorporated into compressible monolithic adjunct (830), it will be appreciated that rail (840) may just as easily be incorporated into a multi-layer adjunct similar to buttress assemblies (110, 112) described above in connection with FIGS. 7-9.

Figure 20:
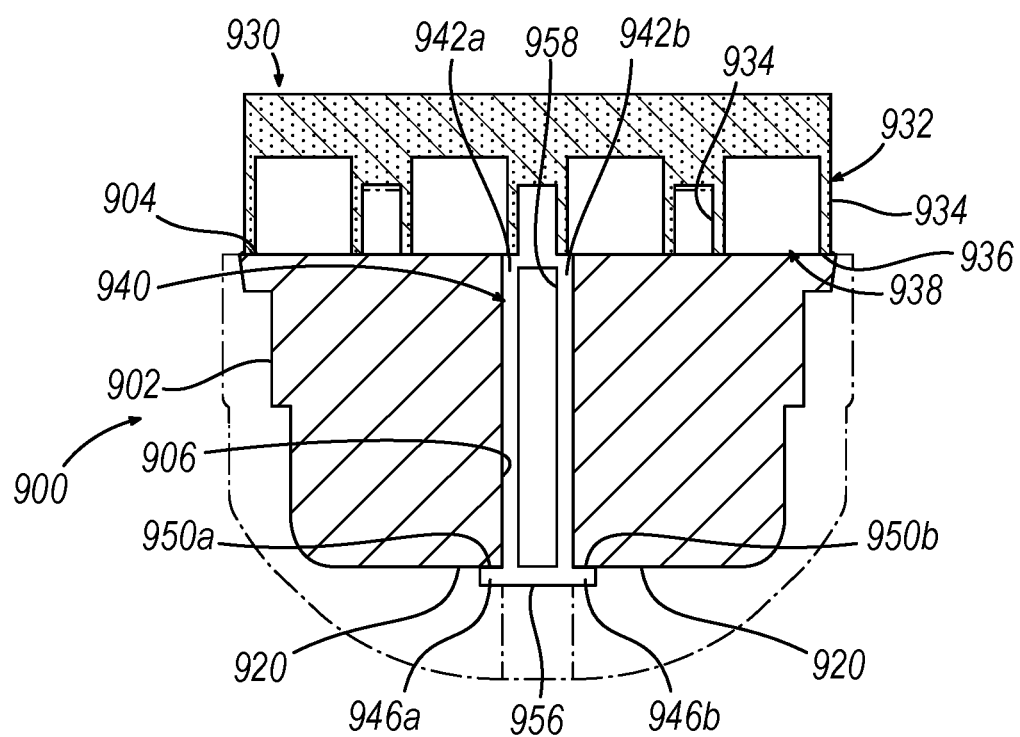
FIG. 20 depicts a cross-sectional end view of another exemplary staple cartridge in combination with another exemplary adjunct, showing a T-shaped attachment feature of the adjunct engaged with bottom surfaces of the staple cartridge for attaching the adjunct to the staple cartridge.
Figure 21A:
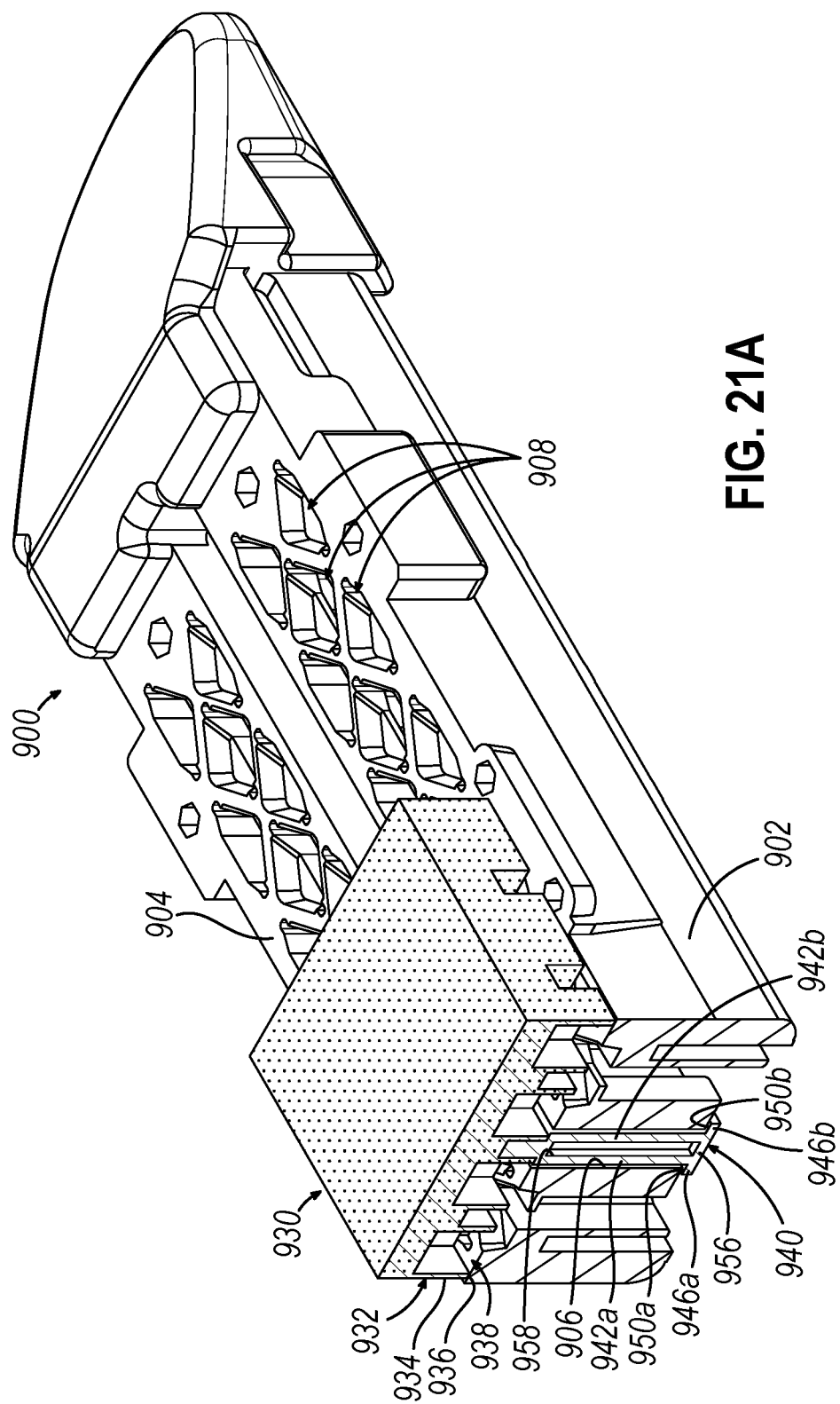
FIG. 21A depicts a perspective view of the staple cartridge and adjunct of FIG. 20, showing the adjunct at a first longitudinal position relative to the staple cartridge.
Figure 21B:
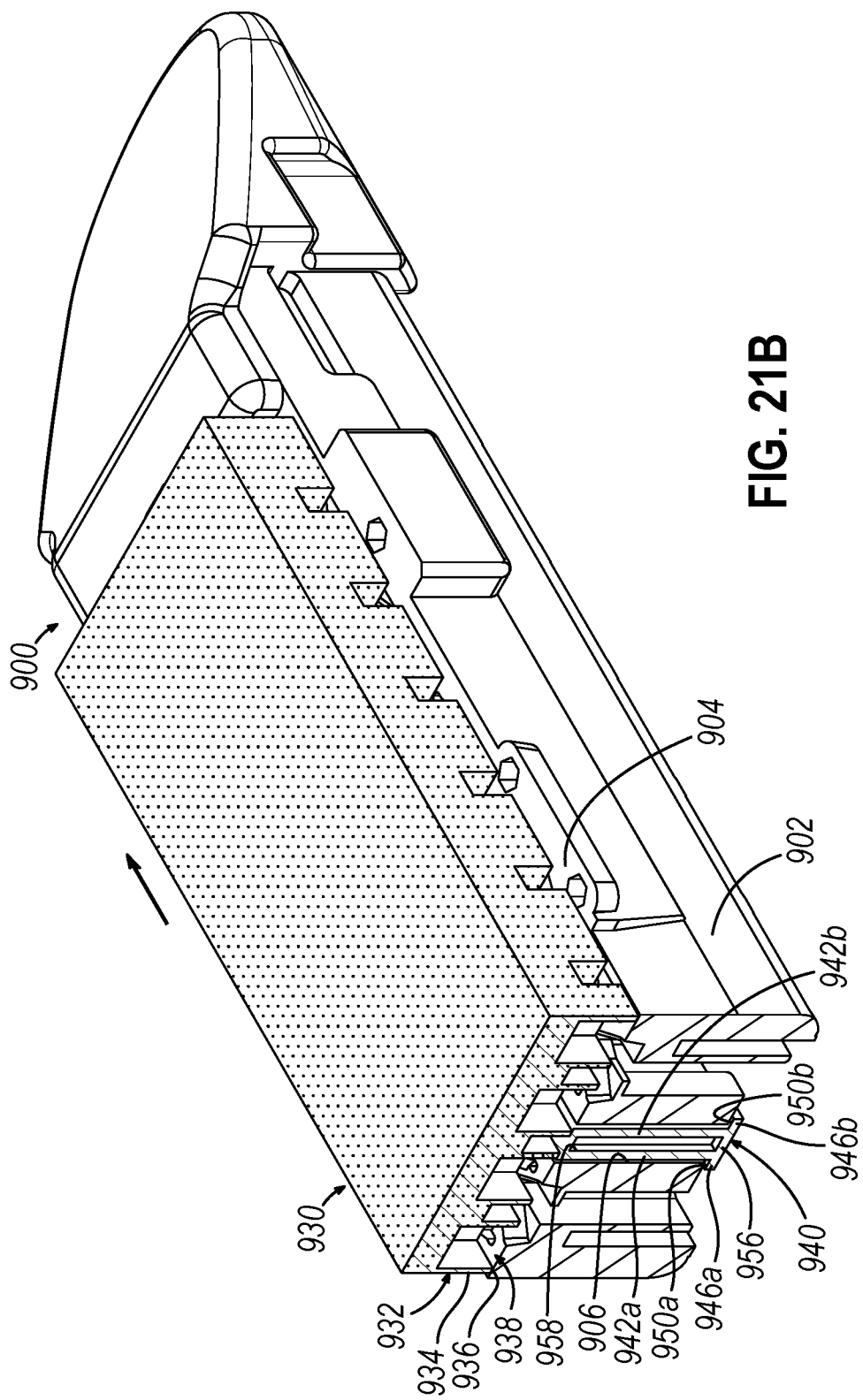
FIG. 21B depicts a perspective view of the staple cartridge and adjunct of FIG. 20, showing the adjunct translated longitudinally to a second longitudinal position relative to the staple cartridge.

G. Exemplary Adjunct with Tall T-Shaped Attachment Feature for Engaging Bottom Surface of Cartridge FIGS. 20-21B show another exemplary compressible monolithic adjunct (930) configured for releasable attachment to a staple cartridge (900). Staple cartridge (900) and adjunct (930) are configured for use with end effector (50) and are similar to staple cartridge (200) and adjunct (230) described above except as otherwise described below. In this regard, staple cartridge (900) includes a cartridge body (902) having an upwardly facing deck (904), an elongate slot (906) extending along a central axis of cartridge body (902) and opening upwardly through deck (904), and a plurality of staple openings (908) (FIG. 21A) extending through deck (904) on each side of elongate slot (906). Each staple opening (908) slidably houses an unformed staple (not shown), similar to staple (80), and a respective staple driver (not shown) configured to drive the staple outwardly toward anvil (56) to be formed. A lower tray (not shown) of staple cartridge (900) retains the staples and staple drivers within cartridge body (902). Cartridge body (902) of the present example further includes a transversely-opposed pair of bottom surfaces (920) each positioned on a respective side of elongate slot (906) and configured to facilitate releasable attachment of an adjunct, such as adjunct (930), to staple cartridge deck (904), as described in greater detail below.

Adjunct (930) has a plurality of three-dimensional, resiliently compressible nodules (932) that are integrally connected with one another in a plurality of linear arrays defining a lattice structure having an elongate rectangular shape in a manner similar to that described above in connection with FIGS. 10-12. Each nodule (932) of the present example has a generally cuboid shape defining four side surfaces (934), a lower surface (936), and an opening (938) in lower surface (936) that extends along a vertical central axis of nodule (932) and defines an open, hollow interior of nodule (932).

In the example shown, adjunct (930) further includes at least one attachment feature in the form of at least one transversely centered T-shaped rail (940) coupled to transversely-inner nodules (932) and configured to be at least partially received within elongate slot (906). Rail (940) includes a pair of beams (942a, 942b) each extending generally downwardly from an inner sidewall of a respective nodule (932) and a lower detent (946a, 946b) extending generally transversely outwardly from a lower portion of the respective beam (942a, 942b) for selectively engaging a respective bottom surface (920) of cartridge body (902). In this regard, beams (942a, 942b) of rail (940) of the present version each have a height substantially equal to or slightly greater than that of elongate slot (906). In the example shown, each lower detent (946a, 946b) includes a generally horizontally-extending abutment surface (950a, 950b), the purposes of which are described below. In any event, rail (940) also includes a lower bridge (956) extending transversely between the lower portions of beams (942a, 942b) for maintaining lower detents (946a, 946b) at a fixed distance from each other. Lower bridge (956) is configured to be severed during firing of staple cartridge (900), such as by cutting edge (62) of firing member (60), to enable relative movement between lower detents (946a, 946b) in the transverse direction. In this regard, lower bridge (956), beams (942a, 942b) and the transversely-inner nodules (932) collectively define a hollow interior (958) for promoting severing of bridge (956) by cutting edge (62). In some versions, rail (940) may extend along substantially an entire length of the lattice structure defined by nodules (932). In other versions, a plurality of rails (940) may extend along respective portions of the length of the lattice structure defined by nodules (932).

Beams (942a, 942b) of rail (940) of the present version are flexibly cantilevered from respective nodules (932) when lower bridge (956) is severed such that the separated, transversely-opposed segments of rail (940) are deflectable relative to each other in the transverse direction. In some versions, any one or more of nodules (932) and/or rail (940) may be integrally formed together as a unitary piece. For example, any one or more of nodules (932) and/or rail (940) may be 3D-printed together. In some versions, rail (940) may be constructed of a different material than that of nodules (932).

As shown in FIG. 20, adjunct (930) may be selectively attached to staple cartridge deck (904) via rail (940) when rail (940) is in an unsevered state. In the illustrated unsevered state, abutment surfaces (950a, 950b) of lower detents (946a, 946b) engage respective bottom surfaces (920) of cartridge body (902) to thereby attach adjunct (930) to staple cartridge deck (904). In some versions, adjunct (930) may be translated longitudinally along the length of staple cartridge (900), such as from a proximal end thereof, with abutment surfaces (950a, 950b) sliding along the respective bottom surfaces (920) to facilitate insertion of rail (940) into elongate slot (906), as shown in FIGS. 21A-21B. To that end, staples (80) may be flush with or recessed below staple cartridge deck (904) during such longitudinal translation of adjunct (930) to inhibit snagging of staples (80) by nodules (932).

It will be appreciated that adjunct (930) may be released from staple cartridge deck (904) by separated, transversely-opposed segments of rail (940) when rail (940) is in the severed state. In the severed state (not shown), abutment surfaces (950a, 950b) of lower detents (946a, 946b) may disengage the respective bottom surfaces (920) of cartridge body (902) to thereby release adjunct (930) from staple cartridge deck (904). Rail (940) of the present version is configured to passively release adjunct (930) from staple cartridge deck (904) after firing of staple cartridge (900) and the resulting severing of lower bridge (956) in response to separation of end effector (50) from the stapled tissue. More particularly, staple cartridge deck (904) may be lowered downwardly relative to adjunct (930) during such separation of end effector (50) from the stapled tissue and may urge the respective lower detents (946a, 946b) transversely inwardly for disengaging abutment surfaces (950a, 950b) from the respective bottom surfaces (920). In some versions, lower detents (946a, 946b) may be resiliently biased transversely inwardly when lower bridge (956) is severed, such that rail (940) may be configured to actively release adjunct (930) from staple cartridge deck (904) in response to firing of staple cartridge (900).

While rail (940) has been described as being incorporated into compressible monolithic adjunct (930), it will be appreciated that rail (940) may just as easily be incorporated into a multi-layer adjunct similar to buttress assemblies (110, 112) described above in connection with FIGS. 7-9.

Figure 22:
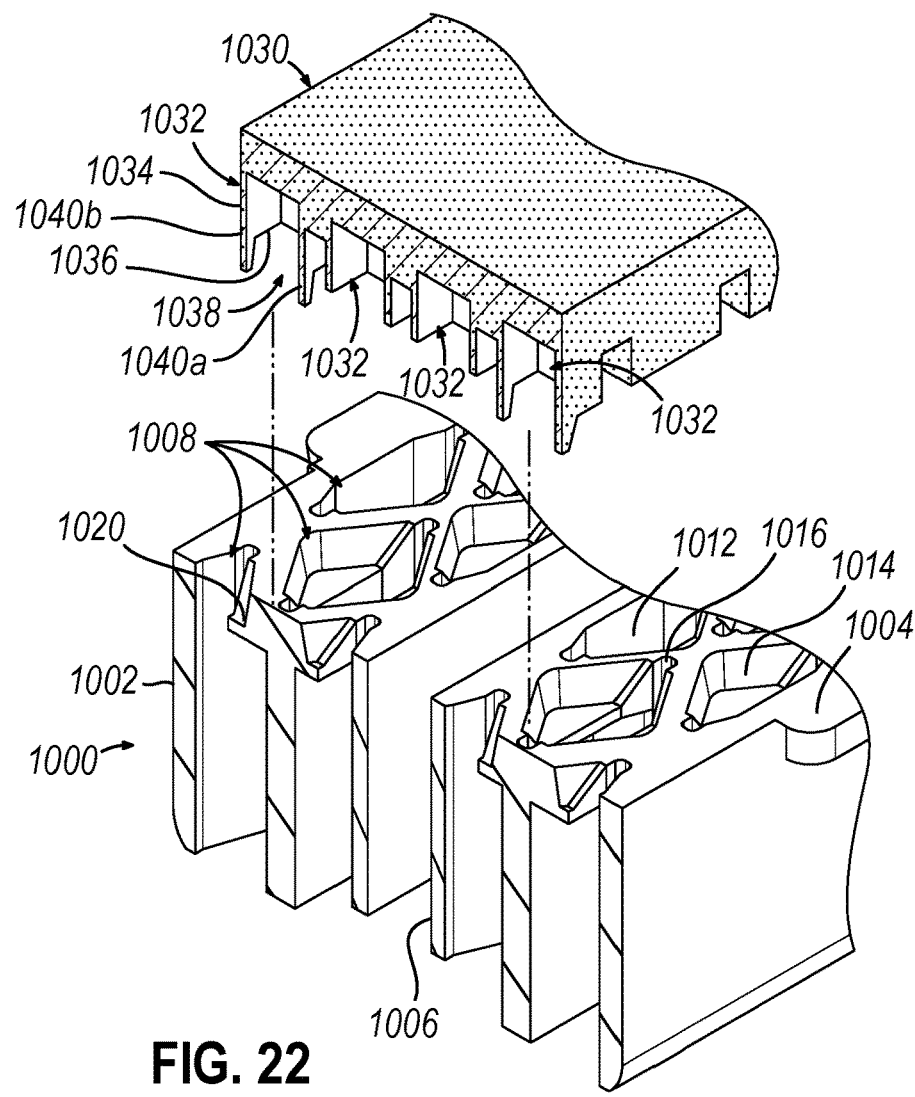
FIG. 22 depicts a cross-sectional perspective view of another exemplary staple cartridge in combination with another exemplary adjunct, showing the adjunct positioned above the staple cartridge with deflectable attachment features of the adjunct aligned with respective sidewalls of the staple cartridge.
Figure 23:
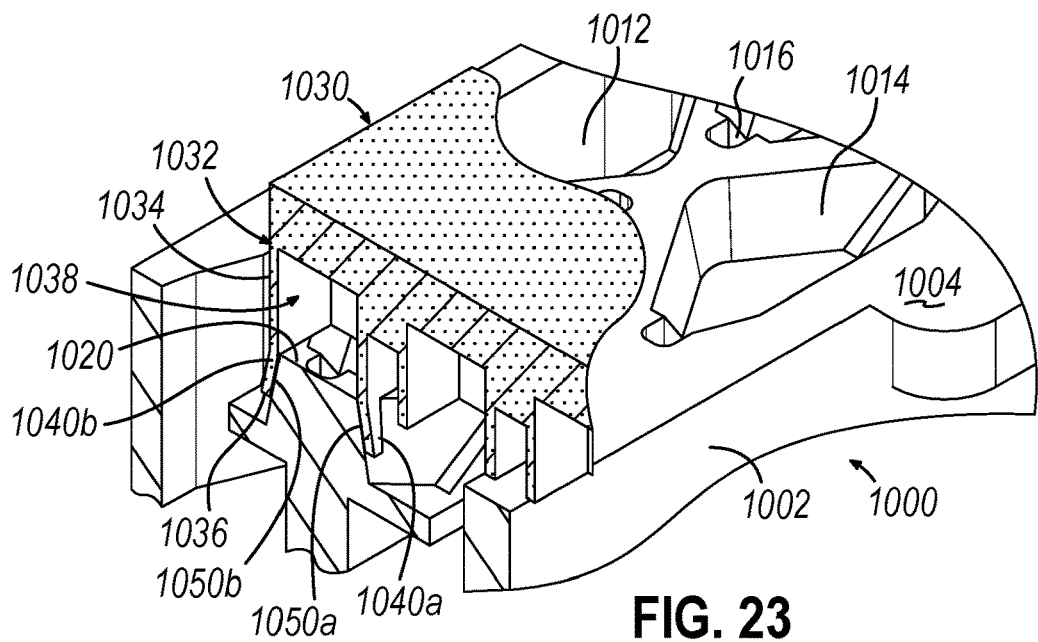
FIG. 23 depicts a magnified cross-sectional perspective view of the cartridge and adjunct of FIG. 22, showing the deflectable attachment features of the adjunct engaged with a sidewall of the staple cartridge for attaching the adjunct to the staple cartridge.

H. Exemplary Adjunct with Integral Attachment Features for Engaging Sidewalls of Cartridge Below Adjunct Nodules FIGS. 22-23 show another exemplary compressible monolithic adjunct (1030) configured for releasable attachment to a staple cartridge (1000). Staple cartridge (1000) and adjunct (1030) are configured for use with end effector (50) and are similar to staple cartridge (200) and adjunct (230) described above except as otherwise described below. In this regard, staple cartridge (1000) includes a cartridge body (1002) having an upwardly facing deck (1004), an elongate slot (1006) extending along a central axis of cartridge body (1002) and opening upwardly through deck (1004), and a plurality of staple openings (1008) extending through deck (1004) on each side of elongate slot (1006). Each staple opening (1008) slidably houses an unformed staple (not shown), similar to staple (80), and a respective staple driver (not shown) configured to drive the staple outwardly toward anvil (56) to be formed. A lower tray (not shown) of staple cartridge (1000) retains the staples and staple drivers within cartridge body (1002). Cartridge body (1002) of the present example further includes a plurality of upwardly-opening recesses (1012, 1014, 1016) formed in deck (1004) and having base surfaces through which staple openings (1008) extend. More specifically, on each side of elongate slot (1006), deck (1004) includes an inner row of triangular recesses (1012) each having a medial apex that points transversely away from elongate slot (1006); an outer row of triangular recesses (1014) each having a medial apex that points transversely toward elongate slot (1006); and a middle row of diamond-shaped recesses (1016) each having an inner medial apex that points transversely toward elongate slot (1006) and an opposed outer medial apex that points transversely away from elongate slot (1006). In the example shown, a sidewall (1020) is defined between each medial apex of the inner row of triangular recesses (1012) and an adjacent medial apex of the outer row of triangular recesses (1014), and is configured to facilitate releasable attachment of an adjunct, such as adjunct (1030), to staple cartridge deck (1004), as described in greater detail below.

Adjunct (1030) has a plurality of three-dimensional, resiliently compressible nodules (1032) that are integrally connected with one another in a plurality of linear arrays defining a lattice structure having an elongate rectangular shape in a manner similar to that described above in connection with FIGS. 10-12. Each nodule (1032) of the present example has a generally cuboid shape defining four side surfaces (1034), a lower surface (1036), and an opening (1038) in lower surface (336) that extends along a vertical central axis of nodule (1032) and defines an open, hollow interior of nodule (1032).

In the example shown, adjunct (1030) further includes a plurality of attachment features in the form of pairs of deflectable tabs (1040a, 1040b) coupled to transversely-outer nodules (1032) and configured to collectively at least partially receive sidewalls (1020). Tabs (1040a, 1040b) of each pair extend generally downwardly from the lower surface (1036) of a respective nodule (1032) and include a generally vertically-extending gripping surface (1050a, 1050b) for selectively engaging a respective side surface of the corresponding sidewall (1020) of cartridge body (1002).

Tabs (1040a, 1040b) of the present version are flexibly cantilevered from respective nodules (1032) such that tabs (1040a, 1040b) are deflectable relative to each other in the transverse direction between a disengaged state (FIG. 22) and an engaged state (FIG. 23). In some versions, tabs (1040a, 1040b) may be resiliently biased toward the disengaged state. In addition, or alternatively, any one or more of nodules (1032) and/or tabs (1040a, 1040b) may be integrally formed together as a unitary piece. For example, any one or more of nodules (1032) and/or tabs (1040a, 1040b) may be 3D-printed together. In some versions, tabs (1040a, 1040b) may be constructed of a different material than that of nodules (1032).

As shown in FIG. 22, adjunct (1030) may be initially positioned over staple cartridge deck (1004) with sidewalls (1020) aligned in a vertical direction with the spaces between the corresponding tabs (1040a, 1040b), such that the side surfaces of sidewalls (1020) may engage respective gripping surfaces (1050a, 1050b) for deflecting tabs (1040a, 1040b) slightly transversely away from the respective sidewalls (1020) during attachment of adjunct (1030) to staple cartridge deck (1004) to facilitate insertion of sidewalls (1020) between respective pairs of tabs (1040a, 1040b), with tabs (1040a, 1040b) resiliently biased against the respective sidewalls (1020) to provide a friction fit between tabs (1040a, 1040b) and sidewalls (1020).

As shown in FIG. 23, adjunct (1030) may be selectively attached to staple cartridge deck (1004) via tabs (1040a, 1040b) when tabs (1040a, 1040b) are in the engaged state. In the illustrated engaged state, gripping surfaces (1050a, 1050b) of tabs (1040a, 1040b) engage respective side surfaces of sidewalls (1020) to thereby attach adjunct (1030) to staple cartridge deck (1004). Tabs (1040a, 1040b) of the present version are configured to passively release adjunct (1030) from staple cartridge deck (1004) in response to separation of end effector (50) from the stapled tissue. More particularly, staple cartridge deck (1004) may be lowered downwardly relative to adjunct (1030) during such separation of end effector (50) from the stapled tissue and may urge sidewalls (1020) downwardly from the space between the respective tabs (1040a, 1040b) for disengaging gripping surfaces (1050a, 1050b) from the side surfaces of the respective sidewalls (1020).

Figure 24A:
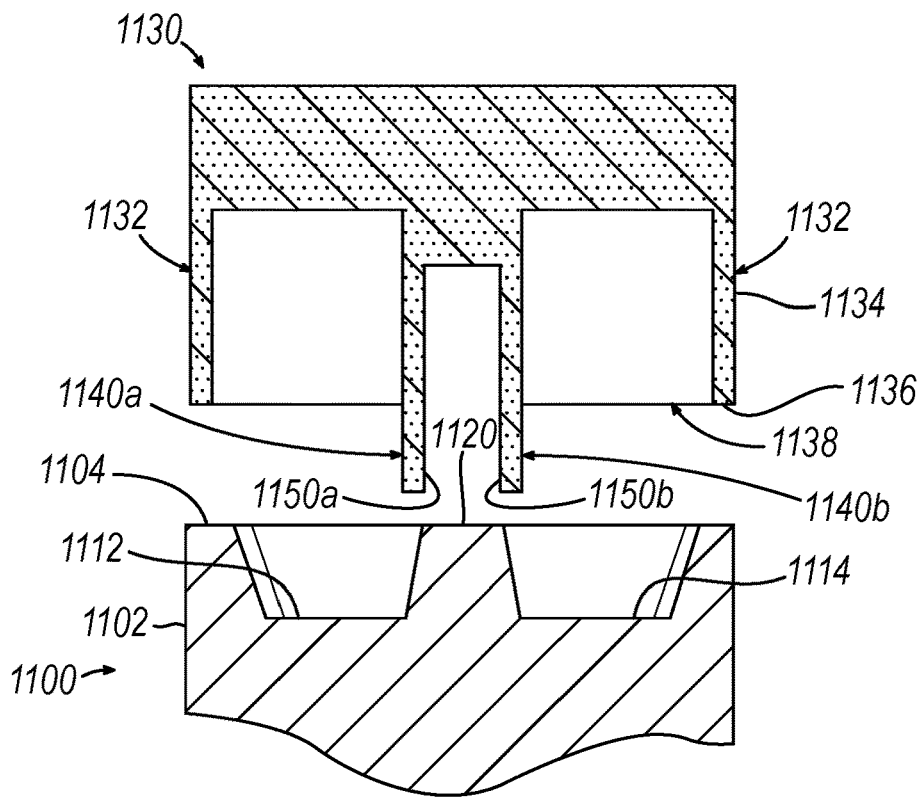
FIG. 24A depicts a cross-sectional end view of another exemplary staple cartridge in combination with another exemplary adjunct, showing the adjunct positioned above the staple cartridge with deflectable attachment features of the adjunct aligned with a respective sidewall of the staple cartridge.
Figure 24B:
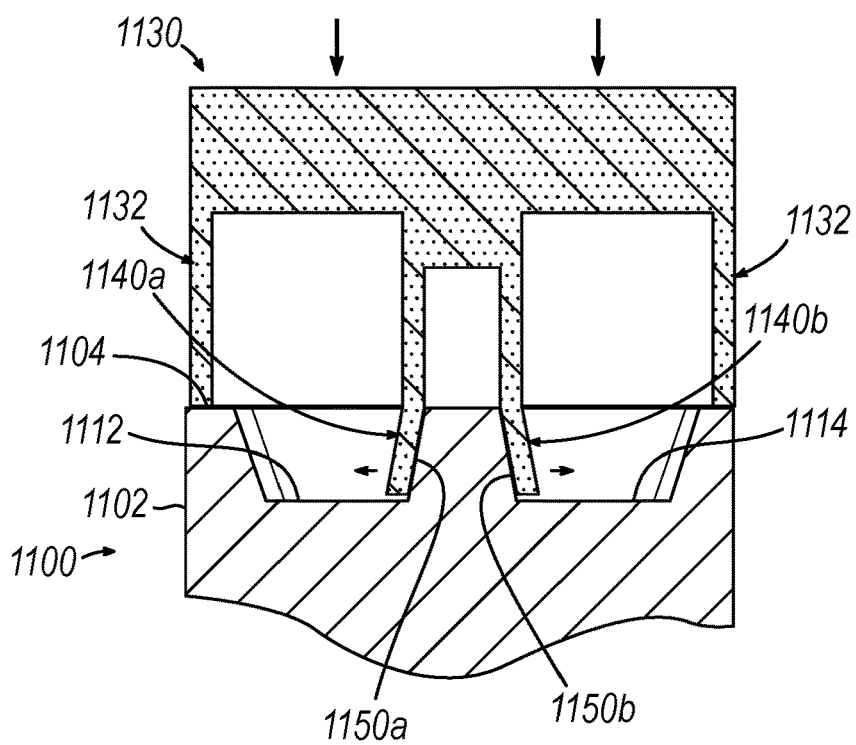
FIG. 24B depicts a cross-sectional end view of the cartridge and adjunct of FIG. 24A, showing the deflectable attachment features of the adjunct engaged with the sidewall of the staple cartridge for attaching the adjunct to the staple cartridge.

I. Exemplary Adjunct with Integral Attachment Features for Engaging Sidewalls of Cartridge Between Adjunct Nodules FIGS. 24A-24B show another exemplary compressible monolithic adjunct (1130) configured for releasable attachment to a staple cartridge (1100). Staple cartridge (1100) and adjunct (1130) are configured for use with end effector (50) and are similar to staple cartridge (200) and adjunct (230) described above except as otherwise described below. In this regard, staple cartridge (1100) includes a cartridge body (1102) having an upwardly facing deck (1104), an elongate slot (not shown) extending along a central axis of cartridge body (1102) and opening upwardly through deck (1104), and a plurality of staple openings (not shown) extending through deck (1104) on each side of the elongate slot. Each staple opening slidably houses an unformed staple (not shown), similar to staple (80), and a respective staple driver (not shown) configured to drive the staple outwardly toward anvil (56) to be formed. A lower tray (not shown) of staple cartridge (1100) retains the staples and staple drivers within cartridge body (1102). Cartridge body (1102) of the present example further includes a plurality of upwardly-opening recesses (1112, 1114) formed in deck (1104) and having base surfaces through which the staple openings extend. More specifically, on each side of the elongate slot, deck (1104) includes an inner row of triangular recesses (1112) each having a medial apex that points transversely away from the elongate slot; and an outer row of triangular recesses (1114) each having a medial apex that points transversely toward the elongate slot. In the example shown, a sidewall (1120) is defined between each medial apex of the inner row of triangular recesses (1112) and an adjacent medial apex of the outer row of triangular recesses (1114), and is configured to facilitate releasable attachment of an adjunct, such as adjunct (1130), to staple cartridge deck (1104), as described in greater detail below.

Adjunct (1130) has a plurality of three-dimensional, resiliently compressible nodules (1132) that are integrally connected with one another in a plurality of linear arrays defining a lattice structure having an elongate rectangular shape in a manner similar to that described above in connection with FIGS. 10-12. Each nodule (1132) of the present example has a generally cuboid shape defining four side surfaces (1134), a lower surface (1136), and an opening (1138) in lower surface (1136) that extends along a vertical central axis of nodule (1132) and defines an open, hollow interior of nodule (1132).

In the example shown, adjunct (1130) further includes a plurality of attachment features in the form of pairs of deflectable tabs (1140a, 1140b) coupled to transversely-adjacent pairs of nodules (1132) and configured to collectively at least partially receive sidewalls (1120). Tabs (1140a, 1140b) of each pair extend generally downwardly from confronting inner sidewalls of transversely-adjacent nodules (1132) and include a generally vertically-extending gripping surface (1150a, 1150b) for selectively engaging a respective side surface of the corresponding sidewall (1120) of cartridge body (1102).

Tabs (1140a, 1140b) of the present version are flexibly cantilevered from respective nodules (1132) such that tabs (1140a, 1140b) are deflectable relative to each other in the transverse direction between a disengaged state (FIG. 24A) and an engaged state (FIG. 24B). In some versions, tabs (1140a, 1140b) may be resiliently biased toward the disengaged state. In addition, or alternatively, any one or more of nodules (1132) and/or tabs (1140a, 1140b) may be integrally formed together as a unitary piece. For example, any one or more of nodules (1132) and/or tabs (1140a, 1140b) may be 3D-printed together. In some versions, tabs (1140a, 1140b) may be constructed of a different material than that of nodules (1132).

As shown in FIG. 24A, adjunct (1130) may be initially positioned over staple cartridge deck (1104) with sidewalls (1120) aligned in a vertical direction with the spaces between the corresponding tabs (1140a, 1140b), such that the side surfaces of sidewalls (1120) may engage respective gripping surfaces (1150a, 1150b) for deflecting tabs (1140a, 1140b) slightly transversely away from the respective sidewalls (1120) during attachment of adjunct (1130) to staple cartridge deck (1104) to facilitate insertion of sidewalls (1120) between respective pairs of tabs (1140a, 1140b), with tabs (1140a, 1140b) resiliently biased against the respective sidewalls (1120) to provide a friction fit between tabs (1140a, 1140b) and sidewalls (1120).

As shown in FIG. 24B, adjunct (1130) may be selectively attached to staple cartridge deck (1104) via tabs (1140a, 1140b) when tabs (1140a, 1140b) are in the engaged state. In the illustrated engaged state, gripping surfaces (1150a, 1150b) of tabs (1140a, 1140b) engage respective side surfaces of sidewalls (1120) to thereby attach adjunct (1130) to staple cartridge deck (1104). Tabs (1140a, 1140b) of the present version are configured to passively release adjunct (1130) from staple cartridge deck (1104) in response to separation of end effector (50) from the stapled tissue. More particularly, staple cartridge deck (1104) may be lowered downwardly relative to adjunct (1130) during such separation of end effector (50) from the stapled tissue and may urge sidewalls (1120) downwardly from the space between the respective tabs (1140a, 1040b) for disengaging gripping surfaces (1150a, 1150b) from the side surfaces of the respective sidewalls (1120).

Figure 25A:
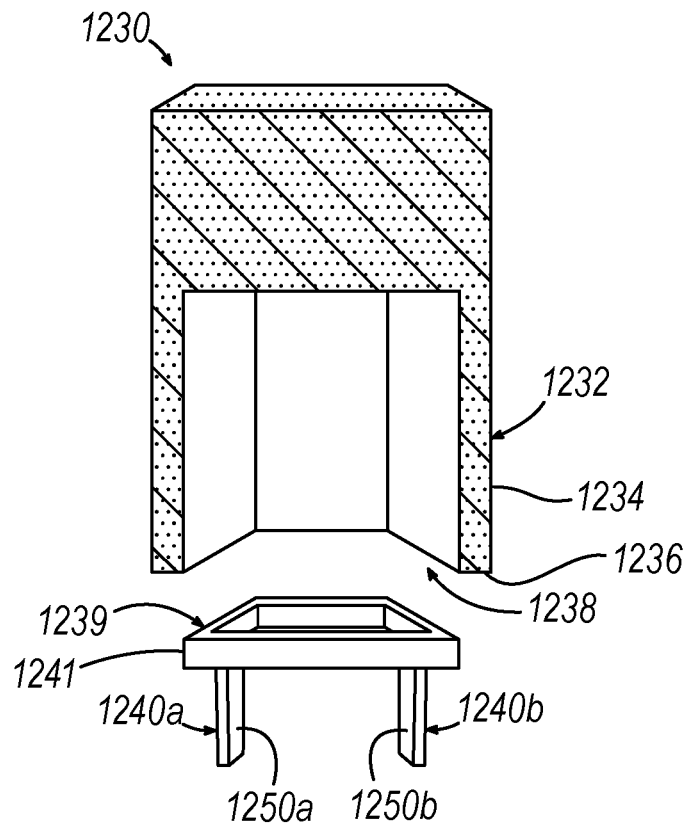
FIG. 25A depicts a partial exploded cross-sectional perspective view of another exemplary adjunct, showing a coupler of the adjunct separated from a nodule of the adjunct.
Figure 25B:
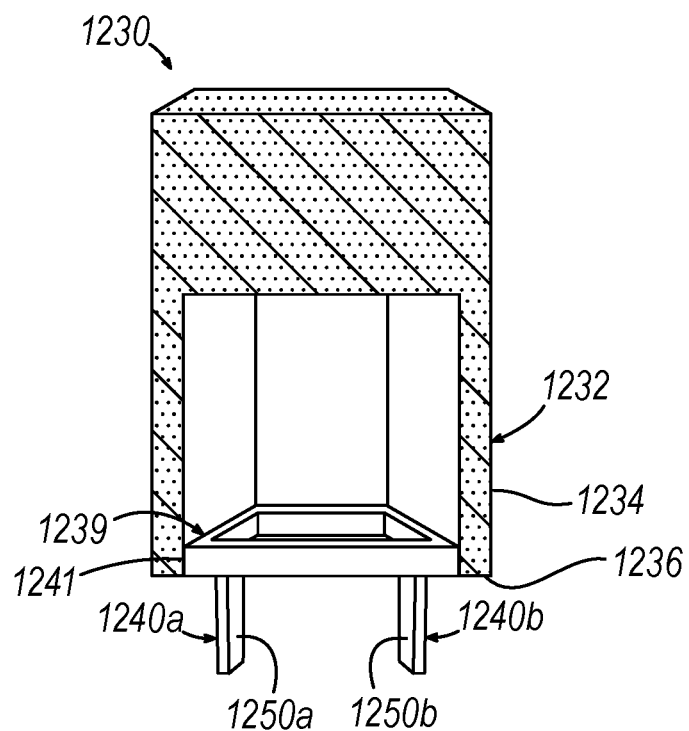
FIG. 25B depicts a partial exploded cross-sectional perspective view of the adjunct of FIG. 25A, showing the coupler fixedly secured to the nodule.

J. Exemplary Adjunct with Separately-Formed Attachment Features for Engaging Sidewalls of Cartridge Below Adjunct Nodules FIGS. 25A-25B show a portion of another exemplary compressible monolithic adjunct (1230) configured for releasable attachment to a staple cartridge (not shown) similar to staple cartridge (200). Adjunct (1230) is configured for use with end effector (50) and is similar adjunct (230) described above except as otherwise described below. In this regard, adjunct has a plurality of three-dimensional, resiliently compressible nodules (1232) (one shown) that are integrally connected with one another in a plurality of linear arrays defining a lattice structure having an elongate rectangular shape in a manner similar to that described above in connection with FIGS. 10-12. Each nodule (1232) of the present example has a generally cuboid shape defining four side surfaces (1234), a lower surface (1236), and an opening (1238) in lower surface (1236) that extends along a vertical central axis of nodule (1232) and defines an open, hollow interior of nodule (1232).

In the example shown, adjunct (1230) further includes a coupler (1239) having a plurality of attachment features in the form of a pair of deflectable tabs (1240a, 1240b) coupled to nodule (1232) and configured to collectively at least partially receive a sidewall of cartridge body (202) of staple cartridge (200), such as a sidewall defined between each medial apex of the inner row of triangular recesses (212) and an adjacent medial apex of the outer row of triangular recesses (214). Tabs (1240a, 1240b) of each pair extend generally downwardly from an upper frame (1241) of coupler (1239), which is fixedly secured to nodule (1232) within the lower opening (1238) of a respective nodule (1232), and include a generally vertically-extending gripping surface (1250a, 1250b) for selectively engaging a respective side surface of the corresponding sidewall of cartridge body (202).

Tabs (1240a, 1240b) of the present version are flexibly cantilevered from upper frame (1241) such that tabs (1240a, 1240b) are deflectable relative to each other in the transverse direction between the illustrated disengaged state and an engaged state (not shown). In some versions, tabs (1240a, 1240b) may be resiliently biased toward the disengaged state. In any event, nodule (1232) and coupler (1239) may be separately formed from each other as distinct pieces and secured to each other in any suitable manner. For example, upper frame (1241) may be adhered to an internal surface of nodule (1232) within lower opening (1238). In some versions, coupler (1239) may be constructed of a different material than that of nodule (1232).

It will be appreciated that adjunct (1230) may be selectively attached to staple cartridge deck (204) via tabs (1240a, 1240b) in a manner similar to that described above in connection with FIGS. 22-23, for example.

Figure 26:
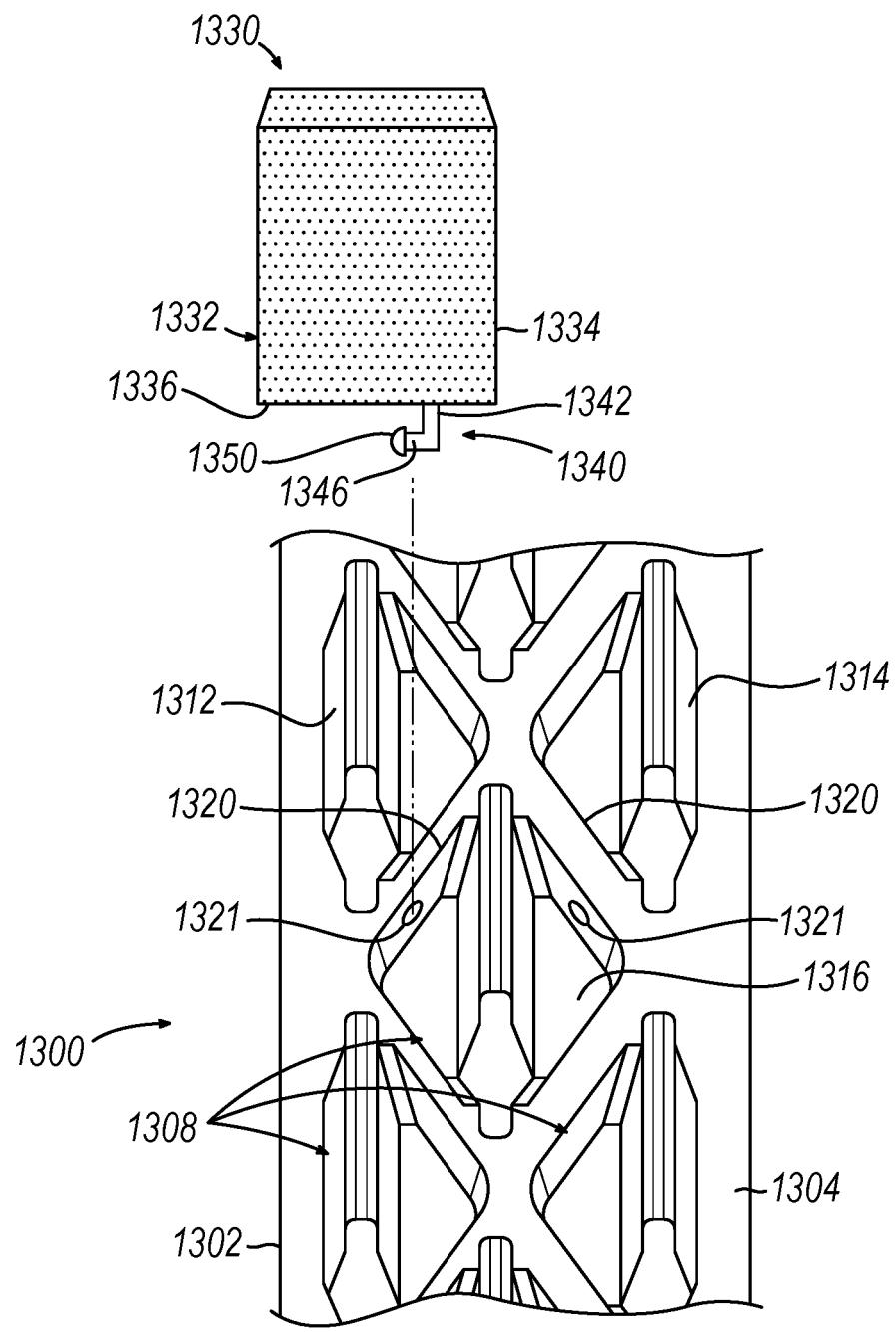
FIG. 26 depicts a partial exploded perspective view of another exemplary staple cartridge in combination with another exemplary adjunct, showing the adjunct positioned above the staple cartridge with a deflectable attachment feature of the adjunct aligned with a respective sidewall bore of the staple cartridge.

K. Exemplary Adjunct with Deflectable Attachment Features for Engaging Sidewall Bores of Cartridge FIGS. 26-27B show a portion of another exemplary compressible monolithic adjunct (1330) configured for releasable attachment to a staple cartridge (1300). Staple cartridge (1300) and adjunct (1330) are configured for use with end effector (50) and are similar to staple cartridge (200) and adjunct (230) described above except as otherwise described below. In this regard, staple cartridge (1300) includes a cartridge body (1302) having an upwardly facing deck (1304), an elongate slot (not shown) extending along a central axis of cartridge body (1302) and opening upwardly through deck (1304), and a plurality of staple openings (1308) extending through deck (1304) on each side of elongate slot (1306). Each staple opening (1308) slidably houses an unformed staple (not shown), similar to staple (80), and a respective staple driver (not shown) configured to drive the staple outwardly toward anvil (56) to be formed. A lower tray (not shown) of staple cartridge (1300) retains the staples and staple drivers within cartridge body (1302). Cartridge body (1302) of the present example further includes a plurality of upwardly-opening recesses (1312, 1314, 1316) formed in deck (1304) and having base surfaces through which staple openings (1308) extend. More specifically, on each side of the elongate slot, deck (1304) includes an inner row of triangular recesses (1312) each having a medial apex that points transversely away from the elongate slot; an outer row of triangular recesses (1314) each having a medial apex that points transversely toward the elongate slot; and a middle row of diamond-shaped recesses (1316) each having an inner medial apex that points transversely toward the elongate slot and an opposed outer medial apex that points transversely away from the elongate slot. In the example shown, at least one sidewall (1320) is defined between each diamond-shaped recess (1316) and each of the adjacent triangular recesses (1312, 1314). A bore (1321) extends through each sidewall (1320) and is configured to facilitate releasable attachment of an adjunct, such as adjunct (1330), to staple cartridge deck (1304), as described in greater detail below.

Adjunct (1330) has a plurality of three-dimensional, resiliently compressible nodules (1332) (one shown) that are integrally connected with one another in a plurality of linear arrays defining a lattice structure having an elongate rectangular shape in a manner similar to that described above in connection with FIGS. 10-12. Each nodule (1332) of the present example has a generally cuboid shape defining four side surfaces (1334), a lower surface (1336), and an opening (not shown) in lower surface (1336) that extends along a vertical central axis of nodule (1332) and defines an open, hollow interior of nodule (1332).

In the example shown, adjunct (1330) further includes at least one attachment feature in the form of at least one deflectable latch (1340) coupled to nodule (1332) and configured to be at least partially received within a respective diamond-shaped recess (1316). Each latch (1340) includes a beam (1342) extending generally downwardly from a lower portion of nodule (1332) and a lower detent (1346) extending generally transversely from a lower portion of beam (1342) for selectively engaging a respective bore (1321)) of cartridge body (1302). In the example shown, each lower detent (1346) terminates at a bulbous head (1350), the purpose of which is described below.

Beam (1342) of latch (1340) of the present version is flexibly cantilevered from nodule (1332) such that latch (1340a, 1340b) is deflectable in the transverse direction between a latched state (FIG. 27A) and an unlatched state (FIG. 27B). In some versions, latch (1340) may be resiliently biased toward the unlatched state. In addition, or alternatively, nodule (1332) and latch (1340) may be integrally formed together as a unitary piece. For example, nodule (1332) and latch (1340) may be 3D-printed together. In some versions, latch (1340) may be constructed of a different material than that of nodule (1332).

Figure 27A:
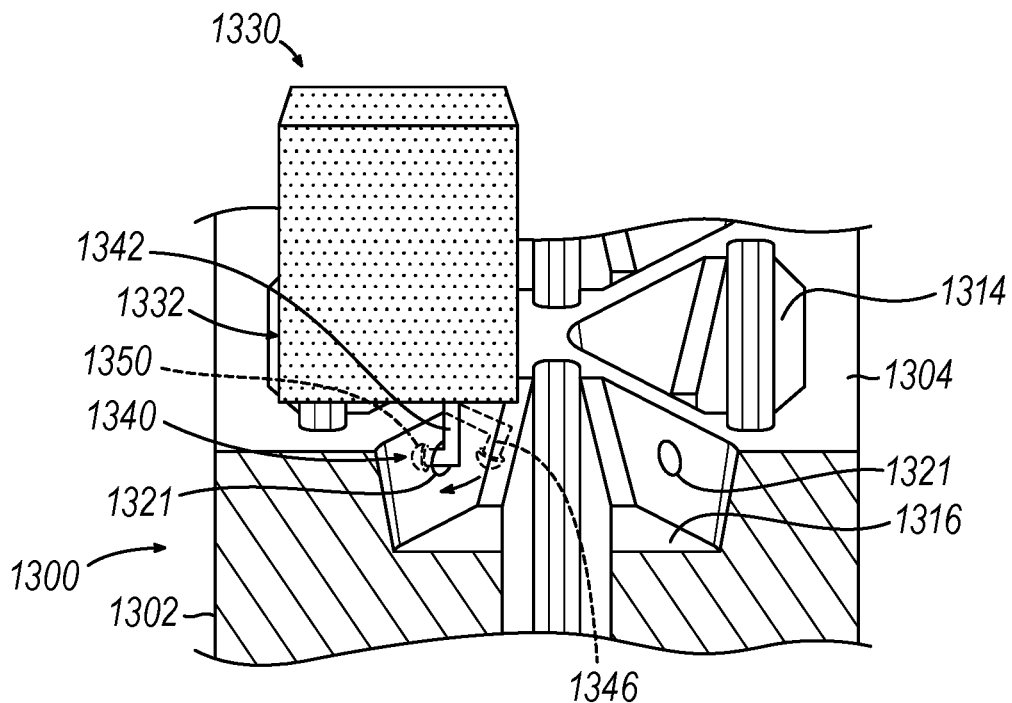
FIG. 27A depicts a partial cross-sectional perspective view of the staple cartridge and adjunct of FIG. 26, showing the deflectable attachment feature of the adjunct engaged with the sidewall bore of the staple cartridge for attaching the adjunct to the staple cartridge.
Figure 27B:
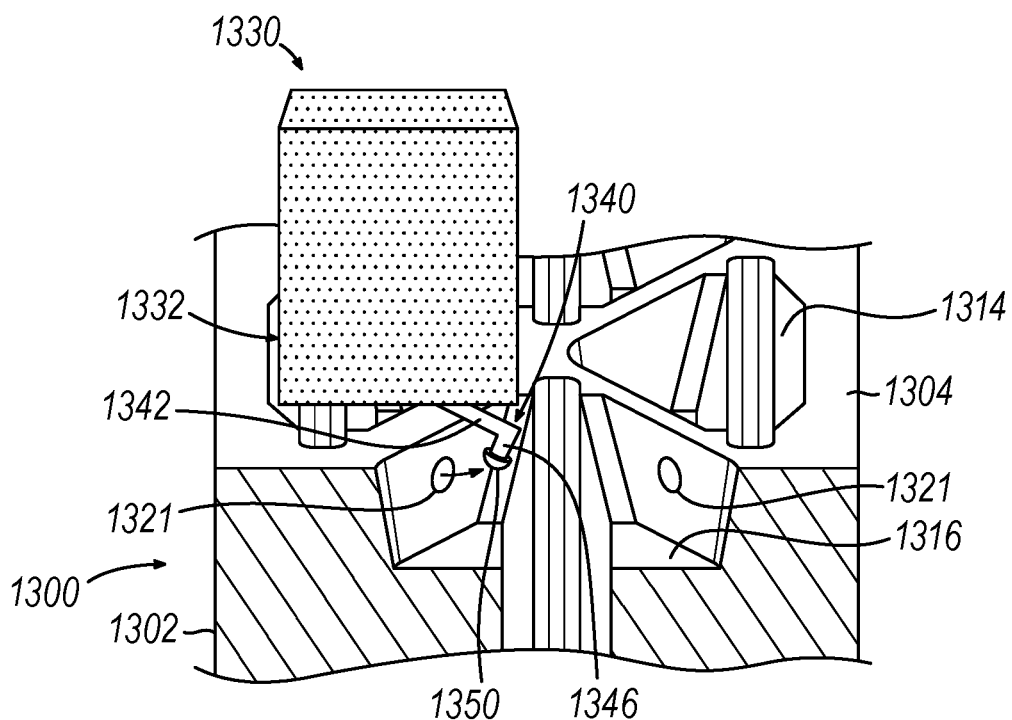
FIG. 27B depicts a partial cross-sectional perspective view of the staple cartridge and adjunct of FIG. 26, showing the deflectable attachment feature of the adjunct disengaged from the sidewall bore of the staple cartridge for releasing the adjunct from the staple cartridge.

As shown in FIG. 27A, adjunct (1330) may be selectively attached to staple cartridge deck (1304) via latch (1340) when latch (1340) is in the latched state. In the illustrated latched state, head (1350) of lower detent (1346) engages a respective bore (1321) of cartridge body (1302) to thereby attach adjunct (1330) to staple cartridge deck (1304). In some versions, head (1350) may be slightly compressed by bore (1321) during attachment of adjunct (1330) to staple cartridge deck (1304) to facilitate insertion of head (1350) into bore (1321), with head (1350) subsequently resiliently expanded to grip bore (1321) and/or to grip a surface of sidewall (1320) opposite beam (1342).

As shown in FIG. 27B, adjunct (1330) may be released from staple cartridge deck (1304) by latch (1340) when latch (1340) is in the unlatched state. In the illustrated unlatched state, head (1350) of lower detent (1346) disengages the respective bore (1321) of cartridge body (1302) to thereby release adjunct (1330) from staple cartridge deck (1304). Latch (1340) of the present version is configured to passively release adjunct (1330) from staple cartridge deck (1304) in response to separation of end effector (50) from the stapled tissue. More particularly, staple cartridge deck (1304) may be lowered downwardly relative to adjunct (1330) during such separation of end effector (50) from the stapled tissue and may urge bore (1321) downwardly away from latch (1340) for disengaging head (1350) from bore (1321) and/or the surface of sidewall (1320) opposite beam (1342).

Figure 28A:
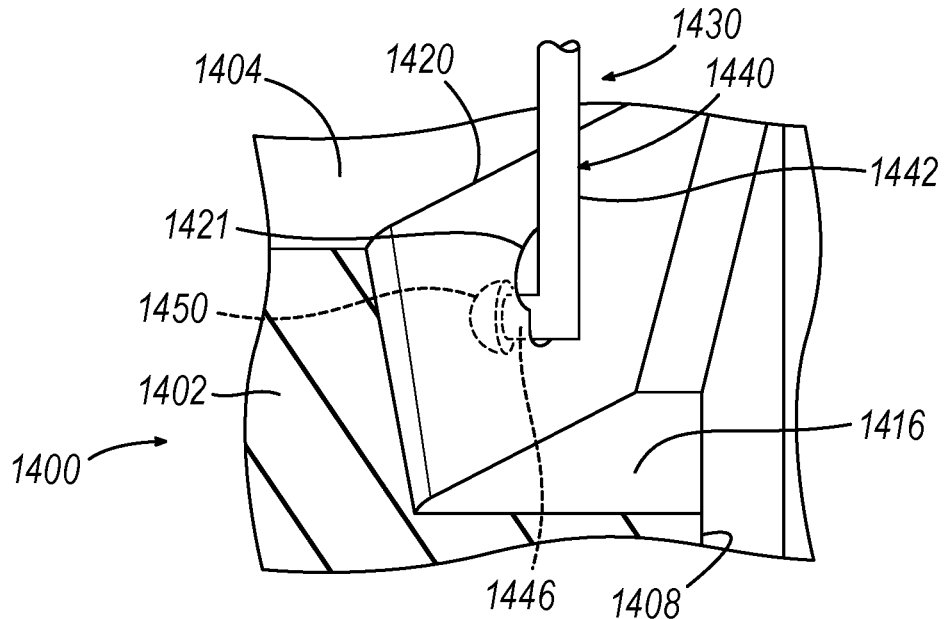
FIG. 28A depicts a partial cross-sectional perspective view of another exemplary staple cartridge in combination with another exemplary adjunct, showing an undeflectable attachment feature of the adjunct engaged with a sidewall keyhole slot of the staple cartridge for attaching the adjunct to the staple cartridge.
Figure 28B:
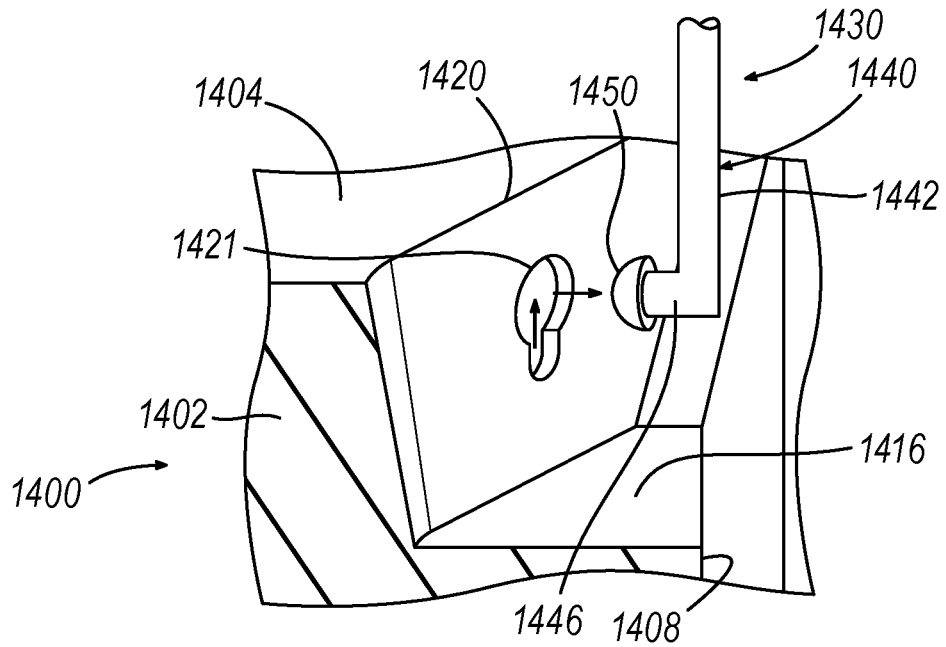
FIG. 28B depicts a partial cross-sectional perspective view of the staple cartridge and adjunct of FIG. 28A, showing the undeflectable attachment feature of the adjunct disengaged from the sidewall keyhole slot of the staple cartridge for releasing the adjunct from the staple cartridge.

L. Exemplary Adjunct with Attachment Features for Engaging Sidewall Keyhole Slots of Cartridge FIGS. 28A-28B show a portion of another exemplary compressible monolithic adjunct (1430) configured for releasable attachment to a staple cartridge (1400). Staple cartridge (1400) and adjunct (1430) are configured for use with end effector (50) and are similar to staple cartridge (200) and adjunct (230) described above except as otherwise described below. In this regard, staple cartridge (1400) includes a cartridge body (1402) having an upwardly facing deck (1404), an elongate slot (not shown) extending along a central axis of cartridge body (1402) and opening upwardly through deck (1404), and a plurality of staple openings (1408) extending through deck (1404) on each side of elongate slot (1406). Each staple opening (1408) slidably houses an unformed staple (not shown), similar to staple (80), and a respective staple driver (not shown) configured to drive the staple outwardly toward anvil (56) to be formed. A lower tray (not shown) of staple cartridge (1400) retains the staples and staple drivers within cartridge body (1402). Cartridge body (1402) of the present example further includes a plurality of upwardly-opening recesses (1416)

formed in deck (1404) and having base surfaces through which staple openings (1408) extend. More specifically, on each side of the elongate slot, deck (1404) includes an inner row of triangular recesses (not shown) each having a medial apex that points transversely away from the elongate slot; an outer row of triangular recesses (not shown) each having a medial apex that points transversely toward the elongate slot; and a middle row of diamond-shaped recesses (1416) each having an inner medial apex that points transversely toward the elongate slot and an opposed outer medial apex that points transversely away from the elongate slot. In the example shown, at least one sidewall (1420) is defined between each diamond-shaped recess (1416) and each of the adjacent triangular recesses. A keyhole slot (1421) extends through each sidewall (1420) and is configured to facilitate releasable attachment of an adjunct, such as adjunct (1430), to staple cartridge deck (1404), as described in greater detail below.

Adjunct (1430) has a plurality of three-dimensional, resiliently compressible nodules (not shown), similar to nodules (332) described above, that are integrally connected with one another in a plurality of linear arrays defining a lattice structure having an elongate rectangular shape in a manner similar to that described above in connection with FIGS. 10-12. In the example shown, adjunct (1430) further includes at least one attachment feature in the form of at least one undeflectable latch (1440) coupled to a respective nodule and configured to be at least partially received within a respective diamond-shaped recess (1416). Each latch (1440) includes a beam (1442) extending generally downwardly from a lower portion of the nodule, and a lower detent (1446) extending generally transversely from a lower portion of beam (1442) for selectively engaging a respective keyhole slot (1421) of cartridge body (1402). In the example shown, each lower detent (1446) terminates at a bulbous head (1450), the purpose of which is described below.

Beam (1442) of latch (1440) of the present version is rigidly cantilevered from the respective nodule. In some versions, latch (1440) may be flexibly cantilevered from the nodule. In addition, or alternatively, the nodule and latch (1440) may be integrally formed together as a unitary piece. For example, the nodule and latch (1440) may be 3D-printed together. In some versions, latch (1440) may be constructed of a different material than that of the nodule.

As shown in FIG. 28A, adjunct (1430) may be selectively attached to staple cartridge deck (1404) via latch (1440) when latch (1340) is in a latched position. In the illustrated latched position, head (1450) of lower detent (1446) engages a lower narrow portion of keyhole slot (1421) of cartridge body (1402) to thereby attach adjunct (1430) to staple cartridge deck (1404). In some versions, head (1450) may be initially passed through an upper wide portion of keyhole slot (1421) during attachment of adjunct (1430) to staple cartridge deck (1404) to facilitate insertion of head (1450) into keyhole slot (1421), with head (1450) subsequently lowered toward the lower narrow portion of keyhole slot (1421) to grip the lower narrow portion of keyhole slot (1421) and/or to grip a surface of sidewall (1420) opposite beam (1442).

As shown in FIG. 27B, adjunct (1430) may be released from staple cartridge deck (1404) by latch (1440) when latch (1440) is in an unlatched position. In the illustrated unlatched position, head (1450) of lower detent (1446) disengages the lower narrow portion of the respective keyhole slot (1421) of cartridge body (1402) to thereby release adjunct (1430) from staple cartridge deck (1404). Latch (1440) of the present version is configured to passively release adjunct (1430) from staple cartridge deck (1404) in response to separation of end effector (50) from the stapled tissue. More particularly, staple cartridge deck (1404) may be lowered downwardly relative to adjunct (1430) during such separation of end effector (50) from the stapled tissue and may urge keyhole slot (1421) downwardly away from latch (1440) for disengaging head (1450) from the lower narrow portion of keyhole slot (1421) and/or the surface of sidewall (1420) opposite beam (1442).

Figure 29:
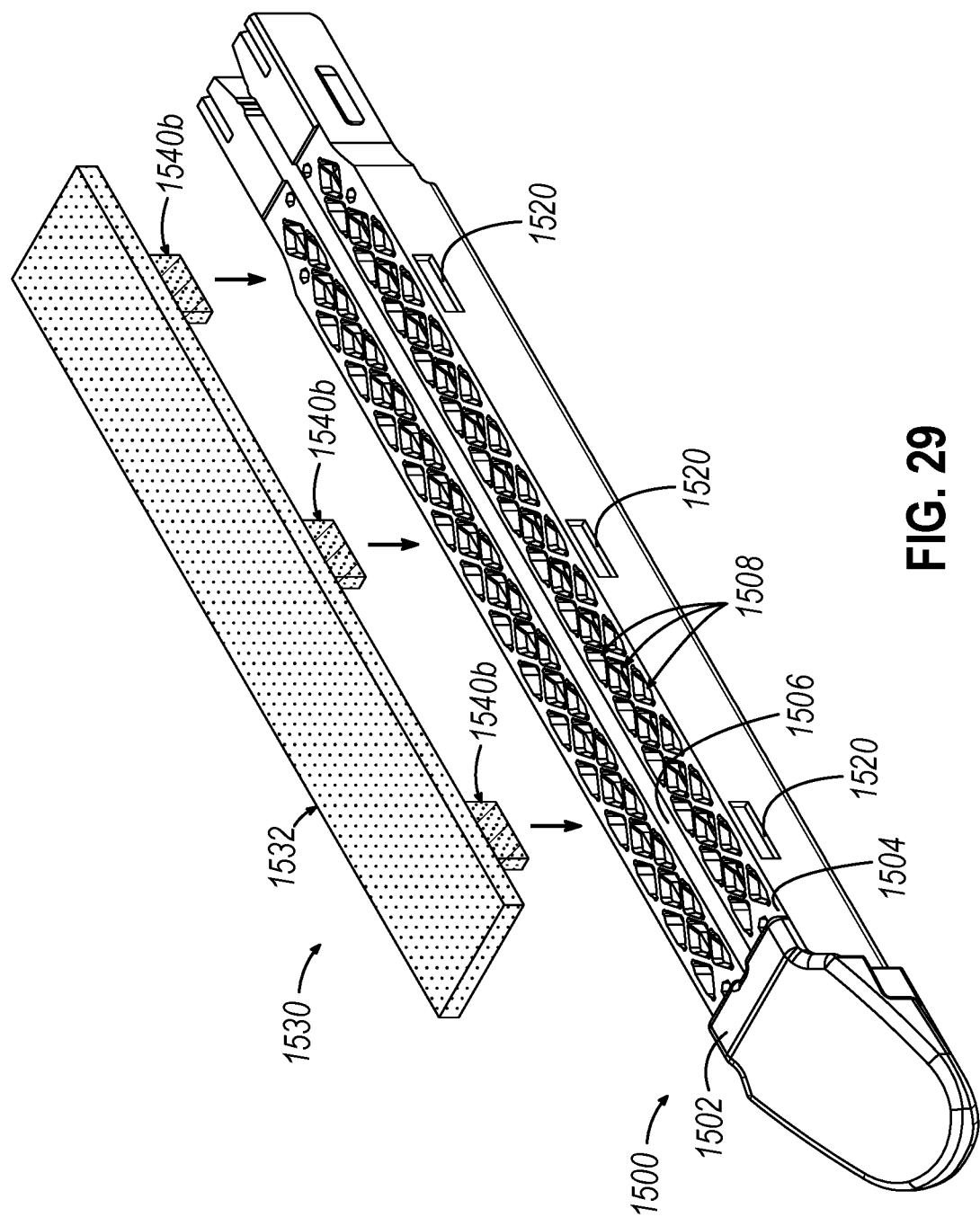
FIG. 29 depicts an exploded perspective view of another exemplary staple cartridge in combination with another exemplary adjunct, showing the adjunct positioned above the staple cartridge with moisture-sensitive foam attachment features of the adjunct aligned with respective transverse recesses of the staple cartridge.

M. Exemplary Adjunct with Foam Attachment Features for Engaging Lateral Recesses of Cartridge FIGS. 29-30F show another exemplary multi-layer adjunct (1530) configured for releasable attachment to a staple cartridge (1500). Staple cartridge (1500) and adjunct (1530) are configured for use with end effector (50) and are similar to staple cartridge (200) and buttress assemblies (110, 112) described above except as otherwise described below. In this regard, staple cartridge (1500) includes a cartridge body (1502) having an upwardly facing deck (1504), an elongate slot (1506) extending along a central axis of cartridge body (1502) and opening upwardly through deck (1504), and a plurality of staple openings (1508) extending through deck (1504) on each side of elongate slot (1506). Each staple opening (1508) slidably houses an unformed staple (not shown), similar to staple (80), and a respective staple driver (not shown) configured to drive the staple outwardly toward anvil (56) to be formed. A lower tray (not shown) of staple cartridge (1500) retains the staples and staple drivers within cartridge body (1502). Cartridge body (1502) of the present example further includes a plurality of transversely-opposed pairs of recesses (1520) each extending transversely inwardly from a transversely-outer side of a respective sidewall of cartridge body (1502) and configured to facilitate releasable attachment of an adjunct, such as adjunct (1530), to staple cartridge deck (1504), as described in greater detail below.

Adjunct (1530) includes a buttress body (1532) which comprises a strong yet flexible material configured to structurally support a line of staples (80). By way of example only, buttress body (1532) may comprise a composite polymeric foam layer having material properties configured to provide a tissue compensating effect. In other versions, buttress body (1532) may comprise a mesh of polyglactin 910 material by Ethicon, Inc. of Somerville, New Jersey. Alternatively, any other suitable materials or combinations of materials may be used in addition to or as an alternative to polyglactin 910 material to form buttress body (1532).

In the example shown, adjunct (1530) further includes a plurality of attachment features in the form of a plurality of transversely-opposed pairs of shape memory tabs (1540*a*, 1540*b*) coupled to transversely-outer sides of buttress body (1532) and configured to be at least partially received within respective recesses (1520). Each tab (1540*a*, 1540*b*) comprises a moisture-sensitive composite shape memory polymeric foam configured to have a relatively high stiffness when dry and a relatively low stiffness when wet. Tabs (1540*a*, 1540*b*) of the present version extend downwardly from respective transversely-outer sides of buttress body (1532) such that tabs (1540*a*, 1540*b*) are deformable relative to each other in the transverse direction when exposed to moisture.

Figure 30A:
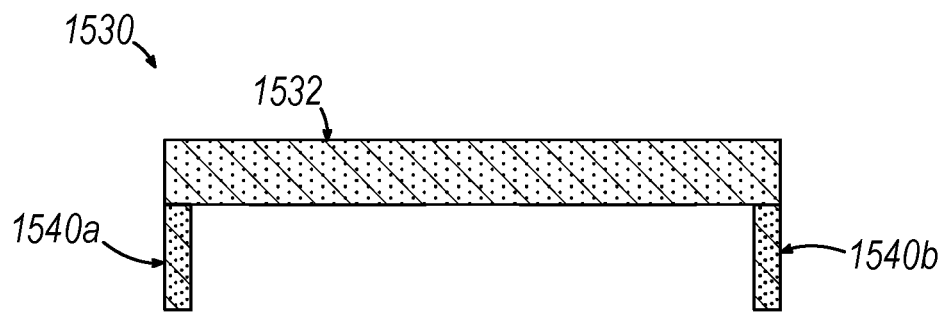
FIG. 30A depicts a cross-sectional end view of the adjunct of FIG. 29, showing the moisture-sensitive foam attachment features in a dry state.
Figure 30B:
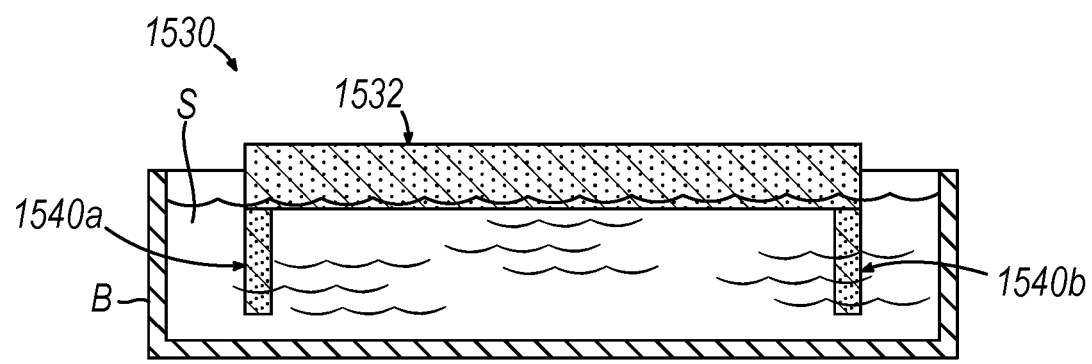
FIG. 30B depicts a cross-sectional end view of the adjunct of FIG. 29, showing the moisture-sensitive foam attachment features submerged in an aqueous solution to transition the moisture-sensitive foam attachment features from the dry state to a wet state.
Figure 30C:
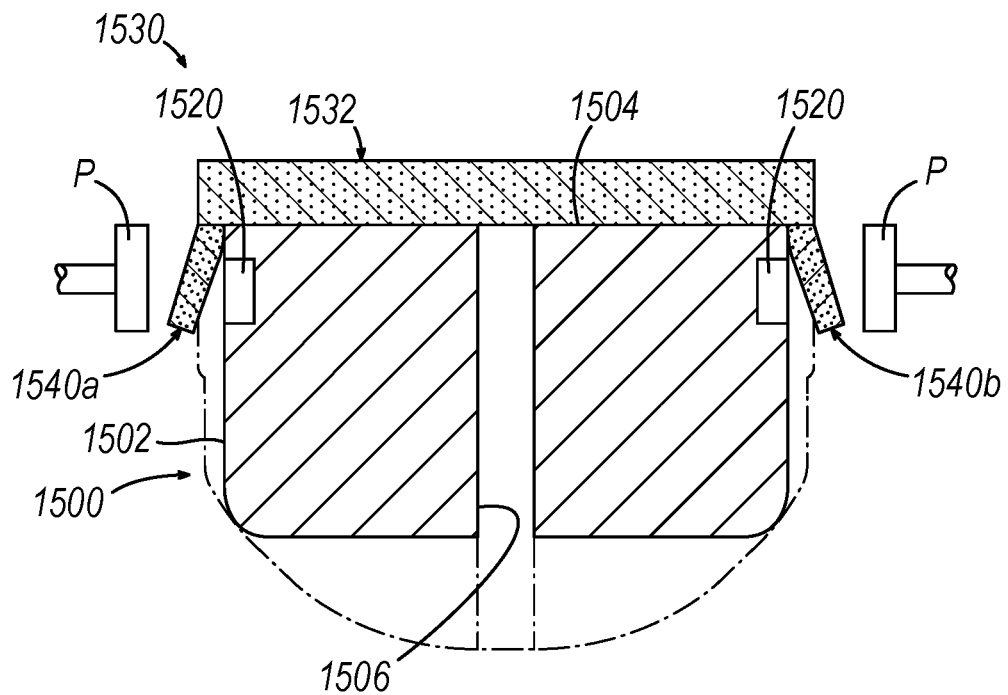
FIG. 30C depicts a cross-sectional end view of the adjunct of FIG. 29 positioned over another exemplary staple cartridge, showing the moisture-sensitive foam attachment features urged slightly transversely outwardly by the staple cartridge.
Figure 30D:
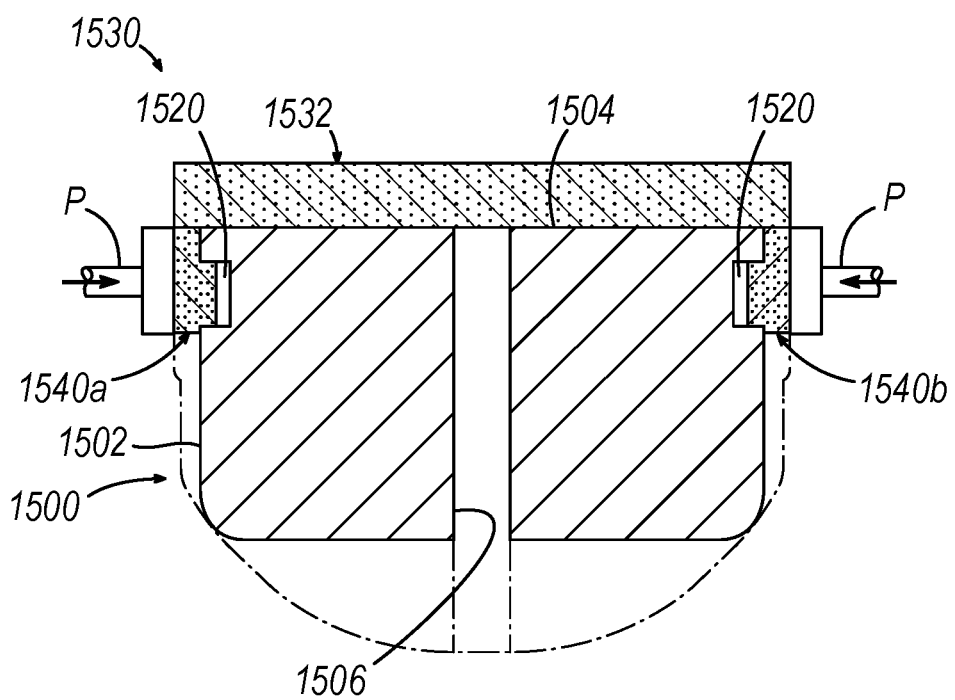
FIG. 30D depicts a cross-sectional end view of the adjunct of FIG. 29 positioned over the staple cartridge of FIG. 29, showing the moisture-sensitive foam attachment features pressed transversely inwardly into the transverse recesses by a pair of pushers.

As shown in FIG. 30A, tabs (1540*a*, 1540*b*) may initially be in a dry state in which tabs (1540*a*, 1540*b*) have a first stiffness and in which tabs (1540*a*, 1540*b*) are oriented generally orthogonally relative to buttress body (1532). As shown in FIG. 30B, tabs (1540a, 1540b) may subsequently be exposed to moisture, such as by submerging tabs (1540a, 1540b) into an aqueous solution (S) in a bath (B), to thereby transition tabs (1540a, 1540b) from the dry state to a wet state in which tabs (1540a, 1540b) have a second stiffness less than the first stiffness. As shown in FIG. 30C, adjunct (1530) may then be positioned over staple cartridge deck (1504) with tabs (1540a, 1540b) in the wet state such that tabs (1540a, 1540b) may be temporarily deflected slightly transversely outwardly by the respective sidewalls of cartridge body (1502). As shown in FIG. 30D, tabs (1540a, 1540b) may subsequently be urged transversely inwardly while in the wet state, such as by a pair of transversely-opposed pushers (P), such that at least a portion of each tab (1540a, 1540b) is deformed into the respective recess (1520) of cartridge body (1502).

Figure 30E:
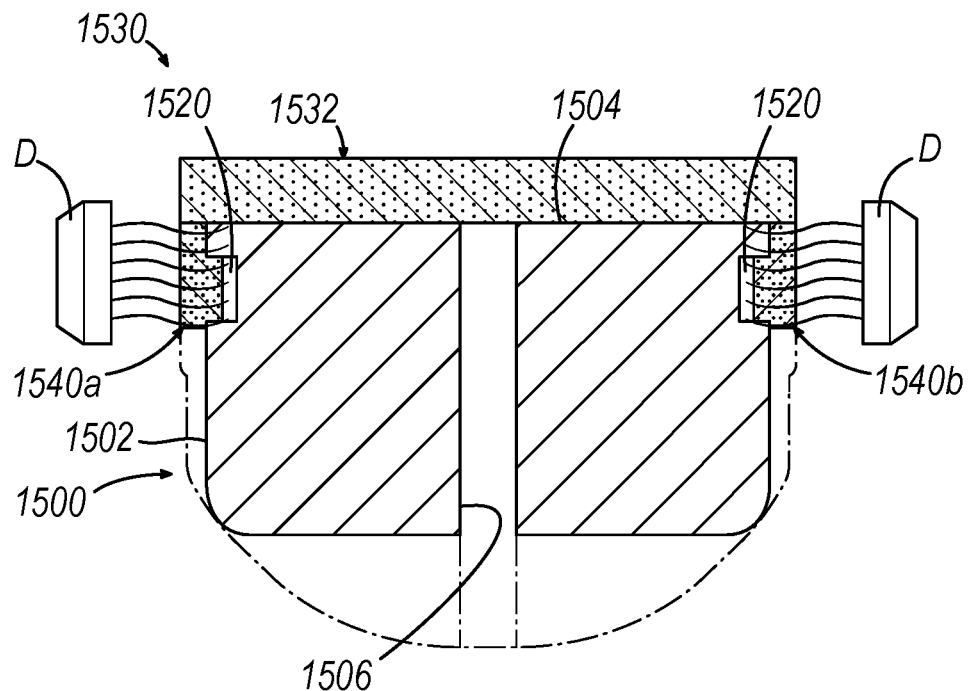
FIG. 30E depicts a cross-sectional end view of the adjunct of FIG. 29 positioned over the staple cartridge of FIG. 29, showing the moisture-sensitive foam attachment features transitioned from the wet state to the dry state by a pair of driers for attaching the adjunct to the staple cartridge.
Figure 30F:
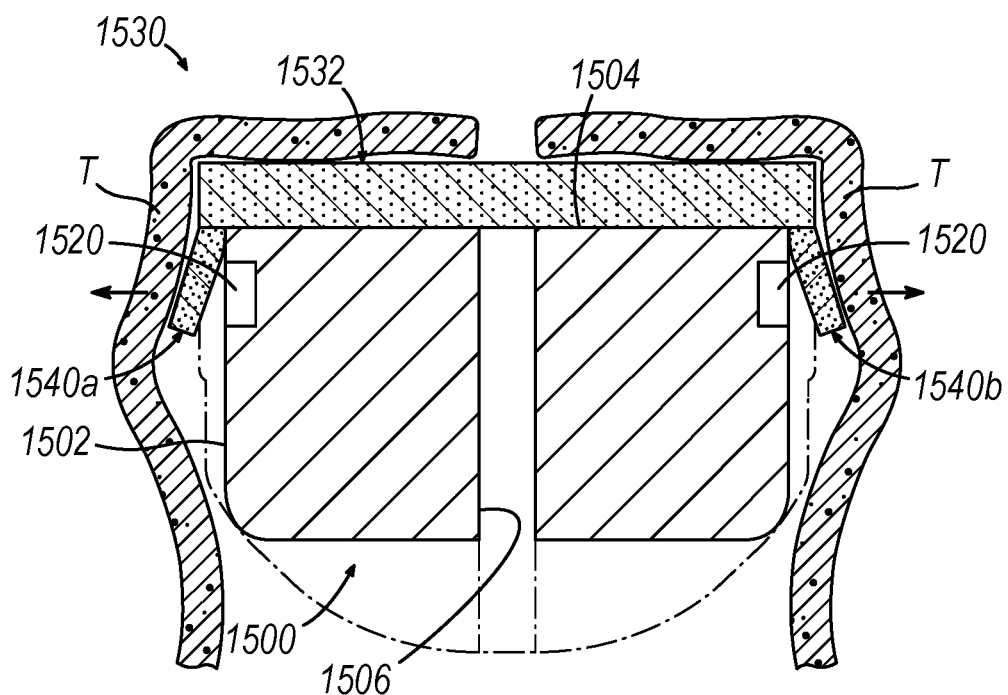
FIG. 30F depicts a cross-sectional end view of the adjunct of FIG. 29 positioned over the staple cartridge of FIG. 29, showing the moisture-sensitive foam attachment features transitioned from the dry state to the wet state by tissue within a patient's body for releasing the adjunct from the staple cartridge.

As shown in FIG. 30E, adjunct (1530) may be selectively attached to staple cartridge deck (1504) via tabs (1540a, 1540b) by drying tabs (1540a, 1540b), such as by a pair of transversely-opposed driers (D), to transition tabs (1540a, 1540b) from the wet state to the dry state while at least a portion of each tab (1540a, 1540b) remains deformed within the respective recess (1520) of cartridge body (1502) to provide an interference fit between tabs (1540a, 1540b) and recesses (1520). As shown in FIG. 30F, adjunct (1530) may be released from staple cartridge deck (1504) by tabs (1540a, 1540b) when tabs (1540a, 1540b) are re-exposed to moisture, such as by positioning adjunct (1530) adjacent to tissue (T) within a patient's body. Tabs (1540a, 1540b) of the present version are configured to passively release adjunct (1530) from staple cartridge deck (1504) in response to separation of end effector (50) from the stapled tissue (T). More particularly, staple cartridge deck (1504) may be lowered downwardly relative to adjunct (1530) during such separation of end effector (50) from the stapled tissue (T) and may urge tabs (1540a, 1540b) transversely outwardly for disengaging tabs (1540a, 1540b) from the respective recesses (1520). In some versions, the shape memory properties of tabs (1540a, 1540b) may urge tabs (1540a, 1540b) transversely outwardly when tabs (1540a, 1540b) are re-exposed to moisture, such that tabs (1540a, 1540b) may be configured to actively release adjunct (1530) from staple cartridge deck (1504) in response to positioning adjunct (1530) adjacent to tissue (T) within the patient's body.

While tabs (1540a, 1540b) have been described as being incorporated into multi-layer adjunct (1530), it will be appreciated that tabs (1540a, 1540b) may just as easily be incorporated into a compressible monolithic adjunct similar to adjunct (230) described above in connection with FIGS. 10-12.

N. Exemplary Adjunct with Foam Attachment Features for Engaging Cartridge Slot

Figure 31A:
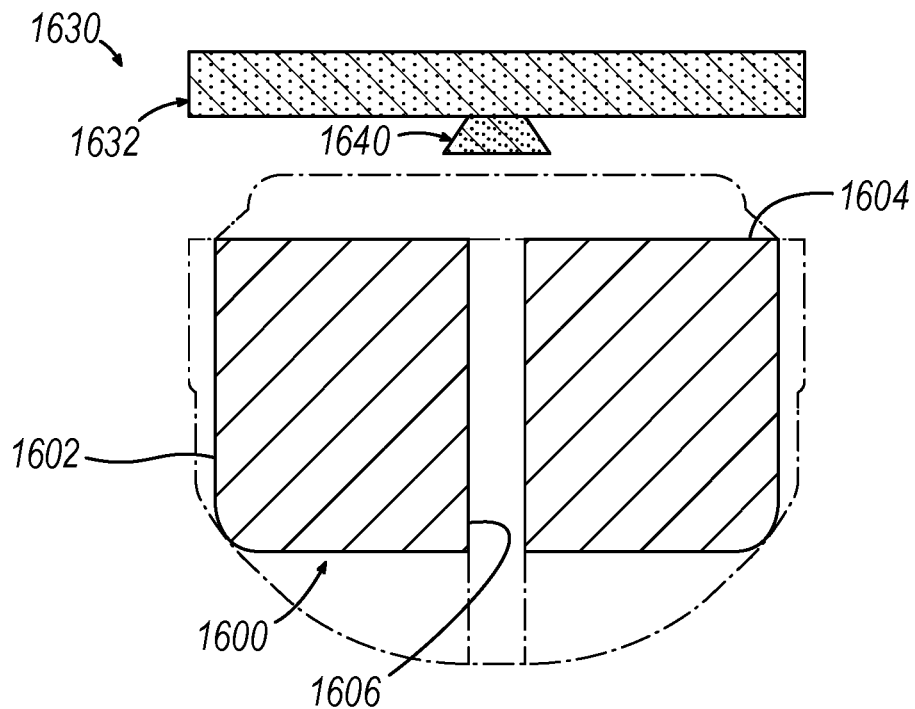
FIG. 31A depicts a cross-sectional end view of another exemplary staple cartridge in combination with another exemplary adjunct, showing the adjunct positioned above the staple cartridge with a moisture-sensitive foam attachment feature of the adjunct aligned with an elongate slot of the staple cartridge.
Figure 31B:
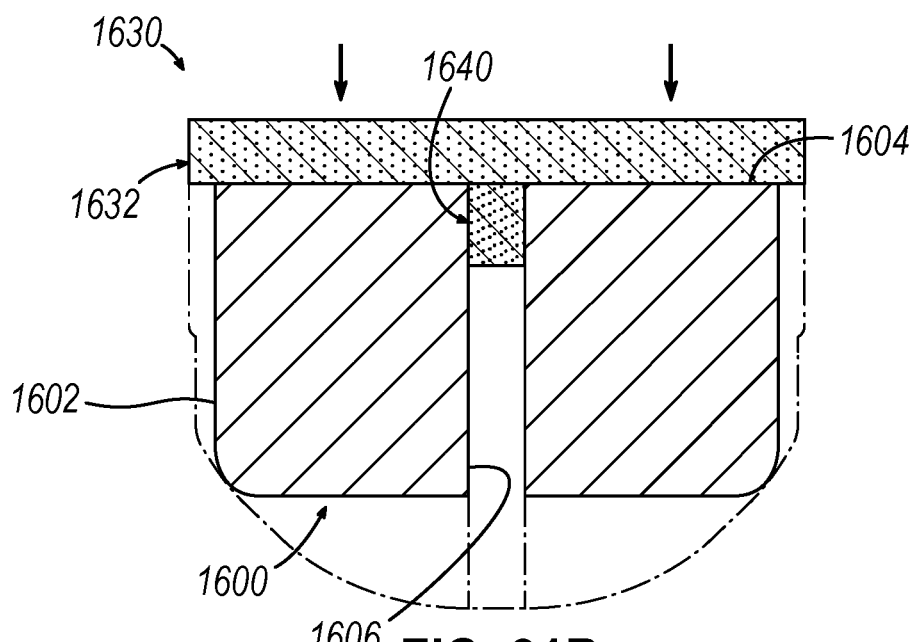
FIG. 31B depicts a cross-sectional end view of the adjunct of FIG. 31A positioned over the staple cartridge of FIG. 31A, showing the moisture-sensitive foam attachment feature of the adjunct received within the elongate slot of the staple cartridge for attaching the adjunct to the staple cartridge.

FIGS. 31A-31B show another exemplary multi-layer adjunct (1630) configured for releasable attachment to a staple cartridge (1600). Staple cartridge (1600) and adjunct (1630) are configured for use with end effector (50) and are similar to staple cartridge (70) and buttress assemblies (110, 112) described above except as otherwise described below. In this regard, staple cartridge (1600) includes a cartridge body (1602) having an upwardly facing deck (1604), an elongate slot (1606) extending along a central axis of cartridge body (1602) and opening upwardly through deck (1604), and a plurality of staple openings (not shown) extending through deck (1604) on each side of elongate slot (1606). Each staple opening slidably houses an unformed staple (not shown), similar to staple (80), and a respective staple driver (not shown) configured to drive the staple outwardly toward anvil (56) to be formed. A lower tray (not shown) of staple cartridge (1600) retains the staples and staple drivers within cartridge body (1602). Elongate slot (1606) of the present example is configured to facilitate releasable attachment of an adjunct, such as adjunct (1630), to staple cartridge deck (1604), as described in greater detail below.

Adjunct (1630) includes a buttress body (1632) which comprises a strong yet flexible material configured to structurally support a line of staples (80). By way of example only, buttress body (1632) may comprise a composite polymeric foam layer having material properties configured to provide a tissue compensating effect. In other versions, buttress body (1632) may comprise a mesh of polyglactin 910 material by Ethicon, Inc. of Somerville, New Jersey. Alternatively, any other suitable materials or combinations of materials may be used in addition to or as an alternative to polyglactin 910 material to form buttress body (1632).

In the example shown, adjunct (1630) further includes at least one attachment feature in the form of at least one transversely-centered shape memory tab (1640) coupled to a centerline of buttress body (1632) and configured to be at least partially received within elongate slot (1606). Tab (1640) comprises a moisture-sensitive composite shape memory polymeric foam configured to have a relatively high stiffness when dry and a relatively low stiffness when wet. In some versions, tab (1640) may extend along substantially an entire length of buttress body (1632). In other versions, a plurality of tabs (1640) may extend along respective portions of the length of buttress body (1632). Tab (1640) of the present version extends downwardly from the centerline of buttress body (1632) in a flared manner such that tab (1640) is deformable in the transverse direction when exposed to moisture.

As shown in FIG. 31A, adjunct (1630) may initially be positioned over staple cartridge deck (1604) with tab (1640) in a dry state in which tab (1640) has a first stiffness and in which at least a portion of tab (1640) is wider than elongate slot (1606). Tab (1640) may subsequently be exposed to moisture to thereby transition tab (1640) from the dry state to a wet state in which tab (1640) has a second stiffness less than the first stiffness. As shown in FIG. 31B, adjunct (1630) may then be positioned over staple cartridge deck (1604) with tab (1640) in the wet state such that tab (1640) may be deformably received within elongate slot (1606).

It will be appreciated that adjunct (1630) may be selectively attached to staple cartridge deck (1604) via tab (1640) by drying tab (1640) to transition tab (1640) from the wet state to the dry state while at least a portion of tab (1640) remains deformed within the elongate slot (1606) to provide an interference fit between tab (1640) and elongate slot (1606). It will also be appreciated that adjunct (1630) may be released from staple cartridge deck (1604) by tab (1640) when tab (1640) is re-exposed to moisture, such as by positioning adjunct (1630) adjacent to tissue within a patient's body. Tab (1640) of the present version is configured to passively release adjunct (1630) from staple cartridge deck (1604) in response to separation of end effector (50) from the stapled tissue. More particularly, staple cartridge deck (1604) may be lowered downwardly relative to adjunct (1630) during such separation of end effector (50) from the stapled tissue for disengaging tab (1640) from elongate slot (1606).

While tab (1640) has been described as being incorporated into multi-layer adjunct (1630), it will be appreciated that tab (1640) may just as easily be incorporated into a compressible monolithic adjunct similar to adjunct (230) described above in connection with FIGS. 10-12.

Figure 32:
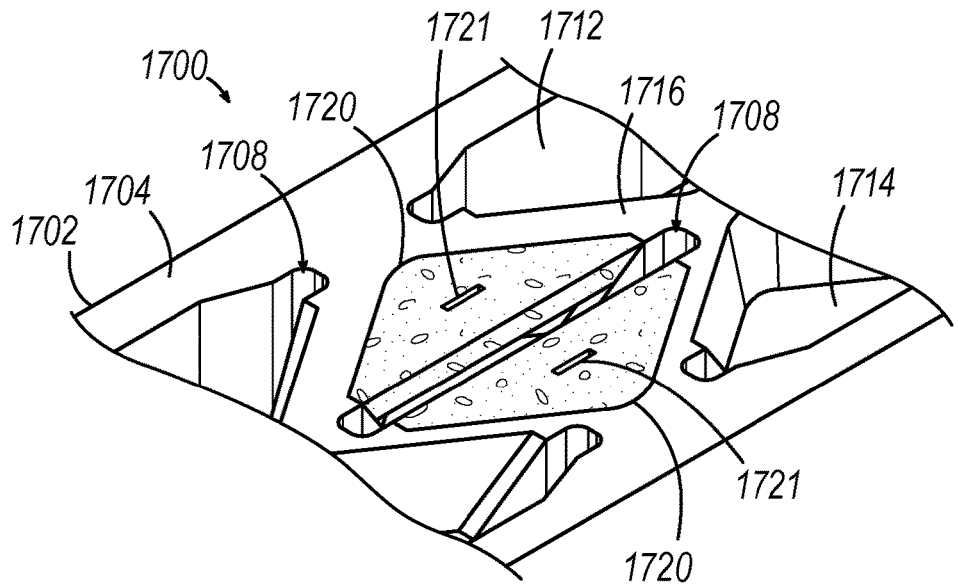
FIG. 32 depicts a partial perspective view of another exemplary staple cartridge, showing a pair of shape memory layers overmolded onto a cartridge body of the staple cartridge and each having a respective recess.

O. Exemplary Adjunct with Attachment Features for Engaging Expandable Recesses of Cartridge FIGS. 32-33C show another exemplary multi-layer adjunct (1730) configured for releasable attachment to a staple cartridge (1700). Staple cartridge (1700) and adjunct (1730) are configured for use with end effector (50) and are similar to staple cartridge (200) and buttress assemblies (110, 112) described above except as otherwise described below. In this regard, staple cartridge (1700) includes a cartridge body (1702) having an upwardly facing deck (1704), an elongate slot (not shown) extending along a central axis of cartridge body (1702) and opening upwardly through deck (1704), and a plurality of staple openings (1708) extending through deck (1704) on each side of the elongate slot. Each staple opening (1708) slidably houses an unformed staple (not shown), similar to staple (80), and a respective staple driver (not shown) configured to drive the staple outwardly toward anvil (56) to be formed. A lower tray (not shown) of staple cartridge (1700) retains the staples and staple drivers within cartridge body (1702). Cartridge body (1702) of the present example further includes a plurality of upwardly-opening recesses (1712, 1714, 1716) formed in deck (1704) and having base surfaces through which staple openings (1708) extend. More specifically, on each side of the elongate slot, deck (1704) includes an inner row of triangular recesses (1712) each having a medial apex that points transversely away from the elongate slot; an outer row of triangular recesses (1714) each having a medial apex that points transversely toward the elongate slot; and a middle row of diamond-shaped recesses (1716) each having an inner medial apex that points transversely toward the elongate slot and an opposed outer medial apex that points transversely away from the elongate slot.

In the example shown, a pair of shape memory layers (1720) are coupled to cartridge body (1702) within at least one diamond-shaped recess (1716) on opposite sides of the respective staple opening (1708), such as via overmolding. In some versions, each layer (1720) is recessed below an upper surface of deck (1704). In addition, or alternatively, each layer (1720) may be adhered to a sidewall defined by the respective diamond-shaped recess (1716). In any event, each layer (1720) comprises a moisture-sensitive and/or temperature-sensitive composite shape memory polymeric membrane configured to hydrothermally contract when exposed to a threshold humidity and/or temperature. A recess (1721) extends downwardly into each layer (1720) and is configured to facilitate releasable attachment of an adjunct, such as adjunct (1730), to staple cartridge deck (1704), as described in greater detail below.

Adjunct (1730) includes a buttress body (1732) which comprises a strong yet flexible material configured to structurally support a line of staples (80). By way of example only, buttress body (1732) may comprise a composite polymeric foam layer having material properties configured to provide a tissue compensating effect. In other versions, buttress body (1732) may comprise a mesh of polyglactin 910 material by Ethicon, Inc. of Somerville, New Jersey. Alternatively, any other suitable materials or combinations of materials may be used in addition to or as an alternative to polyglactin 910 material to form buttress body (1732).

In the example shown, adjunct (1730) further includes at least one attachment feature in the form of at least one post (1740) coupled to buttress body (1732) and configured to be at least partially received by a respective recess (1721). Post (1740) extends generally downwardly from buttress body (1732) and includes a lower bulbous (e.g., spherical) protrusion (1750) for selectively engaging a side surface(s) of the corresponding recess (1721).

Figure 33A:
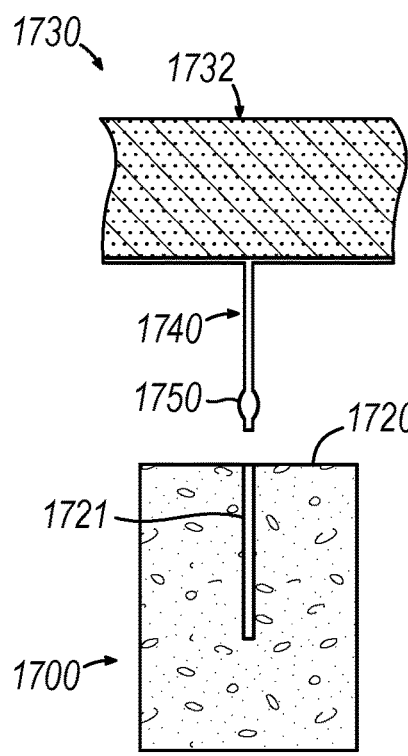
FIG. 33A depicts a partial cross-sectional end view of the staple cartridge of FIG. 32, showing another exemplary adjunct positioned above the staple cartridge with a rigid attachment feature of the adjunct aligned with a respective recess of the staple cartridge.
Figure 33B:
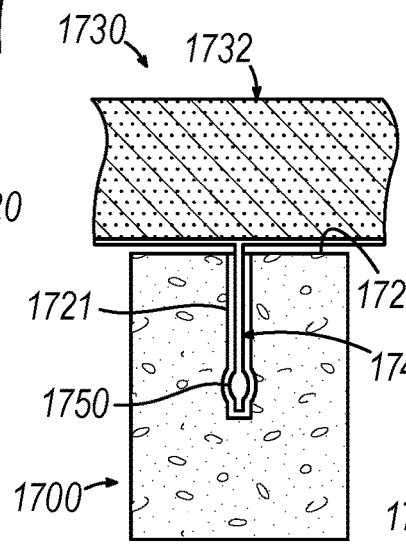
FIG. 33B depicts a partial cross-sectional end view of the adjunct of FIG. 33A positioned over the staple cartridge of FIG. 32, showing the rigid attachment feature of the adjunct received within the respective recess of the staple cartridge for attaching the adjunct to the staple cartridge.
Figure 33C:
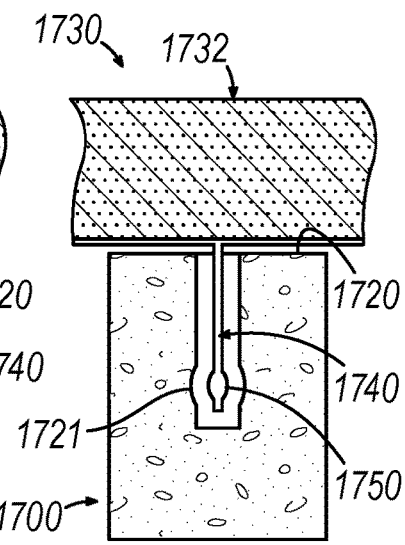
FIG. 33C depicts a partial cross-sectional end view of the adjunct of FIG. 33A positioned over the staple cartridge of FIG. 32, showing the rigid attachment feature of the adjunct received within the respective recess of the staple cartridge and the recess expanded for releasing the adjunct from the staple cartridge.

As shown in FIG. 33A, adjunct (1730) may initially be positioned over staple cartridge deck (1704) with each layer (1720) in a dry and/or cool (e.g., room temperature) state in which recess (1721) has a width at least slightly less than that of lower bulbous protrusion (1750). As shown in FIG. 33B, adjunct (1730) may be selectively attached to staple cartridge deck (1704) via post (1740) by inserting post (1740) into recess (1721) to provide a press fit between protrusion (1750) and the side surface(s) of recess (1721). In some versions, protrusion (1750) may engage the side surface(s) of recess (1721) for deforming the side surface(s) of recess (1721) slightly away from protrusion (1750) during attachment of adjunct (1730) to staple cartridge deck (1704) to facilitate insertion of post (1740) into recess (1721).

As shown in FIG. 33C, adjunct (1730) may be released from staple cartridge deck (1704) by each layer (1720) when each layer (1720) is exposed to moisture and/or heat, such as by positioning staple cartridge (1700) adjacent to tissue within a patient's body. Layer (1720) of the present version is configured to actively release adjunct (1730) from staple cartridge deck (1704) in response to positioning staple cartridge (1700) adjacent to tissue within the patient's body. More particularly, the shape memory property of layer (1720) may expand the side surface(s) of recess (1721) away from protrusion (1750) and thereby disengage protrusion (1750) from the side surface(s) of recess (1721) when layer (1720) is exposed to moisture and/or heat.

While post (1740) has been described as being incorporated into multi-layer adjunct (1730), it will be appreciated that post (1740) may just as easily be incorporated into a compressible monolithic adjunct similar to adjunct (230) described above in connection with FIGS. 10-12.

Figure 34A:
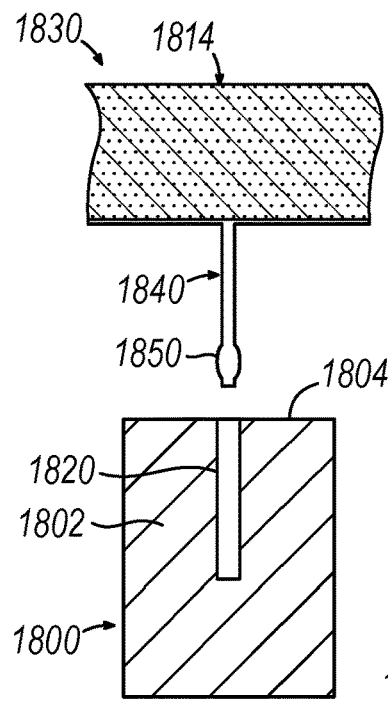
FIG. 34A depicts a partial cross-sectional end view of another exemplary staple cartridge in combination with another exemplary adjunct, showing the adjunct positioned above the staple cartridge with a shape memory attachment feature of the adjunct aligned with a respective recess of the staple cartridge.
Figure 34B:
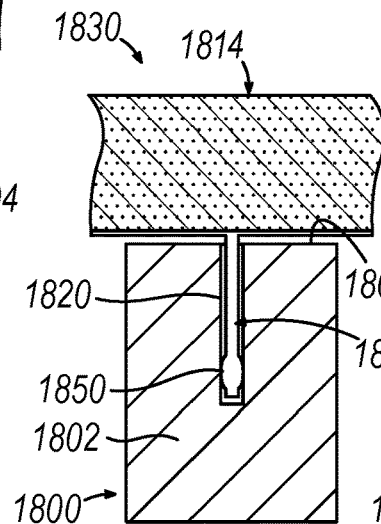
FIG. 34B depicts a partial cross-sectional end view of the staple cartridge and adjunct of FIG. 34A, showing the shape memory attachment feature of the adjunct received within the respective recess of the staple cartridge for attaching the adjunct to the staple cartridge.
Figure 34C:
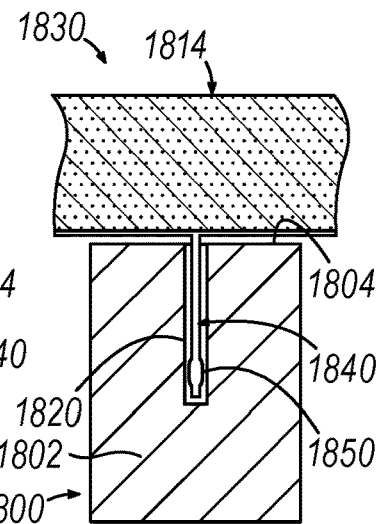
FIG. 34C depicts a partial cross-sectional end view of the staple cartridge and adjunct of FIG. 34A, showing the shape memory attachment feature of the adjunct received within the respective recess of the staple cartridge and the shape memory attachment feature contracted for releasing the adjunct from the staple cartridge.

P. Exemplary Adjunct with Expandable Attachment Features for Engaging Recesses of Cartridge FIGS. 34A-34C show another exemplary multi-layer adjunct (1830) configured for releasable attachment to a staple cartridge (1800). Staple cartridge (1800) and adjunct (1830) are configured for use with end effector (50) and are similar to staple cartridge (70) and buttress assemblies (110, 112) described above except as otherwise described below. In this regard, staple cartridge (1800) includes a cartridge body (1802) having an upwardly facing deck (1804), an elongate slot (not shown) extending along a central axis of cartridge body (1802) and opening upwardly through deck (1804), and a plurality of staple openings (not shown) extending through deck (1804) on each side of the elongate slot. Each staple opening slidably houses an unformed staple (not shown), similar to staple (80), and a respective staple driver (not shown) configured to drive the staple outwardly toward anvil (56) to be formed. A lower tray (not shown) of staple cartridge (1800) retains the staples and staple drivers within cartridge body (1802). Cartridge body (1802) of the present example further includes at least one upwardly-opening recess (1820) formed in deck (1804) and configured to facilitate releasable attachment of an adjunct, such as adjunct (1830), to staple cartridge deck (1804), as described in greater detail below.

Adjunct (1830) includes a buttress body (1814) which comprises a strong yet flexible material configured to structurally support a line of staples (80). By way of example only, buttress body (1814) may comprise a composite polymeric foam layer having material properties configured to provide a tissue compensating effect. In other versions, buttress body (1814) may comprise a mesh of polyglactin 910 material by Ethicon, Inc. of Somerville, New Jersey. Alternatively, any other suitable materials or combinations of materials may be used in addition to or as an alternative to polyglactin 910 material to form buttress body (1814).

In the example shown, adjunct (1830) further includes at least one attachment features in the form of at least one shape memory post (1840) coupled to buttress body (1814) and configured to be at least partially received within recess (1820). Post (1840) comprises a moisture-sensitive composite shape memory polymeric material configured to hydrothermally contract when exposed to a threshold humidity and/or temperature. Post (1840) extends generally downwardly from buttress body (1814) and includes a lower bulbous (e.g., spherical) protrusion (1850) for selectively engaging a side surface(s) of recess (1820).

As shown in FIG. 34A, adjunct (1830) may initially be positioned over staple cartridge deck (1804) with post (1840) in a dry and/or cool (e.g., room temperature) state in which lower bulbous protrusion (1850) has a width at least slightly greater than that of recess (1820). As shown in FIG. 34B, adjunct (1830) may be selectively attached to staple cartridge deck (1804) via post (1840) by inserting post (1840) into recess (1820) to provide a press fit between protrusion (1850) and the side surface(s) of recess (1820). In some versions, protrusion (1850) may engage the side surface(s) of recess (1820) for deforming protrusion (1850) slightly away from the side surface(s) of recess (1820) during attachment of adjunct (1830) to staple cartridge deck (1804) to facilitate insertion of post (1840) into recess (1820).

As shown in FIG. 34C, adjunct (1830) may be released from staple cartridge deck (1804) by post (1840) when post (1840) is exposed to moisture and/or heat, such as by positioning adjunct (1830) adjacent to tissue within a patient's body. Post (1840) of the present version is configured to actively release adjunct (1830) from staple cartridge deck (1804) in response to positioning adjunct (1830) adjacent to tissue within the patient's body. More particularly, the shape memory property of post (1840) may contract protrusion (1850) away from the side surface(s) of recess (1820) and thereby disengage protrusion (1850) from the side surface(s) of recess (1820) when post (1840) is exposed to moisture and/or heat.

While post (1840) has been described as being incorporated into multi-layer adjunct (1830), it will be appreciated that post (1840) may just as easily be incorporated into a compressible monolithic adjunct similar to adjunct (230) described above in connection with FIGS. 10-12.

Q. Exemplary Adjunct with Attachment Features for Engaging Cartridge Pan

Figure 35:
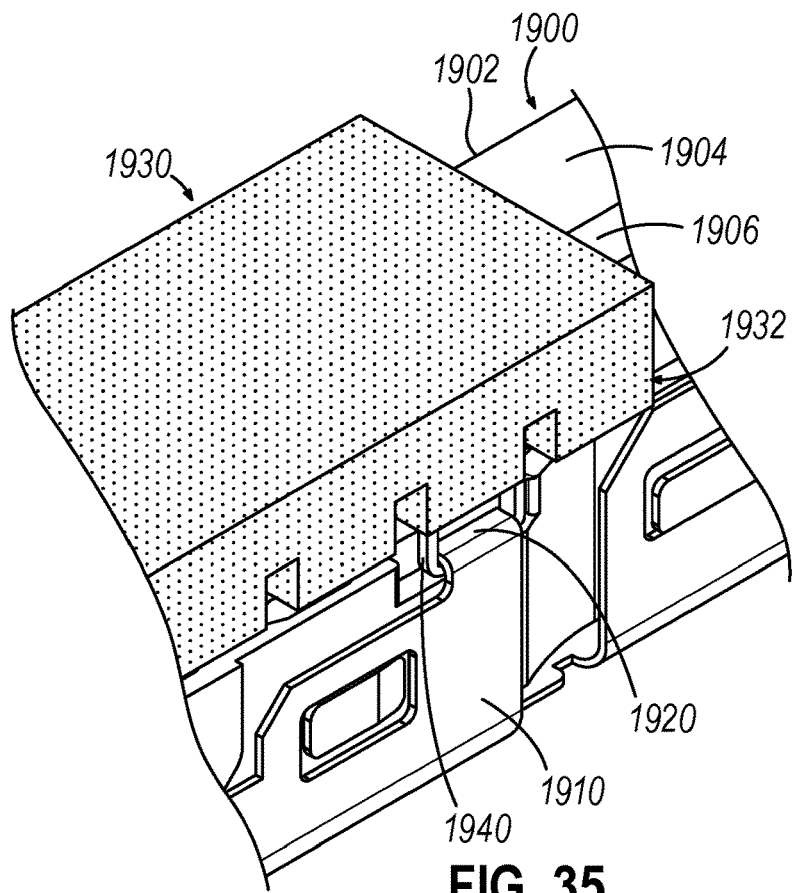
FIG. 35 depicts a partial perspective view of another exemplary staple cartridge in combination with another exemplary adjunct, showing a webbing arm attachment feature engaged with a cartridge pan finger of the staple cartridge for attaching the adjunct to the staple cartridge.

FIG. 35 shows another exemplary compressible monolithic adjunct (1930) configured for releasable attachment to a staple cartridge (1900). Staple cartridge (1900) and adjunct (1930) are configured for use with end effector (50) and are similar to staple cartridge (200) and adjunct (230) described above except as otherwise described below. In this regard, staple cartridge (1900) includes a cartridge body (1902) having an upwardly facing deck (1904), an elongate slot (1906) extending along a central axis of cartridge body (1902) and opening upwardly through deck (1904), and a plurality of staple openings (not shown) extending through deck (1904) on each side of the elongate slot. Each staple opening slidably houses an unformed staple (not shown), similar to staple (80), and a respective staple driver (not shown) configured to drive the staple outwardly toward anvil (56) to be formed. A lower tray (1910) of staple cartridge (1900) retains the staples and staple drivers within cartridge body (1902). Lower tray (1910) of the present example includes a pair of transversely-opposed fingers (1920) (one shown) extending upwardly toward an upper surface of deck (1904) and transversely inwardly thereover, and configured to facilitate releasable attachment of an adjunct, such as adjunct (1930), to staple cartridge deck (1904), as described in greater detail below.

Adjunct (1930) has a plurality of three-dimensional, resiliently compressible nodules (1932) that are integrally connected with one another in a plurality of linear arrays defining a lattice structure having an elongate rectangular shape in a manner similar to that described above in connection with FIGS. 10-12. Each nodule (1932) is constructed similar to nodules (332) described above has a generally cuboid shape defining four side surfaces, a lower surface (not shown), and an opening (not shown) in the lower surface that extends along a vertical central axis of nodule (1932) and defines an open, hollow interior of nodule (1932).

In the example shown, adjunct (1930) further includes a plurality of attachment features in the form of at least one pair of transversely-opposed webbing arms (1940) (one shown) coupled to transversely-outer nodules (1932) and configured to be caught by respective fingers (1920). Webbing arms (1940) each extend between the lower ends of a longitudinally-adjacent pair of nodules (1932) and each have a generally U-shaped profile.

Webbing arms (1940) of the present version are flexibly coupled to respective pairs of nodules (1932) such that webbing arms (1940) are bendable and/or stretchable. In some versions, any one or more of nodules (1932) and/or webbing arms (1940) may be integrally formed together as a unitary piece. For example, any one or more of nodules (1932) and/or webbing arms (1940) may be 3D-printed together. In some versions, webbing arms (1940) may be constructed of a different material than that of nodules (1932).

As shown in FIG. 35, adjunct (1930) may be selectively attached to staple cartridge deck (1904) via webbing arms (1940) when webbing arms (1940) are caught by respective fingers (1920) such that webbing arms (1940) are each captured between the respective finger (1920) and cartridge body (1902). Fingers (1920) of the present version are configured to passively release adjunct (1930) from staple cartridge deck (1904) in response to separation of end effector (50) from the stapled tissue. More particularly, staple cartridge deck (1904) may be lowered downwardly relative to adjunct (1930) during such separation of end effector (50) from the stapled tissue and may bend and/or stretch webbing arms (1940) until webbing arms (1940) are released by the respective fingers (1920). In some versions, webbing arms (1940) may include perforations and/or weakened portions such that webbing arms (1940) may be frangible for promoting tearing of webbing arms (1940) by fingers (1920).

Figure 36:
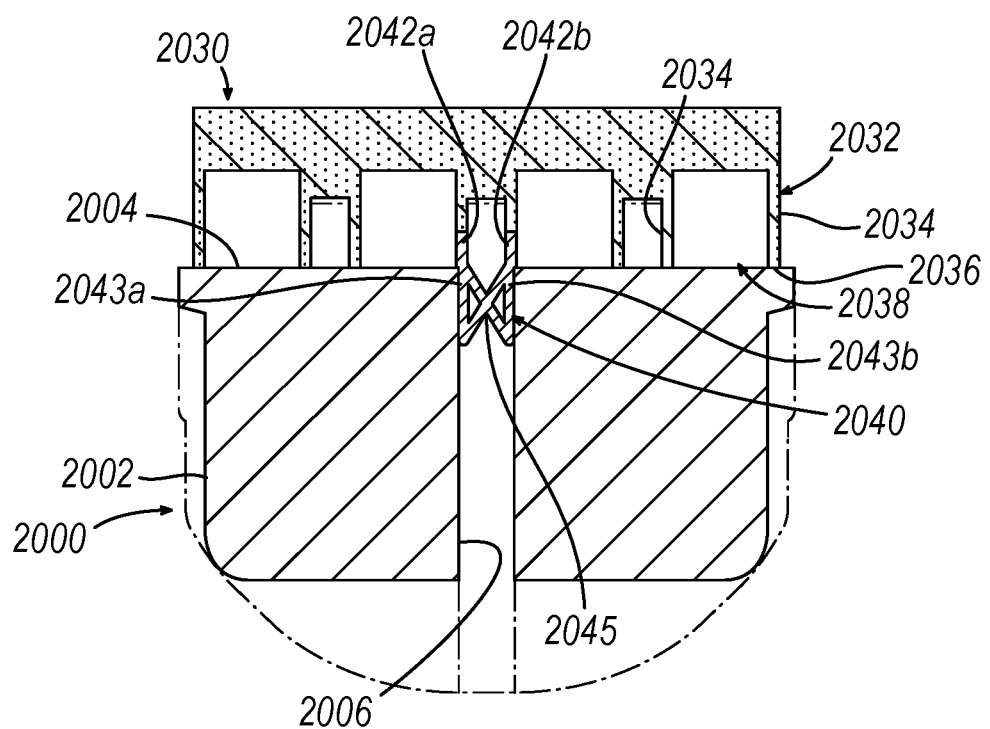
FIG. 36 depicts a cross-sectional end view of another exemplary staple cartridge in combination with another exemplary adjunct, showing a truss-shaped attachment feature of the adjunct received within an elongate slot of the staple cartridge for attaching the adjunct to the staple cartridge.

R. Exemplary Adjunct with Truss-Shaped Attachment Feature for Engaging Cartridge Slot FIG. 36 shows another exemplary compressible monolithic adjunct (2030) configured for releasable attachment to a staple cartridge (2000). Staple cartridge (2000) and adjunct (2030) are configured for use with end effector (50) and are similar to staple cartridge (200) and adjunct (230) described above except as otherwise described below. In this regard, staple cartridge (2000) includes a cartridge body (2002) having an upwardly facing deck (2004), an elongate slot (2006) extending along a central axis of cartridge body (2002) and opening upwardly through deck (2004), and a plurality of staple openings (not shown) extending through deck (2004) on each side of elongate slot (2006). Each staple opening slidably houses an unformed staple (not shown), similar to staple (80), and a respective staple driver (not shown) configured to drive the staple outwardly toward anvil (56) to be formed. A lower tray (not shown) of staple cartridge (2000) retains the staples and staple drivers within cartridge body (2002). Elongate slot (2006) of the present example is configured to facilitate releasable attachment of an adjunct, such as adjunct (2030), to staple cartridge deck (2004), as described in greater detail below.

Adjunct (2030) has a plurality of three-dimensional, resiliently compressible nodules (2032) that are integrally connected with one another in a plurality of linear arrays defining a lattice structure having an elongate rectangular shape in a manner similar to that described above in connection with FIGS. 10-12. Each nodule (2032) of the present example has a generally cuboid shape defining four side surfaces (2034), a lower surface (2036), and an opening (2038) in lower surface (2036) that extends along a vertical central axis of nodule (2032) and defines an open, hollow interior of nodule (2032).

In the example shown, adjunct (2030) further includes at least one attachment feature in the form of at least one transversely-centered truss-shaped rail (2040) coupled to transversely-inner nodules (2032) and configured to be at least partially received within elongate slot (2006). Rail (2040) includes a pair of angled beams (2042a, 2042b) extending generally downwardly and transversely inwardly from a sidewall of the respective nodule (2032) and a pair of vertical beams (2043a, 2043b) extending between angled beams (2042a, 2042b) for selectively engaging a respective side surface of elongate slot (2006). Angled beams (2042a, 2042b) intersect each other at a joint (2045) that is configured to be severed during firing of staple cartridge (2000), such as by cutting edge (62) of firing member (60). In some versions, rail (2040) may extend along substantially an entire length of the lattice structure defined by nodules (2032). In other versions, a plurality of rails (2040) may extend along respective portions of the length of the lattice structure defined by nodules (2032).

As shown in FIG. 36, adjunct (2030) may be selectively attached to staple cartridge deck (2004) via rail (2040) when rail (2040) is in an unsevered state. In the illustrated unsevered state, vertical beams (2043a, 2043b) engage respective side surfaces of elongate slot (2006) to thereby attach adjunct (2030) to staple cartridge deck (2004). In some versions, the side surfaces of elongate slot (2006) may engage respective surfaces of vertical beams (2043a, 2043b) for deflecting vertical beams (2043a, 2043b) slightly transversely inwardly during attachment of adjunct (2030) to staple cartridge deck (2004) to facilitate insertion of rail (2040) into elongate slot (2006), with vertical beams (2043a, 2043b) resiliently biased against the respective side surfaces of elongate slot (2006) to provide a friction fit therebetween. It will be appreciated that adjunct (2030) may be released from staple cartridge deck (2004) by separated, transversely-opposed segments of rail (2040) when rail (2040) is in the severed state. In the severed state (not shown), vertical beams (2043a, 2043b) may disengage the respective side surfaces of elongate slot (2006) to thereby release adjunct (2030) from staple cartridge deck (2004).

S. Exemplary Adjunct with Loop Attachment Features for Engaging Cartridge Hooks

Figure 37:
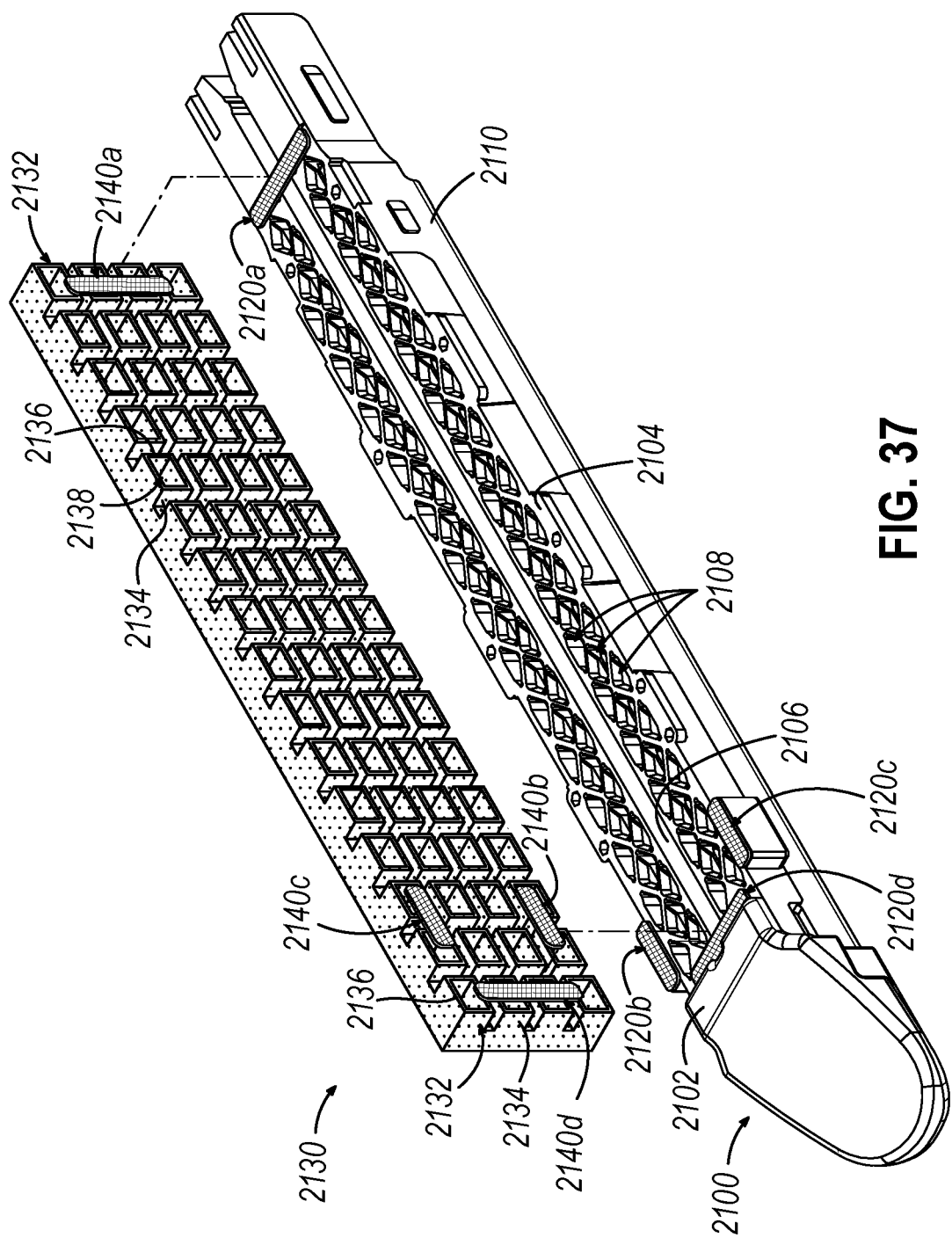
FIG. 37 depicts an exploded perspective view of another exemplary staple cartridge in combination with another exemplary adjunct, showing loop strips of the adjunct for selectively engaging hook strips of the staple cartridge.

FIG. 37 shows another exemplary compressible monolithic adjunct (2130) configured for releasable attachment to a staple cartridge (2100). Staple cartridge (2100) and adjunct (2130) are configured for use with end effector (50) and are similar to staple cartridge (200) and adjunct (230) described above except as otherwise described below. In this regard, staple cartridge (2100) includes a cartridge body (2102) having an upwardly facing deck (2104), an elongate slot (2106) extending along a central axis of cartridge body (2102) and opening upwardly through deck (2104), and a plurality of staple openings (2108) extending through deck (2104) on each side of elongate slot (2106). Each staple opening (2108) slidably houses an unformed staple (not shown), similar to staple (80), and a respective staple driver (not shown) configured to drive the staple outwardly toward anvil (56) to be formed. A lower tray (2110) of staple cartridge (2100) retains the staples and staple drivers within cartridge body (2102). Staple cartridge (2100) of the present example further includes a plurality of hook (e.g., Velcro) strips (2120a, 2120b, 2120c, 2120d) including a proximal hook strip (2120a), a transversely-opposed pair of medial hook strips (2120b, 2120c), and a distal hook strip (2120d) positioned on deck (2104) and configured to facilitate releasable attachment of an adjunct, such as adjunct (21030), to staple cartridge deck (2104), as described in greater detail below. In some versions, hook strips (2120a, 2120b, 2120c, 2120d) may each be molded onto or together with deck (2104).

Adjunct (2130) has a plurality of three-dimensional, resiliently compressible nodules (2132) that are integrally connected with one another in a plurality of linear arrays defining a lattice structure having an elongate rectangular shape in a manner similar to that described above in connection with FIGS. 10-12. Each nodule (2132) of the present example has a generally cuboid shape defining four side surfaces (2134), a lower surface (2136), and an opening (2138) in lower surface (2136) that extends along a vertical central axis of nodule (2132) and defines an open, hollow interior of nodule (2132).

In the example shown, adjunct (2130) further includes a plurality of attachment features in the form of loop (e.g., Velcro) strips (2140a, 2140b, 2140c, 2140d) including a proximal loop strip (2140a) coupled to proximal nodules (2032), a transversely-opposed pair of medial loop strips (2140b, 2140c) coupled to medial nodules (2032), and a distal loop strip (2140d) coupled to distal nodules (2032), each configured to be caught by respective hook strips (2120a, 2120b, 2120c, 2120d) in a hook-and-loop engagement. In some versions, loop strips (2140a, 2140b, 2140c, 2140d) may each define a plurality of pores (not shown) configured to be caught by corresponding hooks of hook strips (2120a, 2120b, 2120c, 2120d).

It will be appreciated that adjunct (2130) may be selectively attached to staple cartridge deck (2104) via loop strips (2140a, 2140b, 2140c, 2140d) when loop strips (2140a, 2140b, 2140c, 2140d) are caught by respective hook strips (2120a, 2120b, 2120c, 2120d). Hook strips (2120a, 2120b, 2120c, 2120d) of the present version are configured to passively release adjunct (2130) from staple cartridge deck (2104) in response to separation of end effector (50) from the stapled tissue. More particularly, staple cartridge deck (2104) may be lowered downwardly relative to adjunct (2130) during such separation of end effector (50) from the stapled tissue such that loop strips (2140a, 2140b, 2140c, 2140d) are released by the respective hook strips (2120a, 2120b, 2120c, 2120d).

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An adjunct configured for use with an end effector of a surgical stapler, comprising: (a) a tissue-effecting portion comprising a first material; and (b) at least one movable attachment feature coupled to the tissue-effecting portion and comprising a second material different from the first material, wherein the at least one movable attachment feature is configured to releasably attach the tissue-effecting portion to a stapling surface of the end effector, wherein the tissue-effecting portion is configured to contact tissue clamped by the end effector during closure thereof, wherein the tissue-effecting portion is further configured to be pierced and captured by staples ejected from the end effector into the clamped tissue and thereby reinforce the engagement between the ejected staples and the clamped tissue.

Example 2

The adjunct of Example 1, wherein the at least one movable attachment feature includes a plurality of movable attachment features each configured to releasably attach the tissue-effecting portion to the stapling surface at corresponding discrete locations along the stapling surface.

Example 3

The adjunct of any of the preceding Examples, wherein the at least one movable attachment feature is configured to transition between a first state in which the at least one movable attachment feature attaches the tissue-effecting portion to the stapling surface and a second state in which the at least one movable attachment feature releases the tissue-effecting portion from the stapling surface.

Example 4

The adjunct of any of the preceding Examples, wherein the at least one movable attachment feature includes at least one protrusion configured to engage at least one of an elongate slot or an undercut feature of the end effector for attaching the tissue-effecting portion to the stapling surface.

Example 5

The adjunct of Example 4, wherein the at least one movable attachment feature is configured to move transversely inwardly toward a longitudinal centerline of the adjunct in response to ejection of the staples from the end effector for releasing the tissue-effecting portion from the stapling surface.

Example 6

The adjunct of any of Examples 4 through 5, wherein the at least one movable attachment feature is configured to transition to a flush state in which the at least one movable attachment is substantially flat against the tissue-effecting portion in response to release of the tissue-effecting portion from the stapling surface.

Example 7

The adjunct of any of Examples 4 through 6, wherein the at least one protrusion is elastically deformable.

Example 8

The adjunct of any of the preceding Examples, wherein the second material includes a polymeric shape memory material.

Example 9

The adjunct of Example 8, wherein the polymeric shape memory material has a first stiffness when the polymeric shape memory material is dry, wherein the polymeric shape memory material has a second stiffness less than the first stiffness when the polymeric shape memory material is wet.

Example 10

The adjunct of any of the preceding Examples, wherein the at least one attachment feature is frangible.

Example 11

The adjunct of any of the preceding Examples, wherein the at least one attachment feature includes a rail having a hollow interior, wherein the rail is configured to be severed in response to ejection of the staples from the end effector for releasing the tissue-effecting portion from the stapling surface.

Example 12

The adjunct of any of the preceding Examples, wherein the tissue-effecting portion includes a lattice structure defined by a plurality of resiliently compressible nodules.

Example 13

The adjunct of any of the preceding Examples, wherein the plurality of resiliently compressible nodules and the at least one attachment feature are integrally formed together as a unitary piece.

Example 14

The adjunct of any of the preceding Examples, wherein the tissue-effecting portion includes a buttress body.

Example 15

A surgical stapler, comprising: (a) an end effector including: (i) a first stapling surface, and (ii) a second stapling surface configured to cooperate with the first stapling surface to clamp and staple tissue; and (b) the adjunct of any of the preceding Examples, wherein the tissue-effecting portion of the adjunct is releasably attached to one of the first stapling surface or the second stapling surface via the at least one movable attachment feature.

Example 16

An adjunct configured for use with an end effector of a surgical stapler, comprising:
(a) a lattice structure comprising a first material; and (b) at least one latch coupled to the lattice structure and comprising a second material different from the first material, wherein the at least one latch is configured to releasably attach the lattice structure to a stapling surface of the end effector, wherein the lattice structure is configured to contact tissue clamped by the end effector during closure thereof, wherein the lattice structure is further configured to be pierced and captured by staples ejected from the end effector into the clamped tissue and thereby reinforce the engagement between the ejected staples and the clamped tissue.

Example 17

The adjunct of Example 16, wherein the lattice structure is defined by a plurality of resiliently compressible nodules.

Example 18

The adjunct of any of Examples 16 through 17, wherein the at least one latch is deflectable.

Example 19

An adjunct configured for use with an end effector of a surgical stapler, comprising: (a) a lattice structure comprising a first material; and (b) at least one rail coupled to the lattice structure and comprising a second material different from the first material, wherein the at least one rail is configured to releasably attach the lattice structure to a stapling surface of the end effector, wherein the lattice structure is configured to contact tissue clamped by the end effector during closure thereof, wherein the lattice structure is further configured to be pierced and captured by staples ejected from the end effector into the clamped tissue and thereby reinforce the engagement between the ejected staples and the clamped tissue.

Example 20

The adjunct of Example 19, wherein the at least one rail is at least one of dovetail-shaped or T-shaped.

VI. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. patent application Ser. No. 17/514,073, entitled "Displaceable Adjunct Attachment Features for Surgical Stapler," filed on Oct. 29, 2021, published as U.S. Pat. Pub. No. 2023/0139479 on May 4, 2023; and U.S. patent application Ser. No. 17/514,126, entitled "Compressible Adjunct for Surgical Stapler," filed on Oct. 29, 2021, published as U.S. Pat. Pub. No. 2023/0140285 on May 4, 2023. The disclosure of each of these U.S. patent references is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An adjunct configured for use with an end effector of a surgical stapler, comprising:
   (a) a tissue-effecting portion comprising a first material; and
   (b) at least one movable attachment feature coupled to the tissue-effecting portion and comprising a second material different from the first material, wherein the at least one movable attachment feature is configured to releasably attach the tissue-effecting portion to a stapling surface of the end effector,
   wherein the tissue-effecting portion is configured to contact tissue clamped by the end effector during closure thereof,
   wherein the tissue-effecting portion is further configured to be pierced and captured by staples ejected from the end effector into the clamped tissue and thereby reinforce the engagement between the ejected staples and the clamped tissue,
   wherein the at least one movable attachment feature is configured to move relative to the tissue-effecting portion between a first state in which the at least one movable attachment feature attaches the tissue-effecting portion to the stapling surface and a second state in which the at least one movable attachment feature releases the tissue-effecting portion from the stapling surface,
   wherein the at least one movable attachment feature is configured to remain coupled to the tissue-effecting portion when in both the first and second states,
   wherein the at least one movable attachment feature is configured to move from the first state to the second state in response to ejection of the staples from the end effector.

2. The adjunct of claim 1, wherein the at least one movable attachment feature includes a plurality of movable attachment features each configured to releasably attach the tissue-effecting portion to the stapling surface at corresponding discrete locations along the stapling surface.

3. The adjunct of claim 1, wherein the at least one movable attachment feature includes at least one protrusion configured to engage at least one of an elongate slot or an undercut feature of the end effector for attaching the tissue-effecting portion to the stapling surface.

4. The adjunct of claim 3, wherein the at least one movable attachment feature is configured to move transversely inwardly toward a longitudinal centerline of the adjunct in response to ejection of the staples from the end effector for releasing the tissue-effecting portion from the stapling surface.

5. The adjunct of claim 3, wherein the at least one movable attachment feature is configured to transition to a flush state in which the at least one movable attachment is substantially flat against the tissue-effecting portion in response to release of the tissue-effecting portion from the stapling surface.

6. The adjunct of claim 3, wherein the at least one protrusion is elastically deformable.

7. The adjunct of claim 1, wherein the second material includes a polymeric shape memory material.

8. The adjunct of claim 7, wherein the polymeric shape memory material has a first stiffness when the polymeric shape memory material is dry, wherein the polymeric shape memory material has a second stiffness less than the first stiffness when the polymeric shape memory material is wet.

9. The adjunct of claim 1, wherein the at least one attachment feature is frangible.

10. The adjunct of claim 1, wherein the at least one attachment feature includes a rail having a hollow interior, wherein the rail is configured to be severed in response to ejection of the staples from the end effector for releasing the tissue-effecting portion from the stapling surface.

11. The adjunct of claim 1, wherein the tissue-effecting portion includes a lattice structure defined by a plurality of resiliently compressible nodules.

12. The adjunct of claim 11, wherein the plurality of resiliently compressible nodules and the at least one attachment feature are integrally formed together as a unitary piece.

13. The adjunct of claim 1, wherein the tissue-effecting portion includes a buttress body.

14. The adjunct of claim 1, wherein the at least one movable attachment feature is configured to move from the first state to the second state in response to ejection of the staples from the end effector while the end effector is closed.

15. A surgical stapler, comprising:
   (a) an end effector including:
      (i) a first stapling surface, and
      (ii) a second stapling surface configured to cooperate with the first stapling surface to clamp and staple tissue; and
   (b) the adjunct of claim 1, wherein the tissue-effecting portion of the adjunct is releasably attached to one of the first stapling surface or the second stapling surface via the at least one movable attachment feature.

16. An adjunct configured for use with an end effector of a surgical stapler, comprising:
   (a) a lattice structure comprising a first material; and
   (b) at least one latch coupled to the lattice structure and comprising a second material different from the first material, wherein the at least one latch is configured to releasably attach the lattice structure to a stapling surface of the end effector,
   wherein the lattice structure is configured to contact tissue clamped by the end effector during closure thereof,
   wherein the lattice structure is further configured to be pierced and captured by staples ejected from the end effector into the clamped tissue and thereby reinforce the engagement between the ejected staples and the clamped tissue,
   wherein the at least one latch is configured to be selectively engaged by at least one staple driver of the end effector for transitioning the at least one latch from a first state in which the at least one latch attaches the lattice structure to the stapling surface, to a second state in which the at least one latch releases the lattice structure from the stapling surface.

17. The adjunct of claim 16, wherein the lattice structure is defined by a plurality of resiliently compressible nodules.

18. The adjunct of claim 16, wherein the at least one latch is deflectable.

19. An adjunct configured for use with an end effector of a surgical stapler, comprising:
  (a) a lattice structure comprising a first material; and
  (b) at least one rail coupled to the lattice structure and comprising a second material different from the first material, wherein the at least one rail is configured to releasably attach the lattice structure to a stapling surface of the end effector,
  wherein the lattice structure is configured to contact tissue clamped by the end effector during closure thereof,
  wherein the lattice structure is further configured to be pierced and captured by staples ejected from the end effector into the clamped tissue and thereby reinforce the engagement between the ejected staples and the clamped tissue,
  wherein at least a portion of the at least one rail is resiliently biased transversely inwardly relative to a longitudinal axis of the at least one rail,
  wherein the at least one rail is configured to release the lattice structure from the stapling surface in response to ejection of the staples from the end effector while the end effector is closed.

20. The adjunct of claim 19, wherein the at least one rail is at least one of dovetail-shaped or T-shaped.

* * * * *